(12) United States Patent
Covalin et al.

(10) Patent No.: US 11,351,370 B2
(45) Date of Patent: Jun. 7, 2022

(54) DEVICES AND METHODS FOR TREATING COGNITIVE DYSFUNCTION AND DEPRESSION USING ELECTRICAL STIMULATION

(71) Applicant: Spark Biomedical, Inc., Friendswood, TX (US)

(72) Inventors: Alejandro Covalin, Los Angeles, CA (US); Navid Khodaparast, Dallas, TX (US); Daniel Powell, Friendswood, TX (US)

(73) Assignee: Spark Biomedical, Inc., Friendswood, TX (US)

(*) Notice: Subject to any disclaimer, the term of this patent is extended or adjusted under 35 U.S.C. 154(b) by 0 days.

(21) Appl. No.: 17/219,712

(22) Filed: Mar. 31, 2021

(65) Prior Publication Data

US 2021/0213286 A1    Jul. 15, 2021

Related U.S. Application Data

(63) Continuation-in-part of application No. 16/846,220, filed on Apr. 10, 2020, now Pat. No. 10,967,182, (Continued)

(51) Int. Cl.
| | |
|---|---|
| *A61N 1/36* | (2006.01) |
| *A61N 1/05* | (2006.01) |
| *A61N 1/04* | (2006.01) |

(52) U.S. Cl.
CPC ....... *A61N 1/36028* (2013.01); *A61N 1/0456* (2013.01); *A61N 1/0526* (2013.01)

(58) Field of Classification Search
CPC ............. A61N 1/0456; A61N 1/36025; A61N 1/36036; A61N 1/0526; A61N 1/36028
See application file for complete search history.

(56) References Cited

U.S. PATENT DOCUMENTS

| | | |
|---|---|---|
| 4,014,323 A | 3/1977 | Gilmer et al. |
| 4,690,144 A | 9/1987 | Rise et al. |
| (Continued) | | |

FOREIGN PATENT DOCUMENTS

| | | |
|---|---|---|
| WO | 2015109018 | 7/2015 |
| WO | 2015179571 | 11/2015 |
| WO | 2021011165 | 1/2021 |

OTHER PUBLICATIONS

Jenkins et al., "Transcutaneous Auricular Neurostimulation (tAN): A Novel Adjuvant Treatment in Neonatal Opioid Withdrawal Syndrome", Mar. 8, 2021, Frontiers in Human Neuroscience. (Year: 2021).*

(Continued)

*Primary Examiner* — George R Evanisko
(74) *Attorney, Agent, or Firm* — Gardella Grace P.A.

(57) ABSTRACT

Systems and methods for treating cognitive dysfunction and/or depression using transcutaneous auricular neurostimulation therapy may include positioning a wearable neurostimulation device about the ear of the patient, connecting the wearable neurostimulation device, to a pulse generator, and delivering a first series of stimulation pulses to at least one first electrode, the first series being configured to increase monoamine neurotransmitter availability, and delivering a second series of stimulation pulses to at least one second electrode, the second series being configured to upregulate opioid receptor agonists.

22 Claims, 29 Drawing Sheets

Related U.S. Application Data which is a continuation-in-part of application No. 16/510,930, filed on Jul. 14, 2019, now Pat. No. 10,695,568.

(60) Provisional application No. 62/777,569, filed on Dec. 10, 2018.

(56) References Cited

U.S. PATENT DOCUMENTS

| | | | |
|---|---|---|---|
| 4,865,048 A | 9/1989 | Eckerson | |
| 4,966,164 A | 10/1990 | Colsen et al. | |
| 5,514,175 A * | 5/1996 | Kim | A61H 39/002 |
| | | | 607/136 |
| 5,593,432 A | 1/1997 | Crowther et al. | |
| 6,567,702 B1 | 5/2003 | Nekhendzy et al. | |
| 6,697,670 B2 | 2/2004 | Chomenky et al. | |
| 7,386,347 B2 | 6/2008 | Chung et al. | |
| 7,493,171 B1 | 2/2009 | Whitehurst et al. | |
| 7,797,042 B2 | 9/2010 | Dietrich et al. | |
| 7,856,275 B1 | 12/2010 | Paul et al. | |
| 7,986,996 B2 | 7/2011 | Bell | |
| 8,204,601 B2 | 6/2012 | Moyer et al. | |
| 8,506,469 B2 | 8/2013 | Dietrich et al. | |
| 8,554,324 B2 | 10/2013 | Brocke | |
| 8,666,502 B2 | 3/2014 | Hartlep et al. | |
| 8,688,239 B2 | 4/2014 | Hartlep et al. | |
| 8,700,163 B2 | 4/2014 | Terry, Jr. et al. | |
| 8,751,020 B2 | 6/2014 | Beck et al. | |
| 8,755,892 B2 | 6/2014 | Amurthur et al. | |
| 8,885,861 B2 | 11/2014 | Beck et al. | |
| 8,918,178 B2 | 12/2014 | Simon et al. | |
| 8,942,814 B2 | 1/2015 | Szeles | |
| 8,965,518 B2 | 2/2015 | Ellrich et al. | |
| 9,089,691 B2 | 7/2015 | Libbus et al. | |
| 9,089,719 B2 | 7/2015 | Simon et al. | |
| 9,101,766 B2 | 8/2015 | Nekhendzy | |
| 9,216,290 B2 | 12/2015 | Terry, Jr. et al. | |
| 9,314,611 B2 | 4/2016 | Zschaeck et al. | |
| 9,415,220 B1 * | 8/2016 | Spinelli | A61N 1/36036 |
| 9,662,269 B2 | 5/2017 | Brown et al. | |
| 9,782,584 B2 | 10/2017 | Cartledge et al. | |
| 9,839,577 B2 | 12/2017 | Brown et al. | |
| 1,002,254 A1 | 7/2018 | Pfeifer | |
| 10,010,479 B2 | 7/2018 | Brown et al. | |
| 10,058,478 B2 | 8/2018 | Schnetz et al. | |
| 10,130,809 B2 | 11/2018 | Cartledge et al. | |
| 10,155,114 B2 | 12/2018 | De Ridder | |
| 10,213,601 B2 | 2/2019 | Simon et al. | |
| 10,279,178 B2 | 5/2019 | Cartledge et al. | |
| 10,322,062 B2 | 6/2019 | Brown et al. | |
| 10,413,719 B2 | 9/2019 | Brown et al. | |
| 10,426,945 B2 | 10/2019 | Tyler et al. | |
| 10,695,568 B1 | 6/2020 | Covalin | |
| 10,780,264 B2 | 9/2020 | Alam | |
| 10,828,461 B2 | 11/2020 | Cartledge et al. | |
| 10,857,360 B2 | 12/2020 | Waclawik | |
| 2005/0165460 A1 | 7/2005 | Erfan | |
| 2006/0064139 A1 | 3/2006 | Chung et al. | |
| 2007/0250145 A1 | 10/2007 | Kraus et al. | |
| 2008/0021517 A1 | 1/2008 | Dietrich | |
| 2008/0021520 A1 | 1/2008 | Dietrich | |
| 2008/0051852 A1 | 2/2008 | Dietrich et al. | |
| 2008/0249594 A1 | 10/2008 | Dietrich et al. | |
| 2009/0287035 A1 | 11/2009 | Dietrich et al. | |
| 2010/0057154 A1 | 3/2010 | Dietrich et al. | |
| 2010/0222843 A1 | 9/2010 | Tass et al. | |
| 2010/0262205 A1 | 10/2010 | De Ridder | |
| 2011/0166624 A1 | 7/2011 | Dietrich et al. | |
| 2013/0079862 A1 | 3/2013 | Ellrich | |
| 2013/0150923 A1 | 6/2013 | Schnetz et al. | |
| 2013/0231729 A1 | 9/2013 | Hartlep et al. | |
| 2013/0231730 A1 | 9/2013 | Hartlep et al. | |
| 2014/0046406 A1 | 2/2014 | Ellrich et al. | |
| 2014/0121740 A1 | 5/2014 | Patterson et al. | |
| 2014/0126752 A1 | 5/2014 | Beck et al. | |
| 2014/0135886 A1 * | 5/2014 | Cook | A61N 1/0456 |
| | | | 607/136 |
| 2014/0142669 A1 | 5/2014 | Cook et al. | |
| 2015/0018925 A1 | 1/2015 | Zschaeck et al. | |
| 2015/0018926 A1 | 1/2015 | Frenkel et al. | |
| 2015/0080986 A9 | 3/2015 | Ellrich et al. | |
| 2015/0165195 A1 | 6/2015 | Hartlep et al. | |
| 2015/0174418 A1 | 6/2015 | Tyler et al. | |
| 2017/0296807 A1 | 10/2017 | Brown et al. | |
| 2017/0368329 A1 * | 12/2017 | Tyler | A61N 1/36036 |
| 2018/0085573 A1 | 3/2018 | Alam | |
| 2018/0200522 A1 | 7/2018 | Taca, Jr. | |
| 2018/0296435 A1 | 10/2018 | Brown et al. | |
| 2018/0318585 A1 | 11/2018 | Pfeifer | |
| 2018/0339148 A1 | 11/2018 | Kong | |
| 2019/0046794 A1 | 2/2019 | Goodall et al. | |
| 2019/0111259 A1 | 4/2019 | De Ridder | |
| 2019/0151646 A1 | 5/2019 | Cakmak | |
| 2019/0262229 A1 | 8/2019 | Brown et al. | |
| 2019/0275322 A1 | 9/2019 | Cartledge et al. | |
| 2020/0030608 A1 | 1/2020 | Halpern | |
| 2020/0038658 A1 | 2/2020 | Tyler et al. | |
| 2020/0108250 A1 | 4/2020 | Ireland | |
| 2020/0139124 A1 * | 5/2020 | Amurthur | A61H 39/007 |
| 2020/0197707 A1 | 6/2020 | Covalin | |
| 2020/0238085 A1 | 7/2020 | Khodaparast et al. | |
| 2020/0261688 A1 | 8/2020 | Thoma | |
| 2020/0261722 A1 | 8/2020 | Alataris et al. | |
| 2020/0323684 A1 | 10/2020 | O'Leary et al. | |
| 2020/0345970 A1 | 11/2020 | La Rovere et al. | |
| 2021/0001124 A1 | 1/2021 | Brown et al. | |
| 2021/0038879 A1 | 2/2021 | Pfeifer | |
| 2021/0069505 A1 | 3/2021 | Romine et al. | |
| 2021/0077812 A1 | 3/2021 | Hool et al. | |

OTHER PUBLICATIONS

Sailer, et al., Altered reward processing in the nucleus accumbens and mesial prefrontal cortex of patients with posttraumatic stress disorder, Neuropsychologia, 46:11, May 2008, pp. 2836-2844, DOI: 10.1016/j.neuropsychologia.2008.05.022.

Neylan, Thomas C., Frontal Lobe Moderators and Mediators of Response to Exposure Therapy in PTSD, Am J Psychiatry, 174:12, Dec. 2017, pp. 1131-1133, DOI: 10.1176/appi.ajp.2017.17091056.

Mehta, et al., Inflammation, reward circuitry and symptoms of anhedonia and PTSD in trauma-exposed women, Social Cognitive and Affective Neuroscience, vol. 15, Issue 10, 2020, pp. 1046-1055, DOI: 10.1093/scan/nsz100.

Boukezzi, et al., Posttraumatic Stress Disorder is associated with altered reward mechanisms during the anticipation and the outcome of monetary incentive cues, NeuroImage: Clinical, vol. 25, 102073, 2020, DOI: 10.1016/j.nicl.2019.102073.

Sherin, Jonathan E., and Nemeroff, Charles B., Post-traumatic stress disorder: the neurobiological impact of psychological trauma, Dialogues in Clinical Neuroscience, vol. 13, No. 3, 2011, pp. 263-278.

Somohano, et al., PTSD symptom clusters and craving differs by primary drug of choice, J Dual Diagn., 15(4), 2019, pp. 233-242, DOI: 10.1080/15504263.2019.1637039.

Elman, et al., Reward and aversion processing in patients with post-traumatic stress disorder: functional neuroimaging with visual and thermal stimuli, Translational Psychiatry, 8:240, Nov. 2018, pp. 1-15, DOI: 10.1038/s41398-018-0292-6.

Seidemann, et al., The Reward System and Post-Traumatic Stress Disorder: Does Trauma Affect the Way We nteract With Positive Stimuli?, Chronic Stress, vol. 5, Feb. 25, 2021, pp. 1-11, DOI: 10.1177/2470547021996006.

Torrisi, et al., Therapeutic Challenges of Post-traumatic Stress Disorder: Focus on the Dopaminergic System, Frontiers in Pharmacology, vol. 10, Article 404, Apr. 17, 2019, pp. 1-11, DOI: 10.3389/fphar.2019.00404.

Basner, et al., Continuous and Intermittent Artificial Gravity as a Countermeasure to the Cognitive Effects of 60 Days of Head-Down Tilt Bed Rest, Frontiers in Physiology, vol. 12, Article 643854, Mar. 17, 2021, pp. 1-14, DOI: 10.3389/fphys.2021.643854.

(56) References Cited

OTHER PUBLICATIONS

Jenkins, et al., Transcutaneous Auricular Neurostimulation (tAN): A Novel Adjuvant Treatment in Neonatal Opioid Withdrawal Syndrome, Frontiers in Human Neuroscience, vol. 15, Article 648556, Mar. 8, 2021, pp. 1-12, DOI: 10.3389/fnhum.2021.648556.

U.S. Department of Veterans Affairs, Pain Management Opioid Taper Decision Tool, A VA Clinician's Guide, Oct. 2016, IB 10-939 P96820.

Opioid Oral Morphine Milligram Equivalent (MME) Conversion Factors, Aug. 2017. Available at: https://www.cms.gov/Medicare/Prescription-Drug-coverage/PrescriptionDrugCovContra/Downloads/Opioid-Morphine-EQ-Conversion-Factors-Aug-2017.pdf.

U.S. Department of Health and Human Services, Centers for Disease Control and Prevention, Calculating Total Daily Dose of Opioids for Safer Dosage. Available at: https://www.cdc.gov/drugoverdose/pdf/calculating_total_daily_dose-a.pdf.

Filippelli, et al., Non-insertive Acupuncture and Neonatal Abstinence Syndrome: A Case Series From an Inner-city Safety Net Hospital, Global Advances in Health and Medicine, vol. 1, No. 4, Sep. 2012, pp. 48-52. (Submitted in U.S. Appl. No. 16/846,220).

Raith, et al., Laser Acupuncture as An Adjuvant Therapy for a Neonate with Neonatal Abstinence Syndrome (Nas) Due to Maternal Substitution Therapy: Additional Value of Acupuncture, Acupuncture in Medicine, vol. 32, Issue 6, Dec. 1, 2014, pp. 523-524. (Submitted in U.S. Appl. No. 16/846,220).

Han, et al., Mobilization of Specific Neuropeptides by Peripheral Stimulation of Identified Frequencies, Physiology, vol. 7, Issue 4, Aug. 1, 1992, pp. 176-180. (Submitted in U.S. Appl. No. 16/846,220).

Han, Ji-Sheng, Acupuncture and Endorphins, Neuroscience Letters, No. 361, 2004, pp. 258-261 (Submitted in U.S. Appl. No. 16/846,220).

Meade, et al., A Randomized Trial Of Transcutaneous Electric Acupoint Stimulation As Adjunctive Treatment For Opioid Detoxification, Journal of Substance Abuse Treatment, vol. 38, Issue 1, Jan. 2010, pp. 12-21. (Submitted in U.S. Appl. No. 16/846,220).

Cioca, et al., A Correlation Between GDV And Heart Rate Variability Measures: A New Measure Of Well Being, Measuring Energy Fields: Current Research, 2004, Backbone Publishing Co. Fair Lawn, USA, pp. 59-64. (Submitted in U.S. Appl. No. 16/846,220).

Goldstein, Daniel R., Aging, Imbalanced Inflammation And Viral Infection, Virulence, vol. 1, Issue 4, Jul./Aug. 2010, Landes Bioscience, pp. 295-298. (Submitted in U.S. Appl. No. 16/846,220).

AHRQ Safety Program For Mechanically Ventilated Patients Final Report, Prepared by Johns Hopkins Medicine Armstrong Institute for Patient Safety and Quality, Jan. 2017. (Submitted in U.S. Appl. No. 16/846,220).

Udupa, et al.. Alteration Of Cardiac Autonomic Functions In Patients With Major Depression; A Study Using Heart Rate Variability Measures, Journal of Affective Disorders 100, 2007, pp. 137-141. (Submitted in U.S. Appl. No. 16/846,220).

Freed, et al., Antiviral Innate Immunity: Editorial Overview, Journal of Molecular Biology, vol. 426, Issue 6, Mar. 20, 2014, pp. 1129-1132. (Submitted in U.S. Appl. No. 16/846,220).

Mercante, et al., Aurical Neuromodulation: The Emerging Concept Beyond The Stimulation Of Vagus And Trigeminal Nerves, Medicines, vol. 5, Issue 1, Jan. 21, 2018, article No. 10. (Submitted in U.S. Appl. No. 16/846,220).

Barnes, Peter J., Autonomic Control Of The Lower Airways, Primer on the Autonomic Nervous System (Third Edition), 2012, pp. 201-204. (Submitted in U.S. Appl. No. 16/846,220).

Vaillancourt, et al., Autonomic Nervous System Involvement In Pulmonary Arterial Hypertension, Respiratory Research 18, Dec. 4, 2017, article No. 201. (Submitted in U.S. Appl. No. 16/846,220).

Astrup, et al., Cardiac Autonomic Neuropathy Predicts Cardiovascular Morbidity And Mortality In Type 1 Diabetic Patients With Diabetic Nephropathy, Diabetes Care, vol. 29, Issue 2, Feb. 1, 2006, pp. 334-339. (Submitted in U.S. Appl. No. 16/846,220).

Pavlov, et al., Controlling Inflammation: The Cholinergic Anti-Inflammatory Pathway, Biochemical Society Transactions, vol. 34, Part 6, Oct. 25, 2006, pp. 1037-1040. (Submitted in U.S. Appl. No. 16/846,220).

Mehta, et al., COVID-19: Consider Cytokine Storm Syndromes And Immunosuppression, The Lancet, vol. 395, Bsue 10229, Mar. 16, 2020, pp. 1033-1034. (Submitted in U.S. Appl. No. 16/846,220).

Stebbing, et al., COVID-19: Combining Antiviral And Anti-Inflammatory Treatments, The Lancet Infectious Diseases, vol. 20, No. 4, Feb. 27, 2020, pp. 400-402. (Submitted in U.S. Appl. No. 16/846,220).

Oke, et al., From CNI-1493 To The Immunological Homunculus: Physiology of The Inflammatory Reflex, Journal of Leukocyte Biology, vol. 83, Issue 3, Dec. 7, 2007, pp. 512-517. (Submitted in U.S. Appl. No. 16/846,220).

Boman, Kajsa, Heart Rate Variability A Possible Measure Of Subjective Wellbeing?, University of Skövde Bachelor Degree Project in Cognitive Neuroscience, 2018. (Submitted in U.S. Appl. No. 16/846,220).

Young, et al., Heart-Rate Variability: A Biomarker To Study The Influence Of Nutrition On Physiological And Psychological Health?, Behavioural Pharmacology, vol. 29, Issue 2, Mar. 15, 2018, pp. 140-151. (Submitted in U.S. Appl. No. 16/846,220).

Aguilera, et al., Inflammation As A Modulator Of Host Susceptibility To Pulmonary Influenza, Pneumococcal, And Co-Infections, Frontiers In Immunology, vol. 11, Feb. 11, 2020, article No. 105. (Submitted in U.S. Appl. No. 16/846,220).

Krygier, et al., Mindfulness Meditation, Well-Being, And Heart Rate Variability: A Preliminary Investigation Into The Impact Of Intensive Vipassana Meditation, International Journal of Pyschophysiology, vol. 89, Issue 3, Sep. 2013, pp. 305-313 (Submitted in U.S. Appl. No. 16/846,220).

Cohen, et al., Power Spectrum Analysis And Cardiovascular Morbidity In Anxiety Disorders, Autonomic Neuroscience, vol. 128, Issues 1-2, Jul. 30, 2006, pp. 1-8. (Submitted in U.S. Appl. No. 16/846,220).

De Godoy, et al., Preoperative Nonlinear Behavior In Heart Rate Variability Predicts Morbidity And Mortality After Coronary Artery Bypass Graft Surgery, Medical Science Monitor, vol. 15, Issue 3, Feb. 21, 2009, pp. CR117-CR122. (Submitted in U.S. Appl. No. 16/846,220).

Pavlov, et al., The Cholinergic Anti-Inflammatory Pathway, Brain, Behavior, and Immunity, vol. 19, Issue 6, May 26, 2005, pp. 493-499. (Submitted in U.S. Appl. No. 16/846,220).

Pavlov, et al., The Cholinergic Anti-Inflammatory Pathway: A Missing Link In Neuroimmunomodulation, Molecular Medicine, vol. 9, No. 5-8, Jun. 30, 2003, pp. 125-134. (Submitted in U.S. Appl. No. 16/846,220).

Yamada, et al., The Cholinergic Anti-Inflammatory Pathway: An Innovative Treatment Strategy For Respiratory Diseases And Their Comorbidities, Current Opinion in Pharmacology, vol. 40, Jan. 12, 2018, pp. 18-25. (Submitted in U.S. Appl. No. 16/846,220).

Geisler, et al., The Impact Of Heart Rate Variability On Subjective Well-Being Is Mediated By Emotion Regulation, Personality and Individual Differences, vol. 49, Issue 7, Jul. 9, 2010, pp. 723-728. (Submitted in U.S. Appl. No. 16/846,220).

Seifert, Hilary, The Inflammatory Response Initiated By The Spleen To Ischemic Stroke, University of South Florida Graduate Theses and Dissertations, Jan. 2013. (Submitted in U.S. Appl. No. 16/846,220).

Nuntaphum, et al., Vagus Nerve Stimulation Exerts Cardioprotection Against Myocardial Ischemia/Reperfusion Injury Predominantly Through Its Efferent Vagal Fibers, Basic Research In Cardiology, vol. 113, May 9, 2018, article No. 22. (Submitted in U.S. Appl. No. 16/846,220).

Non-Final Office Action dated Sep. 4, 2019 for U.S. Appl. No. 16/510,930, 13 pages. (Submitted in U.S. Appl. No. 16/846,220).

Notice of Allowance dated Apr. 30, 2020 for U.S. Appl. No. 16/510,930, 13 pages. (Submitted in U.S. Appl. No. 16/846,220).

International Search Report and Written Opinion for International Application No. PCT/US2020/039424 dated Sep. 9, 2020, 15 pages. (Submitted in U.S. Appl. No. 16/846,220).

Non-Final Office Action dated May 15, 2020 for U.S. Application No. 16/846,220, 10 pages.

Notice of Allowance dated Nov. 27, 2020 for U.S. Appl. No. 16/846,220, 7 pages.

(56) References Cited

OTHER PUBLICATIONS

Janes, et al., An Increase in Tobacco Craving Is Associated with Enhanced Medial Prefrontal Cortex Network Coupling, PLOS ONE, vol. 9, Issue 2: e88228, Feb. 2014, pp. 1-5, DOI:10.1371/journal.pone.0088228.

Hayashi, et al., Dorsolateral prefrontal and orbitofrontal cortex interactions during self-control of cigarette craving, Proceedings of the National Academy of Sciences of the United States of America, vol. 110, No. 11, Mar. 12, 2013, pp. 4422-4427, DOI: 10.1073/pnas/1212185110.

Karkhanis, et al., Dynorphin/Kappa Opioid Receptor Signaling in Preclinical Models of Alcohol, Drug, and Food Addiction, International Review of Neurobiology, Jan. 2017, pp. 1-36, DOI: 10.1016/bs.irn.2017.08.001.

Gottfried, et al., Encoding Predictive Reward Value in Human Amygdala and Orbitofrontal Cortex, Science Mag., vol. 301, Issue 5636, Aug. 22, 2003, pp. 1104-1107, DOI: 10.1126/science.1087919.

Alizadehgoradel, et al.. Repeated stimulation of the dorsolateral-prefrontal cortex improves executive dysfunctions and craving in drug addiction: A randomized, double-blind, parallel-group study, Brain Stimulation, vol. 13, Issue 3, Jan. 5, 2020, pp. 582-593, DOI: 10.1016/j.brs.2019.12.028.

Altshuler, et al., Role of orbitofrontal cortex in incubation of oxycodone craving in male rats, Addiction Biology, Jun. 22, 2020, vol. 26, Issue 2, e12927, pp. 1-11, DOI: 10.1111/adb 12927.

Li, et al., The Central Amygdala Nucleus is Critical for Incubation of Methamphetamine Craving, Neuropsychopharmacology, vol. 40, Jan. 7, 2015, pp. 1297-1306, DOI: 10.1038/npp.2014.320.

Childs, et al., Vagus nerve stimulation reduces cocaine seeking and alters plasticity in the extinction network, Cold Spring Harbor Laboratory Press, vol. 24, 2016, pp. 35-42, DOI: 10.1101/lm.043539.116.

Bloom, et al., Neurons containing beta-endorphin in rat brain exist separately from those containing enkephalin: immunocytochemical studies, Proc. Natl. Acad. Sci. USA, vol. 75, No. 3, Mar. 1978, pp. 1591-1595.

Tilbrook, A J, Neuropeptides, Stress-Related, Encyclopedia of stress, vol. 2, 2007, pp. 903-908.

Hutson, et al., Region-Specific Contribution of the Ventral Tegmental Area to Heroin-Induced Conditioned Immunomodulation, Brain Behav Immun., vol. 38, May 2014, pp. 118-124, DOI: 10.1016/j.bbi.2014.01.008.

Veening, Jan G., and Barendregt, Henk P., The effects of Beta-Endorphin: state change modification, Fluids and Barriers of the CNS, 12:3, Jan. 2015, pp. 1-22, DOI: 10.1186/2045-118-12-3.

Eisenstein, Toby K., The Role of Opioid Receptors in Immune System Function, Frontiers in Immunology, vol. 10, Article 2904, Dec. 20, 2019, DOI: 10.3389/fimmu.2019.02904.

Veening, et al., Volume transmission of beta-endorphin via the cerebrospinal fluid; a review, Fluids and Barriers of the CNS, 9:16, Aug. 2012, pp. 1-16, DOI:10.1186/2045-8118-9-16.

Chiluwal, et al., "Neuroprotective Effects Of Trigeminal Nerve Stimulation In Severe Traumatic Brain Injury, Scientific Reports," vol. 7, Jul. 28, 2017, article No. 6792.

* cited by examiner

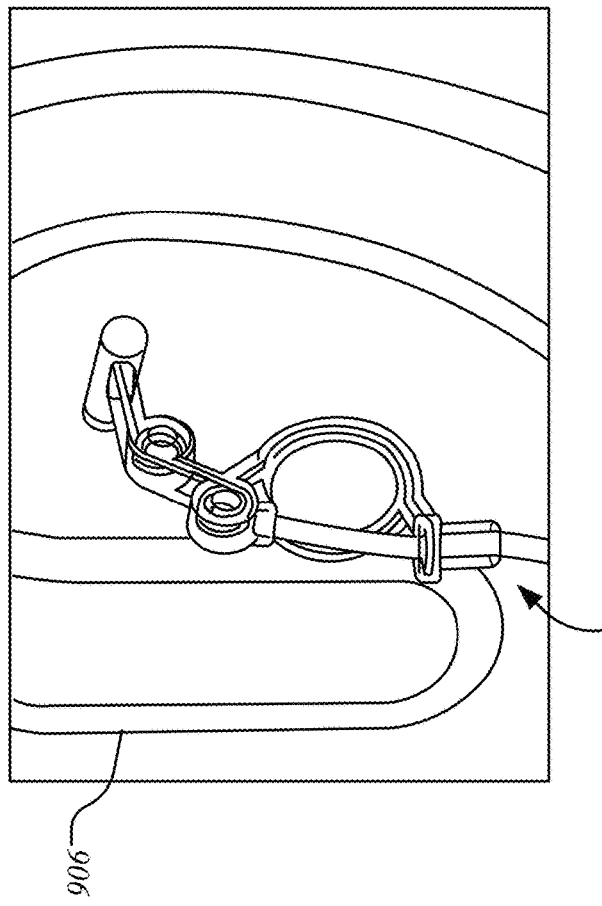
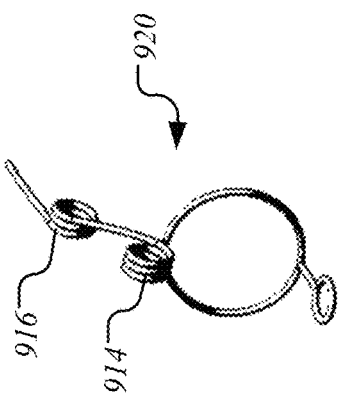
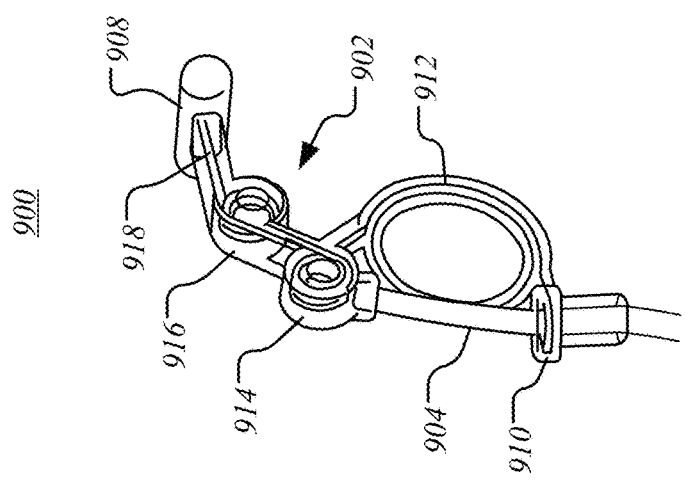
FIG. 9B
FIG. 9C
FIG. 9A

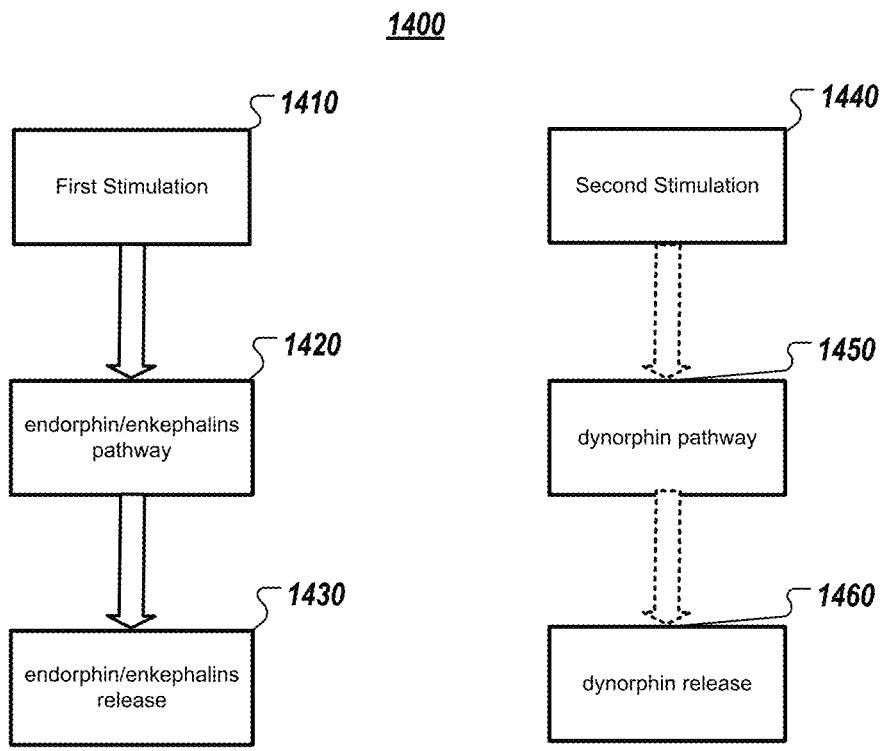
FIG. 14A
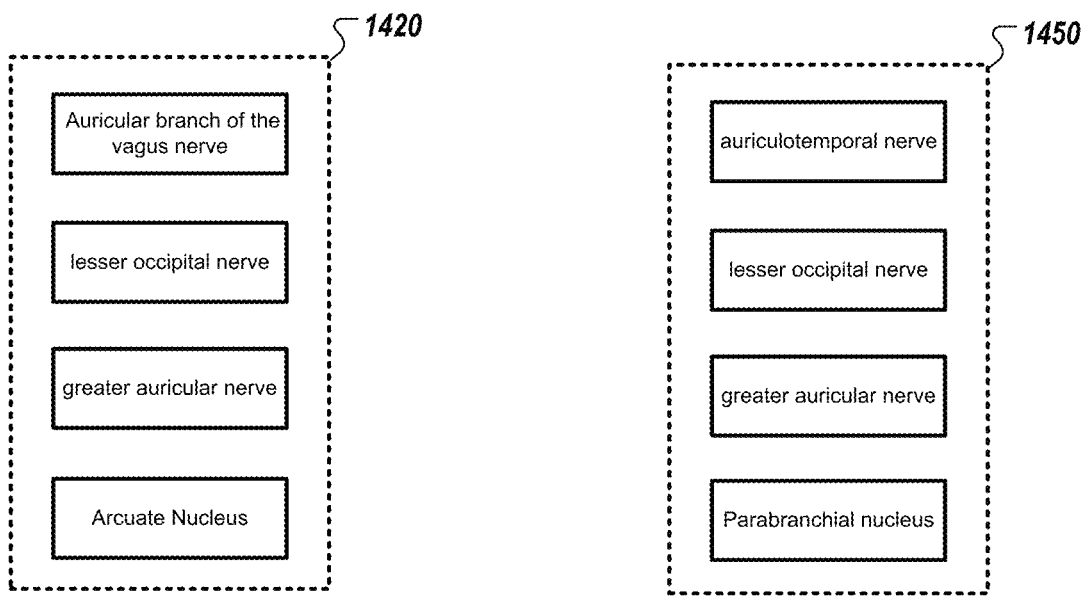
FIG. 14B
FIG. 14C

DEVICES AND METHODS FOR TREATING COGNITIVE DYSFUNCTION AND DEPRESSION USING ELECTRICAL STIMULATION

CROSS-REFERENCE TO RELATED APPLICATIONS

This application is a continuation-in-part of, and claims priority to, U.S. patent application Ser. No. 16/846,220 entitled "Devices and Methods for Reducing Inflammation Using Electrical Stimulation," filed Apr. 10, 2020, which is a continuation-in-part of, and claims priority to, U.S. patent application Ser. No. 16/510,930 entitled "Device and Method for the Treatment of Substance Use Disorders," filed Jul. 14, 2019 (now U.S. Pat. No. 10,695,568) which claims priority to U.S. Provisional Patent Application Ser. No. 62/777,569, entitled "Device and Method for the Treatment of Substance Use Disorders," filed Dec. 10, 2018. All above identified applications are hereby incorporated by reference in their entireties.

BACKGROUND

Depression is a common mental condition affecting more than 250 million people worldwide. As such, depression is one of the leading causes of disability. Moreover, in extreme cases depression can lead to suicide which, with 800,000 yearly global cases, is the second leading cause of death in the 15 to 29 age group. The National Institute of Mental Health has estimated that 6.7% of all adults in the US, or approximately 16.2 million American adults, had at least one major depressive episode in 2016.

Depression shares common neuronal pathways in the brain stem with other pathologies that interact with neural networks which modulate the production and release of endogenous opioids (Endogenous Opioid Circuits—EOC), such as, in some examples, pain, addiction, and post-traumatic stress disorder (PTSD).

SUMMARY OF ILLUSTRATIVE EMBODIMENTS

Currently, the United States is experiencing an opioid epidemic in the use of prescription and non-prescription drugs that has continued to rise since the 1990's. The need for safe and effective opioid withdrawal treatment is demanding and largely unmet. According to the National Survey on Drug Use and Health (NSDUH), approximately 2.1 million Americans are addicted to opioid pain relievers (OPRs), and 513,000 are addicted to heroin. In 2005, there were an estimated 10 million chronic pain patients receiving daily, long-term treatment with OPRs. The continuing increase in opioid consumption from 2005 to 2017 suggests that the number may now exceed 11 million.

A primary constraint on the overall percentage of treatment recipients is the limited availability of licensed physicians that can prescribe pharmacotherapies. Additionally, prescription opioids pose a variable level of risk on respiratory depression and abnormal cardiac activity, thus can only be obtained from licensed opioid treatment programs (OTPs). The lack of OTPs in many communities presents a major challenge to expanding access to methadone. In contrast, buprenorphine, a partial opioid agonist, has demonstrated a better safety profile compared to methadone and can be prescribed in an office-based setting. However, buprenorphine includes federal limits on the number of patients a physician may treat, ineligibility of nurse practitioners to prescribe it, and inadequate integration of buprenorphine into primary care treatment.

Pharmacotherapies for opioid withdrawal include full-agonist treatment with methadone, partial-agonist with buprenorphine, and full-antagonist with naltrexone. Methadone and buprenorphine are semi-synthetic opioid derivatives that bind to opioid receptors and allow addicted individuals to discontinue the misuse of opioids without experiencing withdrawal symptoms. Buprenorphine can produce typical opioid effects and side effects such as euphoria and respiratory depression, however, its maximal effects are less than those of full agonists like methadone or heroin. Dose response curves specific to the agonist effects of buprenorphine increase linearly with higher doses of the drug until it reaches a plateau.

Buprenorphine can block the effects of full opioid agonists (i.e. methadone and heroin) and can precipitate withdrawal symptoms if administered to an opioid-addicted individual while a full agonist is in the bloodstream. Buprenorphine has a higher affinity than other opioids and as such will compete for the receptor and occupy that receptor blocking other opioids from binding. If there is an insufficient amount of buprenorphine to occupy and satisfy the receptors, withdrawal symptoms can occur; in which case additional buprenorphine is given until withdrawal symptoms disappear.

Lastly, naltrexone is an opioid-antagonist that competes for opioid-receptors and displaces opioid drugs from these receptors, thus reversing the effects of opioids. Naltrexone is capable of antagonizing all opioid receptors, but has a higher affinity to $\mu$-rather than $\kappa$- and $\delta$-receptors. By blocking the $\mu$-opioid receptor, naltrexone acts to decrease the dopamine reward. The activity of naltrexone is thought to be a result of both the parent and its 6$\beta$-naltrexol metabolite. Naltrexone's mechanism of action is similar to naloxone (opioid antagonist; found in Suboxone) except that it is longer acting. Naltrexone can be administered with a long-acting injection formulated in microspheres that persists for 1 month after a single injection.

Due to inadequate and scarce treatment options, finding an effective non-pharmacological approach would be critical in improving and expanding treatment for opioid withdrawal and addiction. Evidence exists for the rapid and effective attenuation of signs and symptoms associated with opioid withdrawal through neurostimulation.

Percutaneous neurostimulation requires a percutaneous device which uses small needles implanted into the skin to deliver neurostimulation. Percutaneous neurostimulation systems present numerous disadvantages and limitations, which include: the location of the needles is critical and thus needle insertion must be performed by a trained professional heath provider; the needles must be sterile; needle sterility requirements equate to a minimal device shelf-life; movement or dislodged needles requires the attention of a trained clinic staff member; many patients have inherent fear of needles; currently available systems cannot be re-used, re-charged, or used beyond its immediate battery life; currently available systems do not allow for fully customizable stimulation settings; currently available systems are not capable of determining and reporting if stimulation is being delivered; currently available systems are not capable of gathering device compliance data; and currently available systems are not designed to be easy to use, aesthetically and cosmetically appealing which has an effect on patient compliance.

Furthermore, patient compliance is one of the primary obstacles to clinical success, the proposed device has been designed to alert the treating clinic staff when the device is not being used as prescribed, including device malfunction, and electrode misplacement. Since the novel devices and therapy solutions described herein can be used long-term and can be easily applied by the user, the novel therapy/device combination lends itself to be used for consumption reduction, consumption secession, and long-term use avoidance.

In an aspect, the present disclosure relates to transcutaneous stimulation of auricular nerve fibers for the reduction of substance consumption, the reduction of symptoms associated with substance withdrawal, and for the long-term maintenance to prevent substance relapse. The proposed novel neuromodulation treatment does not require piercing the dermal layers and the required precision is such that any layman can apply the device and receive therapy. In an aspect, the system is not required to be sterile, is easy to apply, and a user can apply without a clinician. The proposed treatment method along with the treatment device overcomes all of the above-mentioned disadvantages. Given the large unmet medical need (i.e., opioid overuse), the fact that the treatment device proposed here has not been offered in the manner here proposed points to the non-obviousness nature of the proposed treatment.

In some implementations, the treatment device can be used for treating and/or managing symptoms for other indications. In some implementations, the treatment device can be used to provide therapy for the treatment of neonatal abstinence syndrome by transcutaneous stimulation of auricular nerve fibers. Auricular acupuncture has recently been studied as an adjunctive therapy for neonatal abstinence syndrome in newborns. Non-insertive acupuncture (NIA) using traditional needles as shown in a publication by Filippelli, A. C. et. al. (2012). titled "Non-insertive Acupuncture and Neonatal Abstinence Syndrome: A Case Series From an Inner-city Safety Net Hospital. Global Advances in Health and Medicine," published in Global Advances in Health and Medicine, 48-52. 2012, herein incorporated by reference.

Evidence that the treatment device can be used to provide therapy for the treatment of neonatal abstinence syndrome was provided in a study where a handheld laser was applied to the ear of newborns with neonatal abstinence syndrome resulting in some of the babies becoming more relaxed during their course of treatment, as described in Raith, W., & Urlesberger, B. titled "Laser Acupuncture as An Adjuvant Therapy for a Neonate with Neonatal Abstinence Syndrome (NAS) Due to Maternal Substitution Therapy: Additional Value of Acupuncture," published in Acupuncture in Medicine, 2012, 32(6), 523-524 herein incorporated by reference. While more in-depth studies are needed to evaluate Non-insertive acupuncture as an effective adjunct therapy for neonatal abstinence syndrome in newborns, the early results show promise of tapping into the auricular neural pathways for treating neonatal abstinence syndrome.

Therapy systems and methods are provided for rapidly releasing endogenously produced opioid receptor agonists. The therapy system, in some implementations, includes a treatment device that allows the proposed therapy to be easily and reliably applied by almost anyone at a relatively low cost. Some advantages over the existing neuromodulation treatment and related devices are: ease of use in both the application of the device, customizing therapeutic settings, and the actual wearing of the device, minimal risk of infection, users have the ability to safely self-administer or restart the treatment without the need to go back to a clinic, significantly extended shelf life, reduced anxiety of patient due to non-invasiveness, long-term use option, customizable therapeutic settings, ability to notify user, caregiver, and clinician if therapy is interrupted or halted, ability to report overall usage to clinical staff or users for analysis, and the user does not have go back to the clinic to extend treatment or to use it at any given time when they feel it is needed present a major advantage over existing neuromodulation therapies, opening the door to a long-term maintenance treatment.

In an aspect, the therapy device is configured to provide stimulation therapy to release a different type and quantity of endogenous opioid peptides based on varying stimulation parameters. Three families of endogenous opioid peptides have been characterized in the CNS: enkephalins, endorphins, and dynorphins. Supporting animal data was shown in a study examining effects of different stimulation frequencies on the type and quantity of endogenous opioid peptides released, as described in a publication by Han, J. S., and Wang, Q. titled "Mobilization of specific neuropeptides by peripheral stimulation of identified frequencies," in Physiology 1992, 7(4), 176-180, herein incorporated by reference. Electro-acupuncture (EA) stimulation was delivered at two specific acupoints on the hindlimb. Rats were given stimulation at 2, 15, and 100 Hz. Spinal perfusate was collected before and during stimulation. A clear difference in stimulation frequency and type of opioid peptide release were shown including that 2 Hz was effective at releasing enkephalins and beta-endorphins, and 100 Hz most effectively released dynorphin. No increase in opioid peptides was observed in non-responder rats that failed to show a response to tail-flick during stimulation. Although, 15 Hz was capable of releasing enkephalin and dynorphin opioid peptides, another study shows that alternating stimulation at 2 Hz/100 Hz maximized analgesic effects, the study by Han, J. S. titled "Acupuncture and endorphins," published in Neuroscience letters, 2004, 361 (1-3), 258-261 is herein incorporated by reference. The scientific evidence that pain-relief is achieved by delivering neurostimulation to release endogenous opioid peptides and fill vacant opioid receptors, was later a tested hypothesis for reducing the symptoms associated with opioid withdrawal.

In a randomized clinical trial, transcutaneous electrical acupoint stimulation (TEAS) was delivered as an adjuvant to opioid detoxification using buprenorphine-naloxone, the clinical trial as reported by Meade, C. S., et al., titled "A randomized trial of transcutaneous electric acupoint stimulation as adjunctive treatment for opioid detoxification, Journal of Substance Abuse Treatment, 2010, 38(1), 12-21, is herein incorporated by reference. Based on the preclinical evidence described above, TEAS was delivered at alternating low (2 Hz) and high (100 Hz) for 30 minutes each day for 3-4 days. In the active TEAS group, patients were 77% less likely to have used any drugs as compared to 33% in sham treatment at 2-weeks post-discharge. Additionally, active TEAS improved pain perception and overall health.

In a preferred embodiment, a therapy system includes a treatment device having an auricular component configured to be in contact with a patient and a pulse generator or controller configured to communicate with the treatment device. In some implementations, a treatment device can be provided as an assembled unit or as several pieces configured for connection prior to use. In an example, the auricular component can be provided in a sealed pouch and a pulse generator can be provided to connect the auricular component to a connector on the pulse generator. In an aspect, the system is configured to have a removable stimulator without the need to remove the auricular component and vice-versa. In an example, the earpiece can be placed around the auricle of the patient before or after connection to the pulse generator.

In some implementations, the treatment device can be used to provide therapy including a first stimulation configured to stimulate pathways modulating dynorphins release and a second stimulation configured to stimulate pathways modulating endorphins release. In some implementations, the treatment device can be used to provide therapy including a first stimulation configured to stimulate pathways modulating dynorphins release and a second stimulation configured to stimulate pathways modulating enkephalins release. In other implementations, the treatment device can be used to provide therapy including a first stimulation configured to stimulate pathways modulating dynorphins release and a second stimulation configured to stimulate pathways modulating enkephalins and endorphins release.

In an example, the first stimulation can be a high frequency stimulation and the second stimulation can be a low frequency. In an example, the pathways modulating dynorphins release can include at least one of the auriculotemporal nerve, the lesser occipital nerve, and the great auricular nerve. In an example, the pathways modulating dynorphins release can include stimulation of dynorphin pathway via stimulation of the Parabrachial nucleus. In an example, the pathways modulating endorphins and enkephalins release can include at least one of the auricular branches of the vagus nerve, the lesser occipital nerve, and the great auricular nerve. In an example, the pathways modulating endorphins and enkephalins release can include stimulation of endorphins and enkephalins pathway via stimulation of the Arcuate nucleus of the hypothalamus.

To provide the therapy, a provider may adjust therapy parameters as needed and start the therapy using the controls on either the pulse generator or the peripheral device. In some implementations, the therapy includes providing two or more simultaneous and/or synchronized stimulations. In an aspect, the therapy can involve applying a first stimulation having a first set of parameters at a first portion of the patient's skin and applying a second stimulation having a second set of parameters at a second portion of the patient's skin. When therapy is done, the user may remove the earpiece and disconnect the earpiece from the pulse generator. In an example, the used earpiece can be replaced with a new earpiece for the next session.

In some embodiments, treatment can be applied unilaterally (left or right) and yet in other embodiments a bilateral treatment may be applied. In the case of a bilateral application two devices could be used; these two devices could be synchronized for yet a better systemic response. A single device with more channels or a single device multiplexing the outputs could also be used for a bilateral application.

The forgoing general description of the illustrative implementations and the following detailed description thereof are merely exemplary aspects of the teachings of this disclosure, and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings:

FIGS. 9A-9C are drawings of a compression-loaded component configured to facilitate placement of the cymba electrode according to an example;

FIG. 14A is a flow chart of a method for providing therapy including providing a first stimulation at a first tissue location configured to stimulate a first pathway for modulating a first release of a first endogenous peptide and a second stimulation at a second tissue location configured to stimulate a second pathway for modulating a second release of a second endogenous peptide according to an example;

FIG. 14B are examples of target locations for stimulation of the first tissue location;

FIG. 14C are examples of target locations for stimulation of the second tissue location;

DETAILED DESCRIPTION OF ILLUSTRATIVE EMBODIMENTS

Figure 1A:
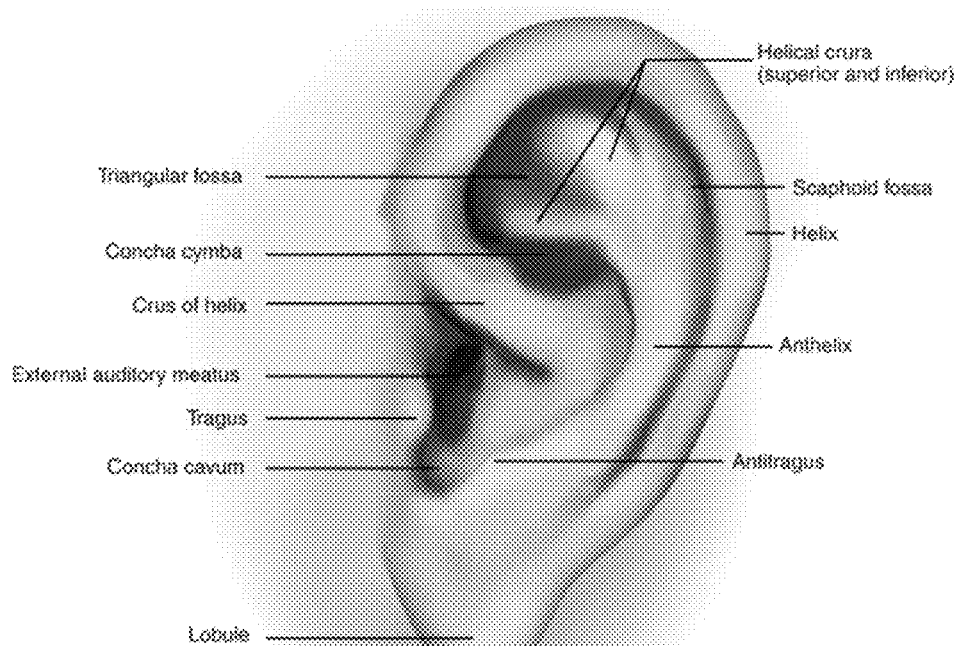
FIG. 1A is a drawing identifying structures of an ear according to an example.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

In some implementations, treatment systems, devices, and methods for stimulation of neural structures on and surrounding a patient's ear are designed for providing stimulation without piercing the dermal layers on or surrounding the ear. The stimulation, for example, may induce endogenous release of peptides, such as endorphins. Electrodes may be frictionally and/or adhesively retained against the skin on and surrounding the patient's ear to target various nerve structures. The electrodes may have a substantial surface area in comparison to prior art systems relying upon dermal-piercing electrodes, such that multiple nerve terminals are stimulated by a single electrode during therapy. For example, a number of nerve terminals may be situated directly beneath and/or beneath and closely adjacent to the skin upon which the electrode is positioned. By targeting multiple nerve terminals, in some embodiments, positioning of each electrode does not necessarily need to be precise. Therefore, for example, a patient or caregiver may be able to apply and remove the device as desired/needed (e.g., for sleeping, showering, etc.). Further, targeting multiple nerve terminals is advantageous since stimulating multiple branches of a nerve elicits a stronger response than stimulating a single branch, which is the case when using pinpoint electrodes such as needle electrodes.

Figure 1B:
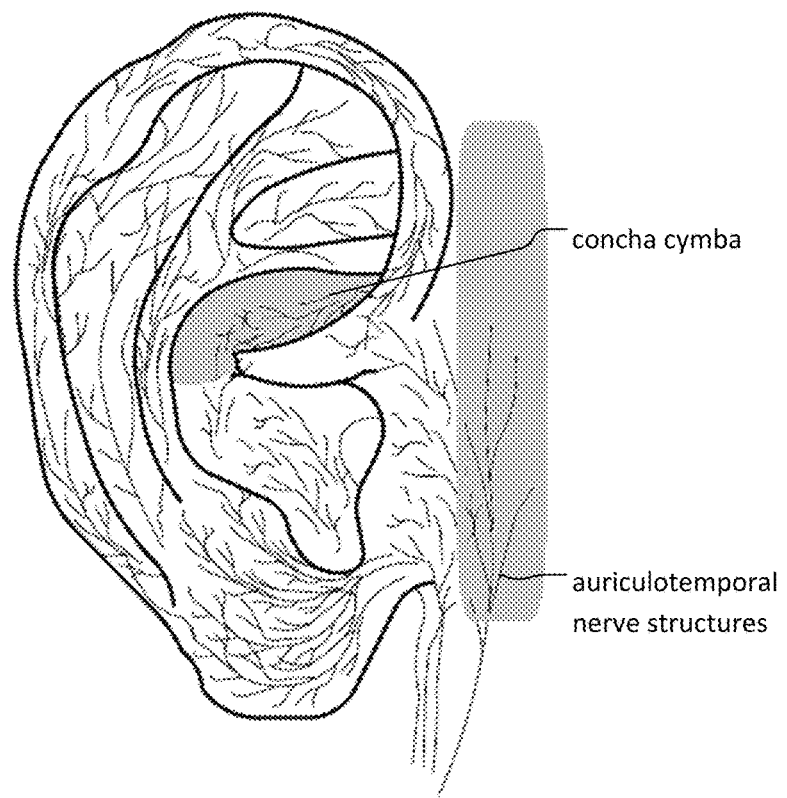
FIG. 1B is a drawing of innervations of the ear amongst which are vagal related neural structures, auriculotemporal nerve structures, neural structures related to the lesser occipital nerve, and neural structures related to the great auricular nerve.
Figure 1C:
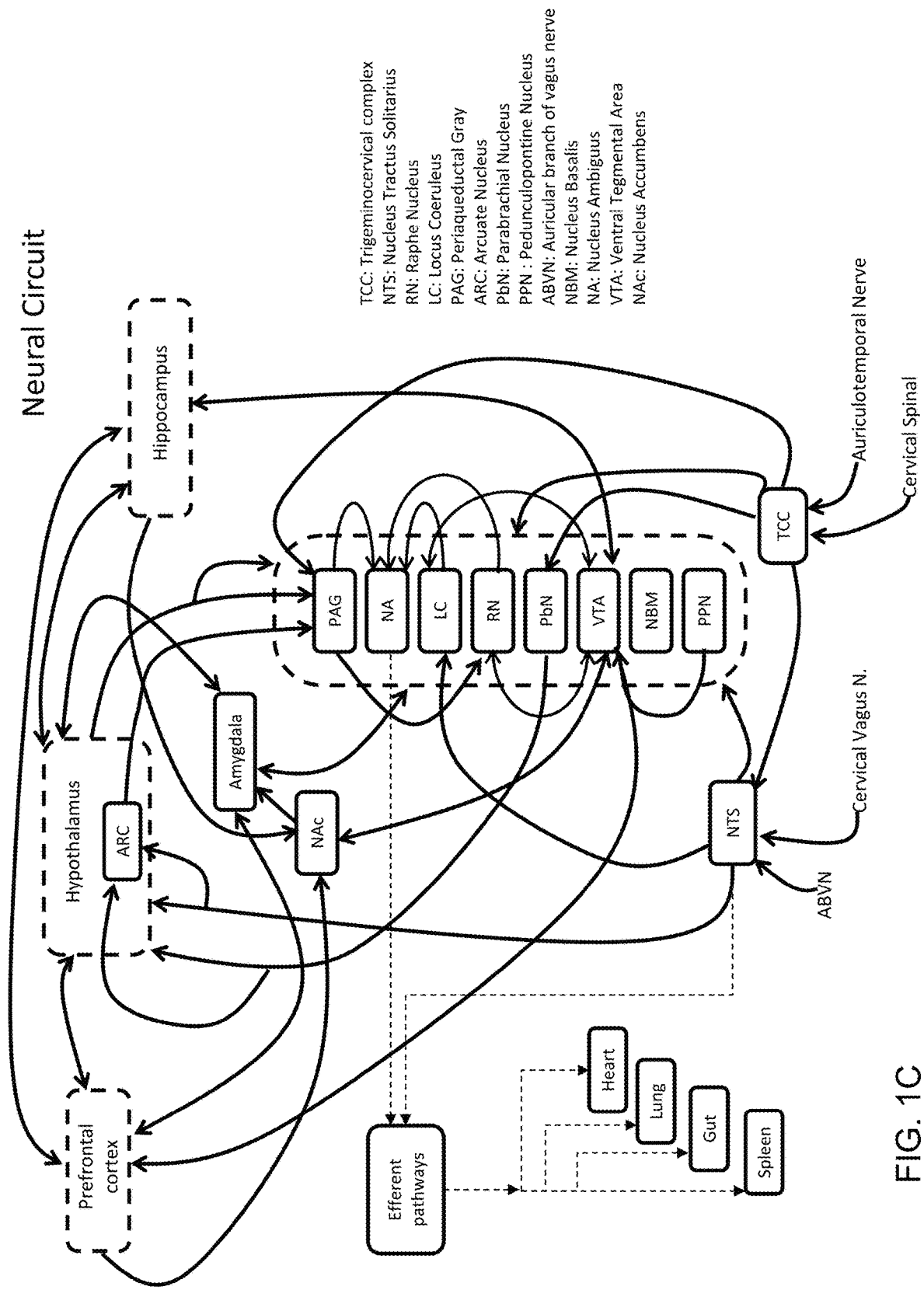
FIGS. 1C-1G are drawings identifying neural structures and pathways for modulating the release of endogenous opiate receptor agonist, which modulate pain, as well as pathways modulating anti-inflammatory, pulmonary, and cognitive processes to an example.
Figure 1D:
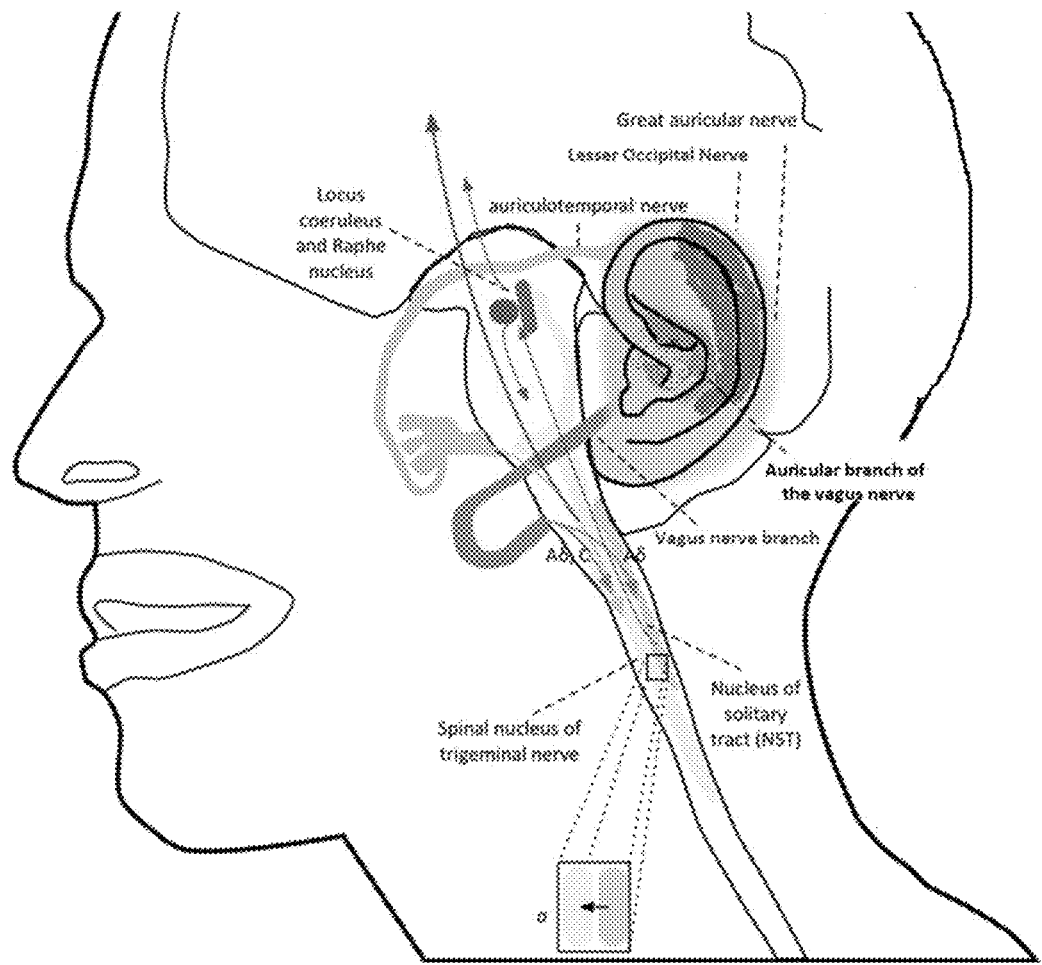
Figure 1E:
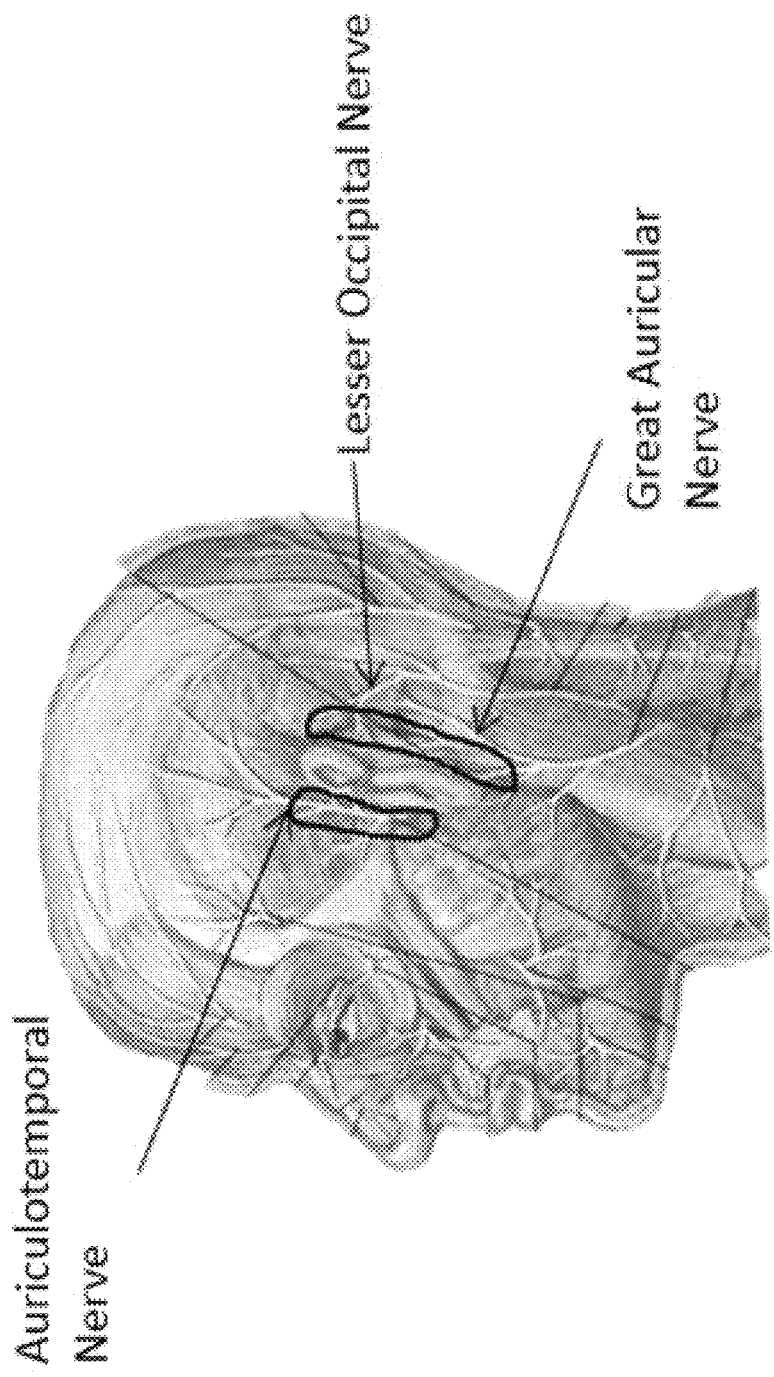

The transdermal stimulation of these nerve regions enables a variety of beneficial treatments. In some examples, these include the treatment of acute or chronic pain, inflammatory conditions, and cognitive difficulties. FIGS. 1C-1E are drawings identifying neural structures and pathways for modulating the release of endogenous opioid receptor agonist, which modulates pain, as well as pathways modulating inflammatory and cognitive processes. The Nucleus of the solitary tract (NTS) receives afferent connections from many areas including the Trigemino-cervical complex (TCC), the cervical vagus nerve as well as from the auricular branch of the vagus nerve (ABVN). The TCC is a region in the cervical and brain stem area were trigeminal and occipital fibers synapse, including the Auriculotemporal nerve, the lesser occipital nerve and the greater auricular nerve. The TCC projects to multiple areas in the brain stem including, but not limited to the Nucleus Raphe Magnus (NRM) and other parts of the Raphe nuclei (e.g., Raphe Nucleus (RN)), the Locus Coeruleus (LC), Periaqueductal Gray (PAG), Nucleus Basalis (NBM), the Nucleus Ambiguus (NA), the Ventral Tegmental Area (VTA), the Nucleus Accumbens (NAc) and Parabrachial nucleus (PbN). The NTS among others, also projects to the RN (e.g., NRM), the LC, and the PAG as well as to high centers like the hypothalamus, including into the Arcuate Nucleus (ARC) which receives its majority of non-intrahypothalamic afferents from the NTS. Additionally, many interconnections exist amongst different brainstem nuclei (e.g., PAG, LC, RN, NRM, NBM, PbN, PPN, NA, VTA, NAc); for example, the LC, PAG, and RN (e.g., NRM) project to the NA, and the PPN projects into the VTA. The VTA, in turn, projects to the Prefrontal Cortex, being interconnected with the hypothalamus and the hippocampus. The VTA projects directly to the Hippocampus as well. The Hippocampus, in turn, projects to the NAc and interconnects with the hypothalamus.

The following table presents a listing of opioid receptors in the central nervous system:

TABLE 1

| Receptor | Expression/Distribution | Cell Types | Endogenous Ligands |
|---|---|---|---|
| MOR | Amygdala, thalamus, periaqueductal gray, locus coeruleus, raphe magnus, mesencephalon, habenula, hippocampus, some brainstem nuclei | GABAergic Glutamatergic | β-endorphin (High) enkephalins (Med) Dynorphin (Low) |
| KOR | Basal anterior forebrain, olfactory tubercle, striatum (caudate putamen and NAc), preoptic area, hypothalamus, pituitary | Dopaminergic Glutamatergic GABAergic | Dynorphin (High) β-endorphin (Low) enkephalins (Low) |
| DOR | Olfactory tract, cortices, including whole neocortex and regions of the amygdala that derive from the cortex (basolateral, cortical, and median nuclei of the amygdala), striatum | GABAergic Dopaminergic | β-endorphin (High) enkephalins (High) Dynorphin (Low) |
| NOP | Periaqueductal gray, thalamic nuclei, somatosensory cortex, rostral ventral medulla, spinal cord, dorsal root ganglia, VTA, NAc, PFC, central amygdala, lateral hypothalamus | Dopaminergic | OrphaninFQ/ nociceptin (High) |

MOR/KOR/DOR = μ/κ/δ -opioid receptor; NOP = nociception/orphanin FQ receptor; NAc = nucleus accumbens; PFC = prefrontal cortex; VTA = ventral tegmental area. Affinity in presented in parenthesis.

These connections make this neural circuit extremely important for modulating pain, as production of endorphins, enkephalins, and dynorphins are modulated by this circuit. In addition, this neural circuits are crucial for learning and memory as well as for arousal and wakefulness. For example, an interaction between norepinephrine, produced by activity in the Locus Coeruleus (LC), Serotonin (5-HT), produced by activity in the RN (e.g., NRM), and Acetylcholine (ACh) produced by activity in the Pedunculopontine Nucleus (PPN) or NBM is extremely important for memory and learning. Arousal and wakefulness are modulated, amongst others, by norepinephrine in the brain.

There are descending indirect connections going to the heart, lungs, gut, and spleen. Indirect connections include connections where there is at least one synapse elsewhere before reaching the target. This means that modulating the activity of these neural circuits can affect the respective organs. In particular, heart rate can be modulated (e.g., heart rate can be decreased and heart rate variability can be increased); oxygen absorption can be increased at the lungs by increasing the compliance of the bronchi tissue and thus increasing the oxygen transport availability therefore increasing the potential for more oxygen to be absorbed into the blood; gut motility can be increased by descending pathways originating in the dorsal motor nucleus of the vagus nerve (DMV); since DMV activity is modulated by NTS activity, motility in the gut can be affected by modulating the activity in the NTS; and a decrease in circulating pro-inflammatory cytokines can be achieved by modulating spleen activity via NTS descending pathways.

Heart rate variability (HRV) is a reflection of the state of the autonomic nervous system (ANS). The sympathetic branch of the ANS, which is more active during stress situations tends to increase heart rate (HR) and decrease HRV; the opposite is true for the parasympathetic branch of the ANS, which tend to decrease HR and increase HRV. Higher HRV has been associated with morbidity and mortality in several conditions as well as with well-being and has been used as a health biomarker.

There are at least three different opioid receptors, Mu (μ), Delta (δ), and Kappa (κ) in pain modulation. The body produces endogenous agonist peptides for each of these three receptors. These peptides are called endorphins, which primarily binds to the Mu (μ) receptors, Enkephalin which primarily binds to the Delta (δ) receptors, and Dynorphins, which primarily binds to the Kappa (κ) receptors. Pain studies suggest that production of these endogenous peptides follow different pathways. While production of endorphins and enkephalin is mediated by activity in the Arcuate Nucleus (ARC) in the hypothalamus, activity in the Parabrachial nucleus mediates production of dynorphins. Furthermore, electrostimulation experiment showed that dynorphin production was more efficiently mediated by higher frequency than production of the endorphins and/or enkephalins; this suggests that while the dynorphin pathway is more efficiently activated by higher frequencies, the endorphins and enkephalins pathway is more efficiently activated by lower frequencies.

In some implementations, the treatment device can be used to induce neuronal plasticity or Neuroplasticity for provoking cognitive improvements, stroke recovery, PTSD, phobias, ADHD, ADD, dementia including treating Alzheimer's disease. Neuroplasticity underlies learning; therefore, strategies that enhance neuroplasticity during training have the potential to greatly accelerate learning rates. Earlier studies have successfully demonstrated that invasive or implanted vagus nerve stimulation (VNS) can drive robust, specific neural plasticity. Brief bursts of VNS are paired with training to engage pro-plasticity neuromodulatory circuits and reinforce the specific neural networks that are involved in learning. This precise control of neuroplasticity, coupled with the flexibility to be paired with virtually any training paradigm, establishes VNS as a potential targeted neuroplasticity training paradigm.

The vagus nerve is a cranial nerve that is located adjacent to the carotid artery in the neck. Direct stimulation of the vagus nerve activates the nucleus tractus solitarius (NTS), which has projections to nucleus basalis (NBM) and locus coeruleus (LC). The NBM and LC are deep brain structures that release acetylcholine and norepinephrine, which are pro-plasticity neurotransmitters important for learning and memory. Stimulation of the vagus nerve using a chronically implanted electrode cuff is safely used in humans to treat epilepsy and depression and has shown success in clinical trials for tinnitus and motor impairments after stroke. The auricular branch of the vagus nerve innervates the dermatome region of outer ear, being the region known as the cymba conchae one of the areas innervated by it. Noninvasive stimulation of the left auricular branch of the vagus nerve may drive activity in similar brain regions as invasive vagus nerve stimulation. Recently auricular neurostimulation has proven beneficial in treating a number of human disorders.

In some implementations, the treatment device can be used to restore autonomic balance such as cardiac heart failure, atrial fibrillation (AF), anxiety, stress, gastric motility, depression, cluster headaches, and migraines. Transcutaneous electrical stimulation of the tragus (e.g., the anterior protuberance of the outer ear), which is partly enervated by the auricular branch of the vagus nerve, can elicit evoked potentials in the brainstem in human subjects. Based on these observations, it was demonstrated that atrial fibrillation inducibility was suppressed by transcutaneous low level-VNS stimulation, which was achieved through stimulation of the auricular branch of the vagus nerve at the tragus in a canine. Noninvasive transcutaneous low level-VNS stimulation increases AF threshold (mitigates risk of AF), as well as alleviates AF burden in both canines and humans. In healthy subjects, transcutaneous low level-VNS stimulation can also increase heart rate variability and reduce sympathetic outflow.

In some implementations, the treatment device is used to reduce inflammation caused by viral or bacterial infections. In the initial stages of infection, the body response includes the secretion of pro-inflammatory cytokines. In some cases, controlling this inflammatory response such that it can be reduced can help the body to heal faster. Inflammatory responses are a double-edged sword in the sense that it is necessary to eradicate cells infected by viruses as well as bacteria. However, an excessive pro-inflammatory response can actually lead to death. In particular in respiratory infections, pro-inflammatory cytokines may lead to an increase in pathogen replication. In addition, lung function may be compromised by the accumulation of pro-inflammatory cytokines. Studies suggest that the pro-inflammatory response in some individuals (e.g., older people) is often excessive. In many of these cases, it is this pro-inflammatory response that causes more harm than the infection itself resulting in the potential death of the infected subject. In response to Coronavirus Disease 2019 (COVID-19) and Severe Acute Respiratory Syndrome (SARS), for example, the human body produces an excessive pro-inflammatory response. In fact, evidence gathered so far suggests that in some individuals with severe COVID-19 the body responds by unleashing an exacerbated release of pro-inflammatory cytokines. Reducing the inflammatory response, e.g., through reducing circulating pro inflammatory cytokines, will, in some cases, reduce the time to heal and/or will reduce the time an infected person may need to use assistive respiratory therapy such as the need for a ventilator. In general, a patient stays on average less than 5 days on a ventilator; however, in the case of COVID-19, patients have been remaining on ventilators for as much as 3 or 4 times longer; i.e., 15 to 20 days. Healthcare centers are generally equipped with enough ventilators to serve a population that will need them in average less than 5 days. The increase in the time a ventilator is needed in COVID-19 patients is a factor in the overall mortality rate seen in COVID-19 since many patients in need of a ventilator will not have access to one. Via modulation of NTS activity, treatment devices and methods described herein can not only a) increase the compliance of the bronchi tissue ultimately providing more oxygen to the body but also, b) decrease inflammation in the lungs. For example, modulation of NTS activity can decrease the amount of circulating pro inflammatory cytokines. These two effects allow the novel treatment devices and methods described herein to behave as an adjuvant therapy in the treatment of respiratory infections (e.g., Middle East respiratory syndrome coronavirus (MERS), severe acute respiratory syndrome (SARS), COVID-19, or chronic obstructive pulmonary disease (COPD)).

Figure 1G:
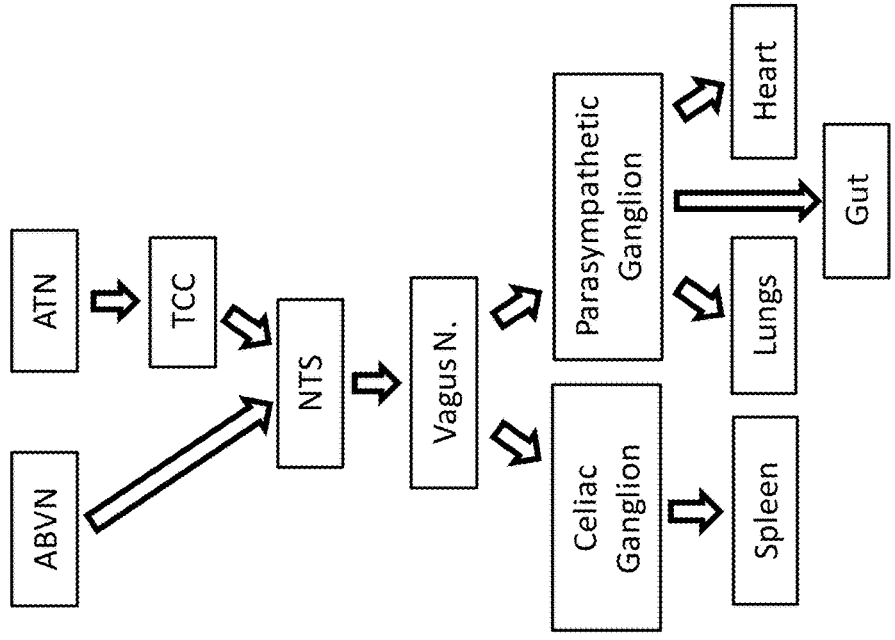
Figure 1F:
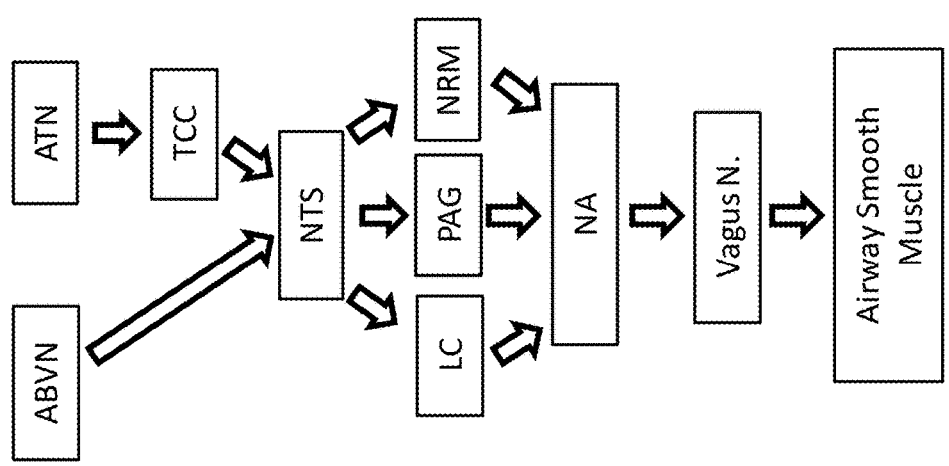

The compliance of the bronchi is produced via the modulation of the Autonomic Pulmonary Pathway, illustrated in FIG. 1F. In particular, the novel treatment presented herein stimulates the ABVN and/or the auriculotemporal nerve (ATN) which have projections to the NTS. The NTS projects to LC, PAG and RN (e.g., NRM). These brainstem nuclei deliver an inhibitory signal to airway-related pre-ganglionic neurons located in the nucleus ambiguus (NA). The NA sends a signal to the airway smooth muscle, via efferent pathways mainly through the vagus nerve, eliciting bronchodilation.

The anti-inflammatory effect is provided via activation of the Anti-inflammatory Pathway (a.k.a. the cholinergic anti-inflammatory pathway), as illustrated in FIG. 1G. In particular, the novel treatment described herein stimulates the ABVN and/or the ATN which, as stated before, have projections to the NTS; these projections elicit cholinergic anti-inflammatory effects via efferent pathways; mostly via the vagus nerve. Systemic anti-inflammatory effects occur when the vagus nerve mediates spleen function, thereby reducing the amount of circulating pro-inflammatory cytokines. In addition, a local anti-inflammatory effect occurs at organs reached by the efferent pathways; for example at the lungs, gut, and heart.

To stimulate the various neural structures discussed above, in some implementations, treatment devices may be designed for positioning against various surfaces on or surrounding a patient's ear. FIG. 1A is a drawing identifying structures of an ear showing amongst other the concha cymba, the tragus, the antihelix, the helix, the external auditory meatus, and the Lobule. FIG. 1B is a drawing of innervations of the ear amongst which are vagal related neural structures, for example within the concha cymba, auriculotemporal nerve structures, for example rostral to the auricle. In FIG. 1E, neural structures related to the lesser occipital nerve and neural structures related to the great auricular nerve are shown, for example behind the auricle.

Figure 2A:
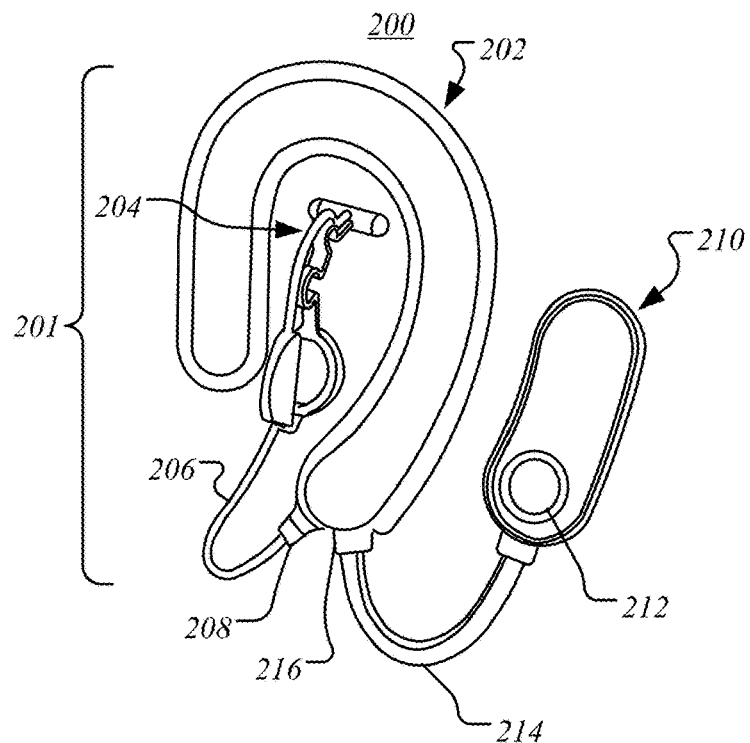
FIG. 2A is a drawing of a treatment device including an auricular component having an earpiece connected to a concha apparatus by a first connector, and a pulse generator connected to the earpiece of the auricular component by a second connector according to an example.
Figure 2B:
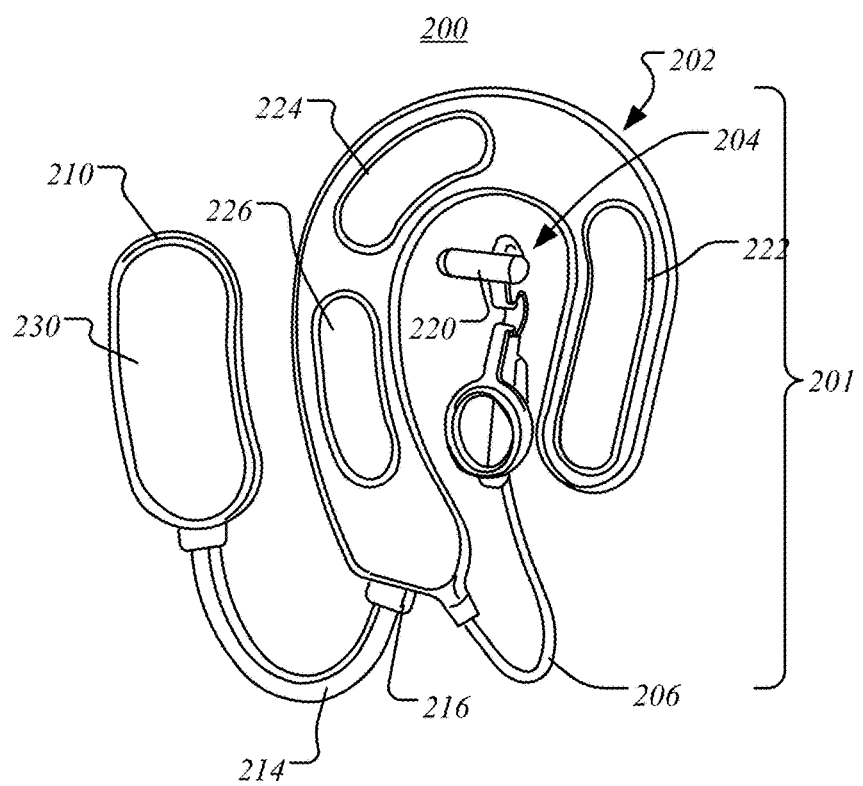
FIG. 2B is a drawing of an alternative view of the treatment device shown in FIG. 2A showing the concha apparatus including a first electrode or cymba electrode, and the earpiece including a second electrode and at least another electrode according to an example.

Turning to FIGS. 2A and 2B, a treatment device 200 is shown including an auricular component 201 having an earpiece 202 connected to a concha apparatus 204 by a first connector 206, and a pulse generator 210 connected to the earpiece 202 of the auricular component 201 by a second connector 214 according to an example. The first connector 206, in some embodiments, is releasably connected between the earpiece 202 and the concha apparatus 204. For example, at least one of a proximal (earpiece 202 side) end or at distal (concha apparatus 204 end) of the first connector 206 may be designed for releasable connection. In other embodiments, the first connector 206 is integrated with the earpiece 202 and concha apparatus 204, behaving as a conduit for bridging an electrical connection between the earpiece 202 and the concha apparatus 204. Similarly, in some embodiments, the second connector 214 is releasably connected between the earpiece 202 and the pulse generator 210. For example, at least one of a proximal (earpiece 202 side) end or at distal (pulse generator 210 end) of the second connector 214 may be designed for releasable connection. In other embodiments, the second connector 214 is integrated with the earpiece 202 and pulse generator 210, behaving as a conduit for bridging an electrical connection between the earpiece 202 and the pulse generator 210. Either of the first connector 206 or the second connector 214, in embodiments designed for releasable connection, may include at least one of its proximal or distal ends having a keyed connection with a corresponding port on the treatment device 200 for snug (e.g., non-spinning) connection or for assuring electrical alignment. In some embodiments designed for releasable connection, either of the first connector 206 or the second connector 214 is designed for locking connection. The locking connection, for example, may be a water-resistant locking connection to protect against shorting due to sweating, rain, etc.

In some embodiments, the earpiece 202 and/or the concha apparatus 204 are designed from inexpensive materials, allowing the apparatus to be disposable; lowering the cost per treatment and eliminating the need for maintenance. Disposable apparatus also provides for greater hygienics.

In some embodiments, the concha apparatus 204 includes a first electrode 220 configured to be in proximity to vagal related neural structures to enable electrical stimulation of the vagal related neural structures, and the earpiece 202 includes a second electrode 222 configured to be in proximity to a neural structure related to the auriculotemporal nerve to enable electrical stimulation of the auriculotemporal nerve. The earpiece 202 may further include at least another electrode 224, 226 configured to be in proximity to neural structures related to the great auricular nerve and/or its branches as well as the lesser occipital nerve and/or its branches to enable electrical stimulation of these structures. In an example, the pulse generator 210 can include a return electrode 230 configured to provide a return path or reference to electrodes 220-226. In another embodiment, electrodes 220-226 form pairs such that for example electrodes 220 and 226 form a pair are used to deliver bipolar stimulation; in this example a second pair could be formed by electrodes 222 and 224 such that bipolar stimulation is provided through them.

In yet another embodiment, electrodes 224 and 226 may be combined into a single electrode and be used as a share pair for electrodes 220 and 222 to produce biphasic pulses.

Figure 2C:
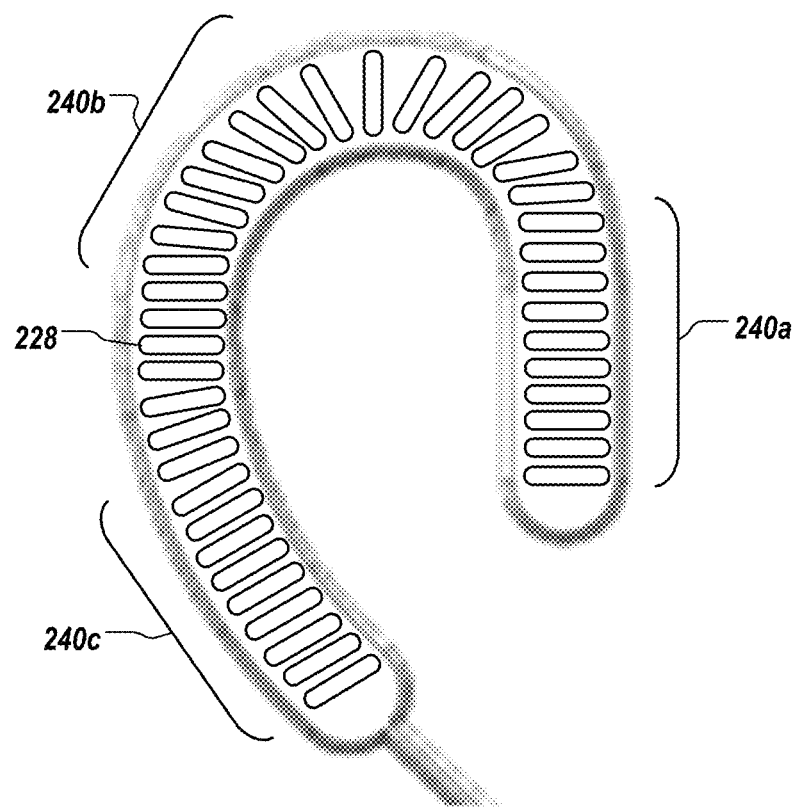
FIG. 2C is a drawing of a treatment device including a number of electrodes configured to be virtually grouped together to form one or more effective electrodes according to an example.
Figure 2D:
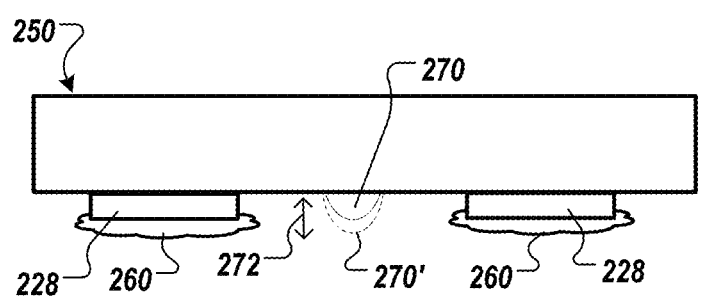
FIG. 2D is a drawing of a side view of a portion of a treatment device including haptic feedback actuators between a pair of electrodes according to an example.
Figure 2E:
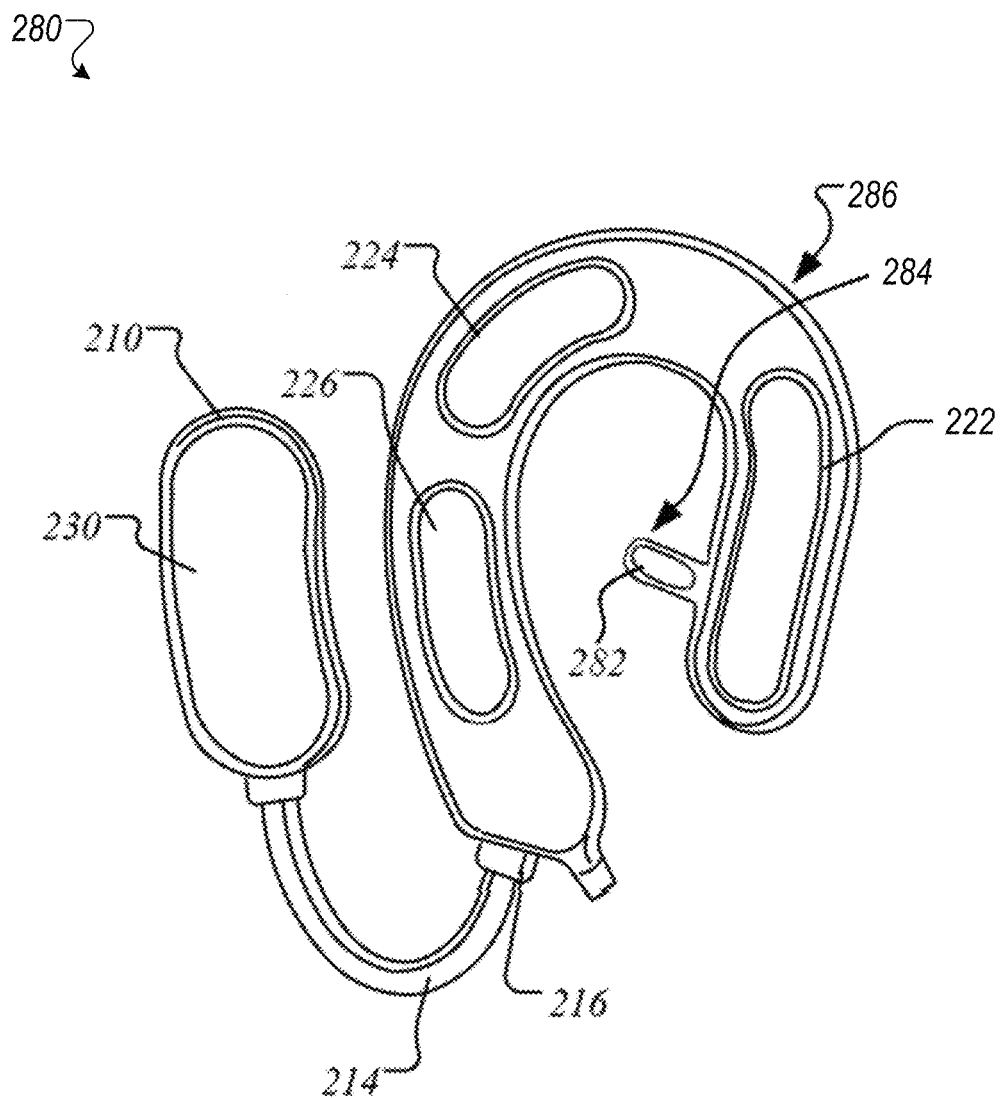
FIG. 2E is a drawing of an example treatment device having an earpiece with a tragus appendix.

Turning to FIG. 2E, some embodiments further include at least one tragus appendix for contacting and stimulating the tragus. As illustrated in FIG. 2E, for example, a tragus appendix 284 containing a tragus electrode 282 configured for stimulating the tissue of the tragus extends from an earpiece 286 of a treatment device 280. In some embodiments, the tragus appendix 284 can be folded such that it is in contact with the exterior-facing tissue of the tragus and/or with the interior-facing tissue of the tragus. For example, contacting the tragus can enable electrical stimulation of the auriculotemporal nerve and/or the vagus nerve branch. The tragus electrode 282, for example, may be provided instead of the first electrode 220 of the treatment device 200 of FIGS. 2A and 2B and can be configured with electrode 226 as a pair. In another embodiment (not illustrated), the tragus electrode 282 may be provided in addition to the first electrode 220, in which case both may share electrode 226 as their pair to produce biphasic pulses. In other embodiment, another electrode (not shown), used as the pair for electrode 282 to produce biphasic pulses, may placed, for example, below electrode 226.

In illustrative example, a treatment device such as the auricular component 201 of FIGS. 2A and 2B may be donned as follows. Apply the earpiece 202 around the auricle of the patient, press against the patient's skin such that exposed skin adhesives and adhesives/hydrogels adhere to the skin. Next, place the concha apparatus 204 in the ear such that a first portion of the concha apparatus 204 sits outside the external ear canal in the cavum. Finally, flex or compress a second or distal portion of the concha apparatus 204 supporting the cymba electrode until it goes into the cymba of the ear. In some implementations, the earpiece 202 includes one or more protective liners on one or more of the skin adhesive, the cymba electrode, and the non-cymba electrodes which are to be removed before use.

Turning to FIG. 2C, a treatment device can include a number of electrodes configured to be virtually grouped together to form one or more effective electrodes according to an example. In an exemplary embodiment, a treatment device can include a number of electrodes 228 that can be grouped together to form into one or more effective electrodes 240a-c. In an example, a grouping of electrodes 240a can be equivalent to electrode 222, a grouping of electrodes 240b can be equivalent to electrode 224, and a grouping of electrodes 240c can be equivalent to electrode 226.

Benefits of grouping smaller electrodes include having the ability to have multiple electrodes each one with its own independently controlled current source allows for the current to be steer providing better spatial resolution and targeting capabilities. Electrodes can also be made larger or combined such that for example in one embodiment electrodes 1206 and 1208 be combined into one large contact. In an example, the grouping of two or more electrodes (222, 224, 226) can be done using a processor such as a field-programmable gate array (FPGA) such as FPGA 1112.

In a preferred embodiment, a treatment device includes an auricular component 201 which has a number of electrodes that are configured to be in contact with the dermis in and around the outer ear. The auricular component 201 includes at least one of the following electrodes: an electrode configured to be in proximity to vagal related neural structures; for example at the cymba concha (also known as the concha of the cymba, concha cymba, and/or cymba) 204, an electrode 222 configured to be in proximity to a neural structure related to the auriculotemporal nerve, an electrode configured to be in proximity to neural structures related to the great auricular nerve and/or its branches, as well as the lesser occipital nerve and/or its branches, 224 and 226. Additionally, the treatment device includes a pulse generator 210 or controller having management software for providing the user with at least one of: customizing the therapeutic output, receiving confirmation of therapeutic delivery, and receiving and saving overall stimulation logs, diagnostics, and events.

In some implementations, a treatment device 250 can include one or more haptic feedback actuators 270 between a pair of electrodes 228 according to an example (FIG. 2D). In an aspect, the one or more haptic feedback actuators 270 can move 272 from a first position 270 to a second position 270' in repetitive patterns. In an example, the repetitive patterns can aid to mask sensations felt by stimulation of the electrodes. In an aspect, the one or more haptic feedback actuators 270 can be configured to isolate or electrically separate conductive shunting pathways between electrodes 228, including between portions of conductive gel 260.

Figure 3A:
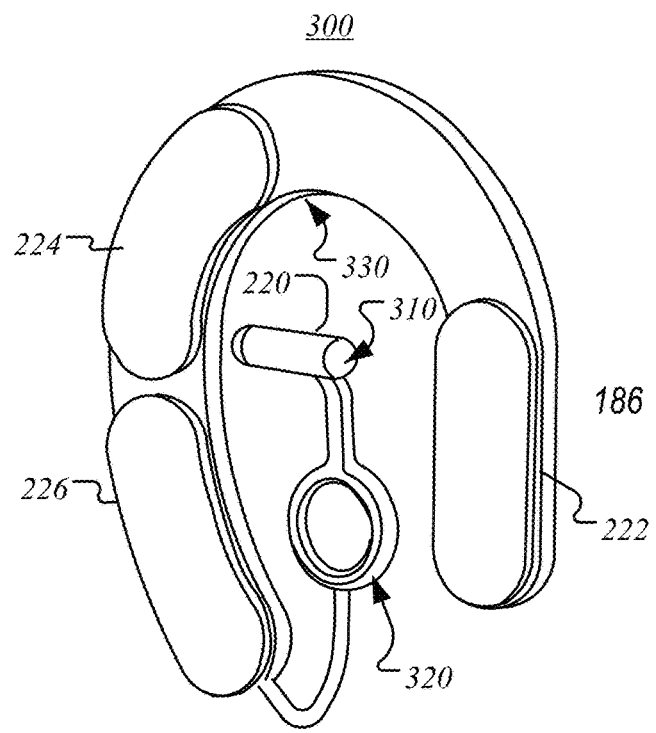
FIG. 3A is a drawing of an auricular component having an earpiece and concha apparatus with shapes configured to aid in securing the treatment device and respective electrodes to a respective ear structure according to an example.
Figure 3B:
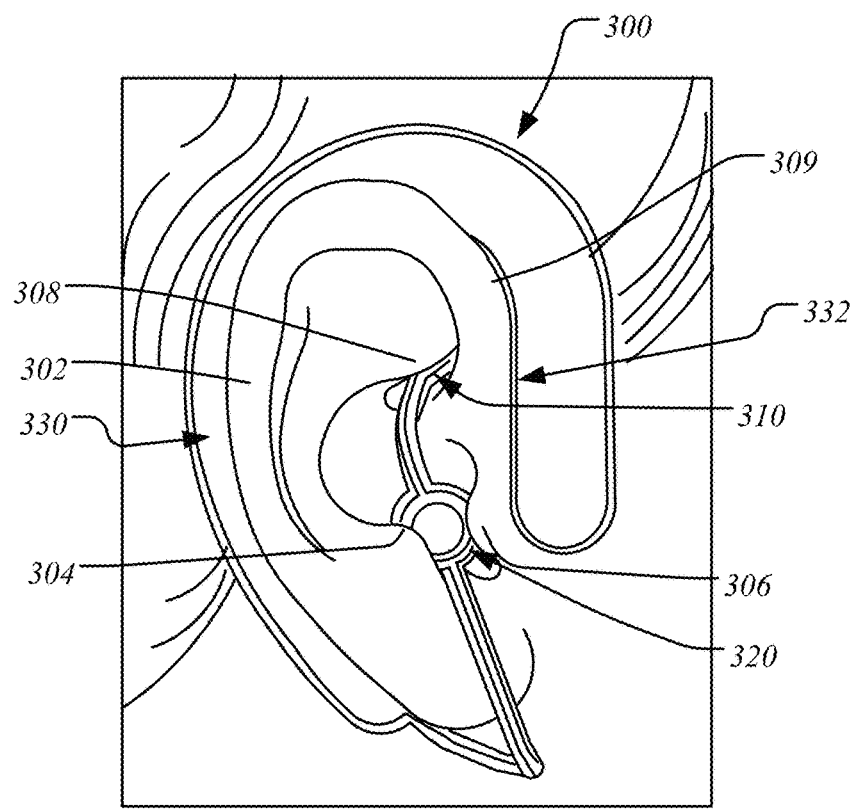
FIG. 3B is an illustration of the auricular component worn on the ear of a patient according to an example.
Figure 4A:
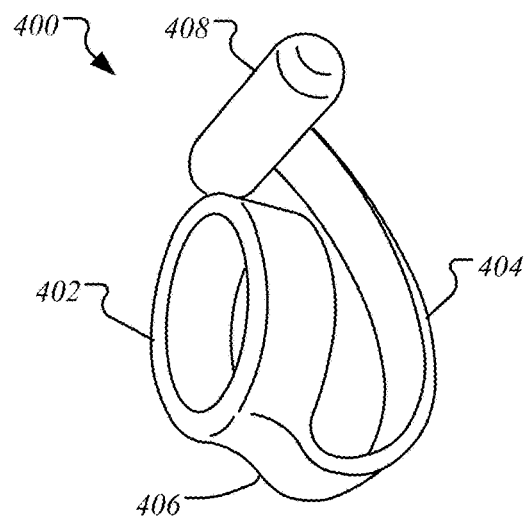
FIGS. 4A-4C are drawings of a concha apparatus having a shape configured to aid in securing the concha apparatus and respective supported electrodes to a respective ear structure according to another example.
Figures 4B, 4C:
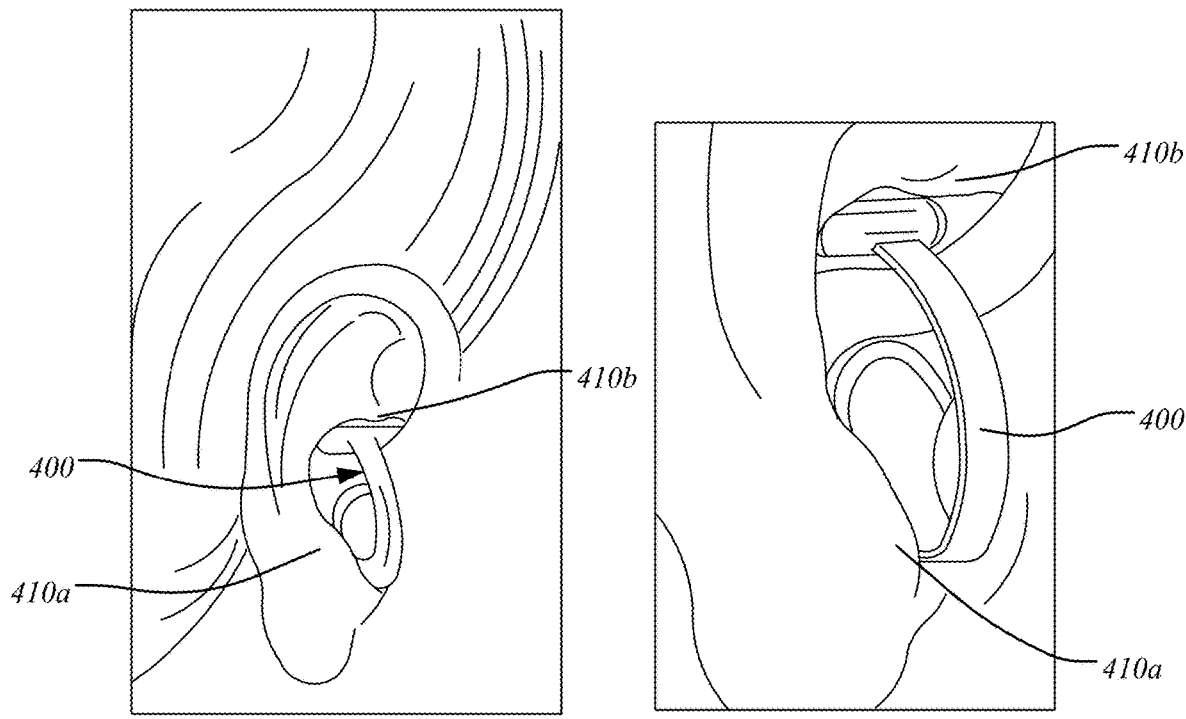

In an aspect, an auricular component can include an earpiece and concha apparatus having shapes configured to aid in securing the treatment device and the electrodes to a respective ear structure. In an exemplary embodiment, an auricular component 300 can include an earpiece and concha apparatus having shapes 310, 320, 330 configured to aid in securing the treatment device and the electrodes 220, 222, 224, 226 to a respective ear structure (See FIGS. 3A-3B). Shaped portions 310, 320, 330, 332 of the earpiece and the concha apparatus are configured to interface with structures of the ear (302, 304, 306, 308, 309) to facilitate secure placement of the electrodes for providing therapy. In another exemplary embodiment, a concha apparatus 400 can have a structural shape configured to aid in securing the concha apparatus 400 and allow for supported electrode(s) to maintain contact with a respective ear structure (See FIGS. 4A-4C). The concha apparatus 400 includes a first member 402 connected at a distal elbow 406 to an arm 404 having a second member 408 configured to fit within extrusions and notches 410a-b of the ear.

Figure 3C:
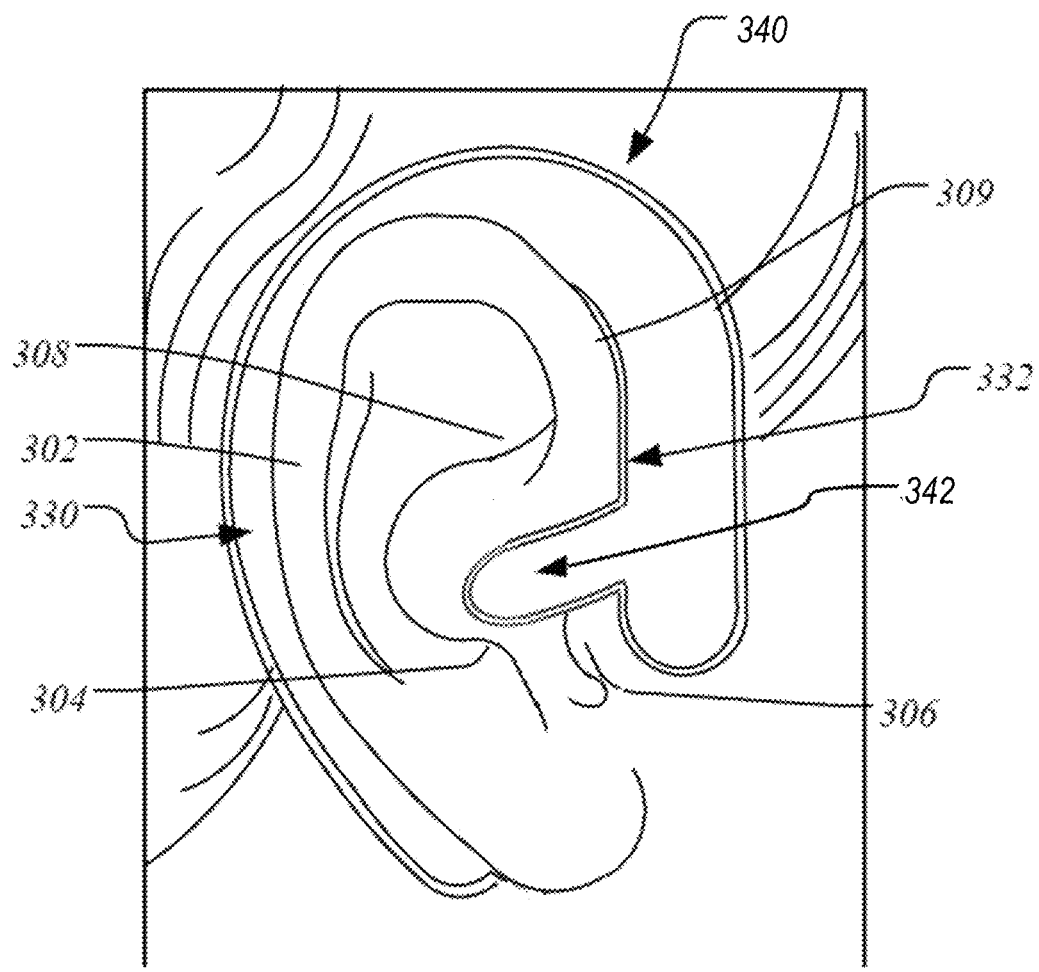
FIGS. 3C and 3D illustrate example auricular components including an electrode for contacting the tissue of the tragus.
Figure 3D:
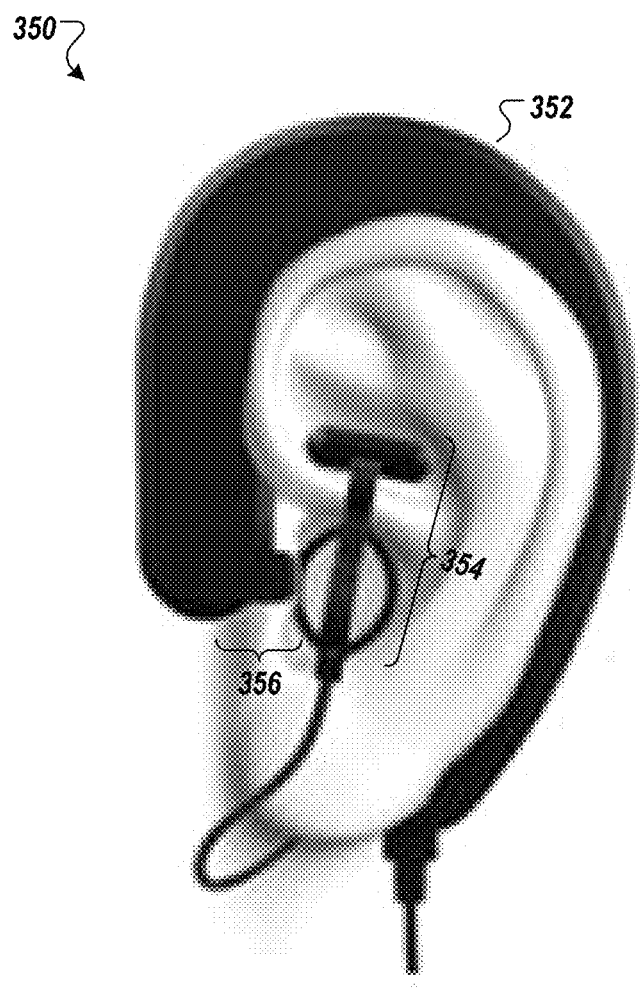

In some embodiments, an auricular component can include a tragus element configured to extend over or wrap around the tragus of the ear. In an illustrative example, FIG. 3C illustrates an earpiece 340 including a tragus extension 342. The tragus extension 342, for example, may be configured to contact an exterior-facing surface of the tragus. In another example, the tragus extension 342 may be foldable such that it curves around a surface of the tragus. In this configuration, the tragus extension may have one or both of an interior surface facing electrode and an exterior surface facing electrode. Turning to FIG. 3D, in another example, an auricular component 350 includes an earpiece 352 including a tragus bridging section 356 and a concha apparatus 354.

Figure 5A:
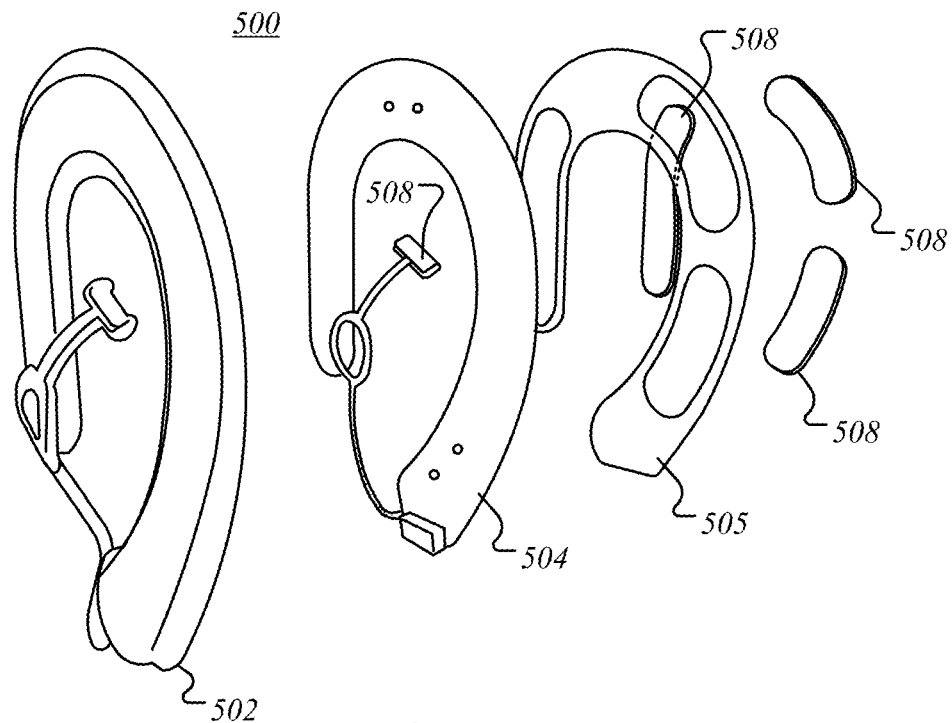
FIGS. 5A-5B are exploded views of components of the treatment device including a skin, a PCB layer, an adhesive layer composed of two elements, a skin adhesive and a number of conductive adhesive elements according to an example.
Figure 5B:
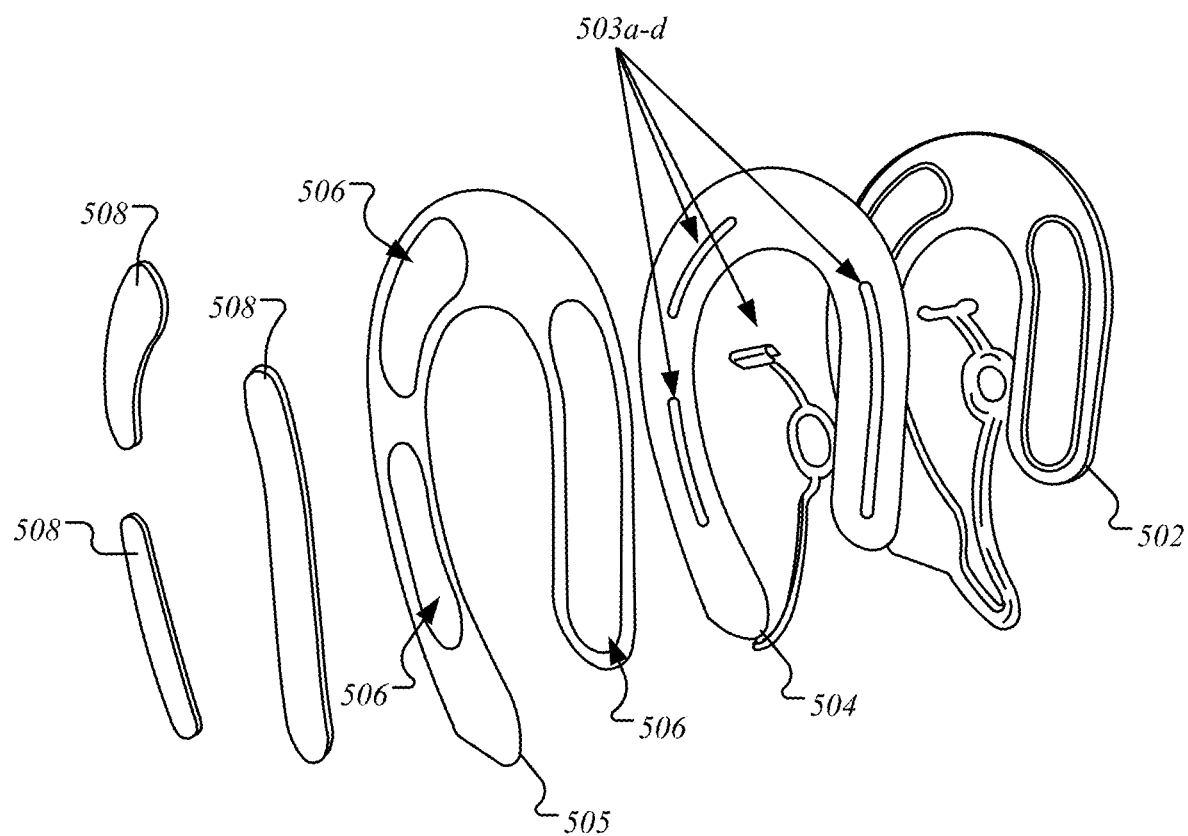

In some implementations, an earpiece assembly 500 includes a skin 502 for overlaying a PCB layer 504 having electrodes 503a-d (220, 222, 224, 226, 228), an adhesive layer composed of two elements, a skin adhesive 505 having corresponding apertures 506 to adhesive elements 508 configured for enhancing electrical interfacing of the electrodes 503a-d with the skin (See FIGS. 5A-5B). In some embodiments, the adhesive elements 508 can include a conductive hydrogel in another embodiment the hydrogel is infused with analgesic for a more comfortable stimulation. In an example, the hydrogel is on top of one or more contact surfaces on the flex PCB. In an example, the skin 502 can be made from a flexible piece or material such as silicone.

Figure 6:
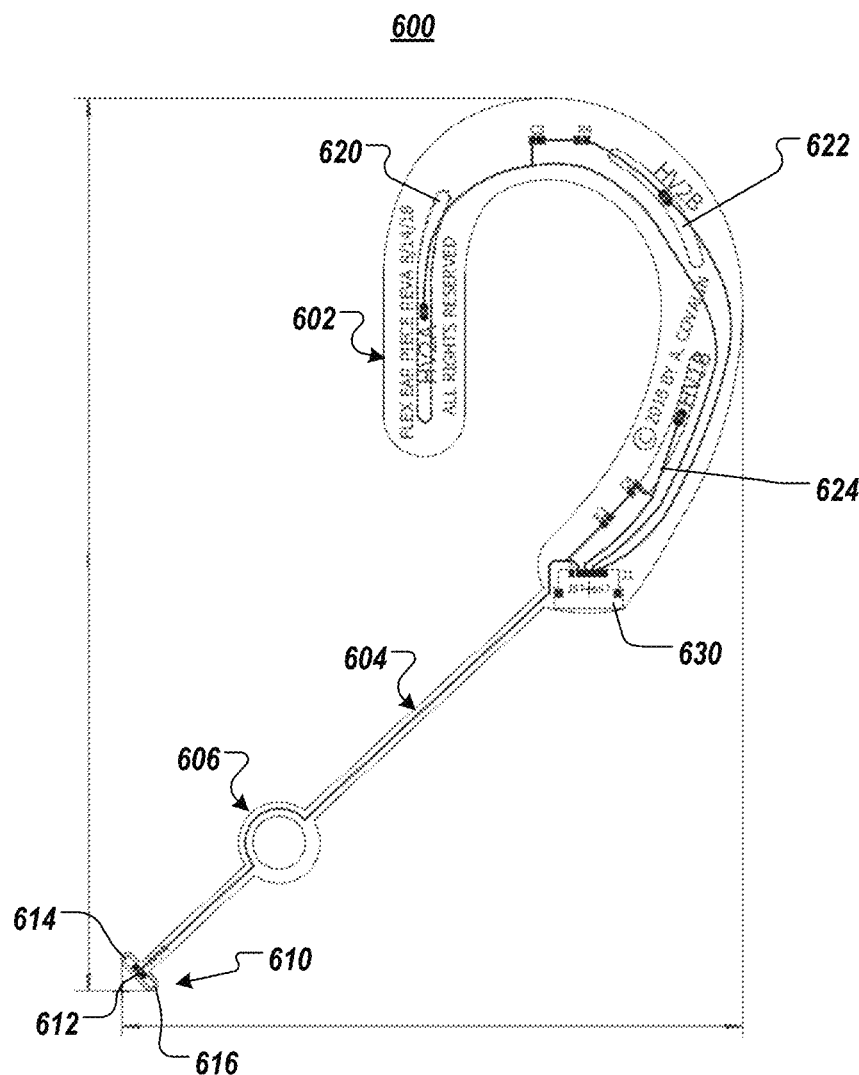
FIG. 6 is a drawing of a portion of an auricular component made from a flexible PCB according to an example.

In an example, a flexible PCB 602 can include electronic components to suppress electrical spikes as well as a component to identify and/or uniquely identify the PCB (See FIG. 6). Exposed conductive surfaces 612, 620, 622, 624 on the PCB 602 serve as contact points to connect the hydrogels 508 to the PCB 602. The PCB 602 extends forming a cable-like structure 604 to integrate the cymba component 610 of the electrode 220 in proximity to nerve branches related to vagal nerve structures 204 without the need for soldering and/or connecting the electrode 220 during assembly. In one embodiment, the cable-like structure forms an anchoring structure 606 which sits inside portions of the ear. In this example, PCB 602 connects to the pulse generator 210 via a slim keyed connector 630. In another embodiment, more than one electrode can be located on the cymba component 610. In this case, additional components can be added to the PCB 602 to accommodate additional electrodes including additional traces on the PCB 602. In an example, additional connections could extend along the cable-like structure 604 and connector 630 can have additional contact pins. In another embodiment, an analog multiplexor could be added to control and/or direct or re-direct the stimulation pulses towards a desired electrode and/or set of electrodes.

In some embodiments, the circuit 602 on the earpiece assembly 500 is formed with printed electronics.

Figure 7A:
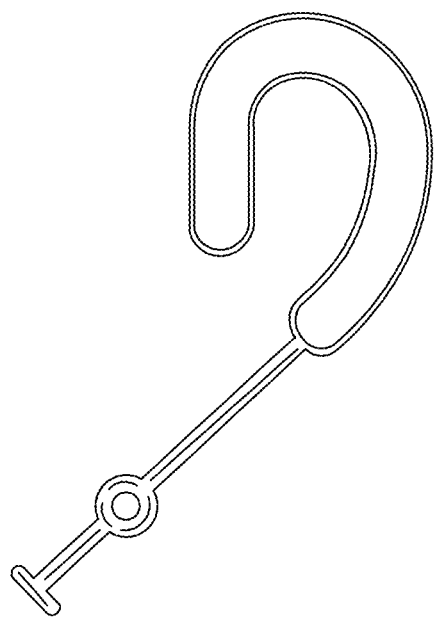
FIG. 7A-7C are drawings of the flexible PCB encapsulated in a protective covering according to an example.
Figure 7B:
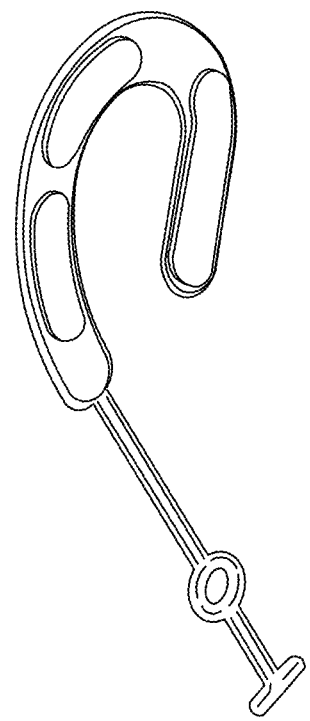
Figure 7C:
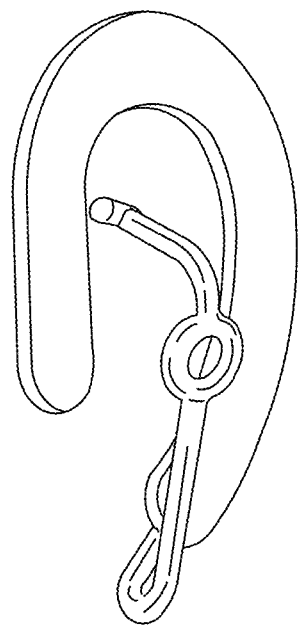

In an example, the flexible PCB can be encapsulated in a protective covering as shown in FIGS. 7A-7C. The protective covering can be made from a flexible material such as silicone. The protective covering can be an encapsulation that may have different thickness and densities in order to provide comfort to the touch and robustness and protection to the PCB. The encapsulation is done with at least one material. In some embodiments, the encapsulation is done at least in using one mold and at least one molding step.

Figure 8A:
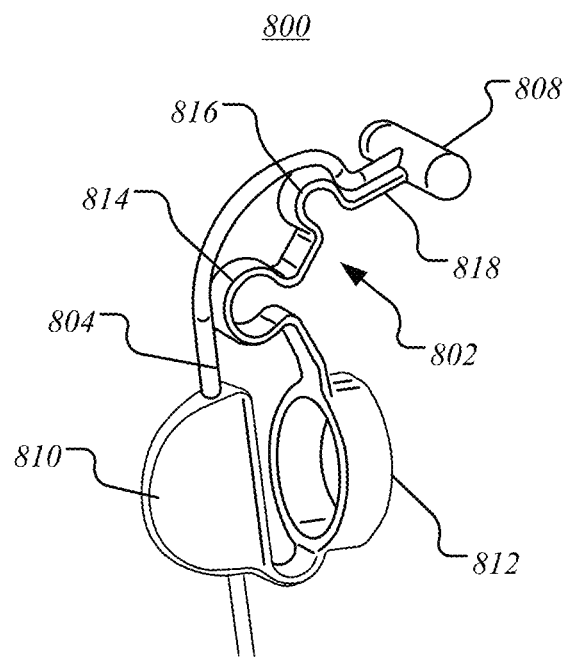
FIGS. 8A-8B are drawings of a structural-loaded component configured to facilitate placement of the cymba electrode according to an example.
Figure 8B:
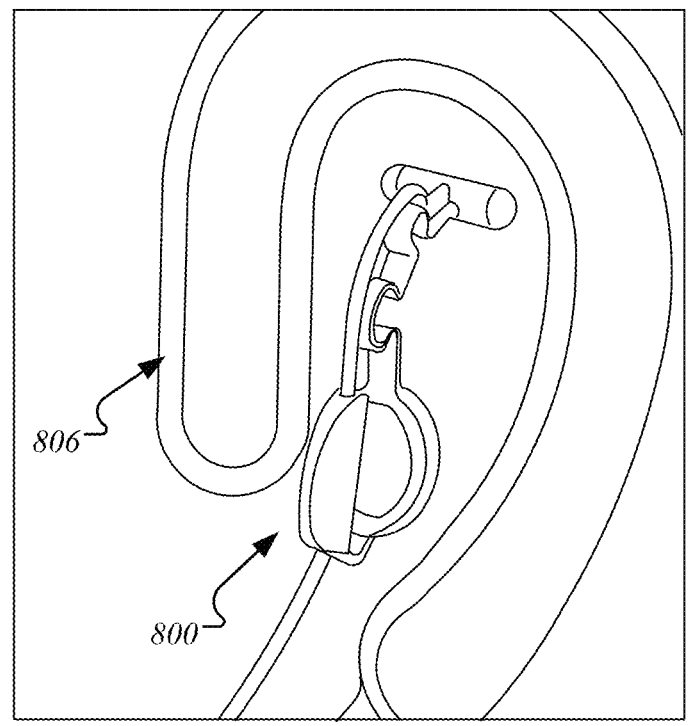

In an aspect, a concha apparatus can include a component for facilitating placement of the cymba electrode to portions of the ear. For example, the concha apparatus may be designed for frictional engagement with a concha of the ear, thus retaining a position of the concha apparatus external to the patient's ear canal in the concha. In an exemplary embodiment, a concha apparatus can include a structural-loaded component 800 which facilitates frictional retention of a cymba electrode 808 to portions of the ear (See FIG. 8A-8B). Compression loading, such as spring loading, has the added advantage that it is self-fitting allowing a secure and comfortable fit for different ear sizes. The presented shape (i.e., omega shape 814, 816) has the added advantage that it can be made with metal and non-metal materials. Other suitable shapes may be fabricated to allow a structural-loaded action using metal and/or non-metal materials or a combination of both metal and non-metal materials. The materials, for example, may include shape retaining materials or shape memory materials. In this example, the cable-like structure 604 after encapsulation with, for example, silicone 804 is routed such that the PCB 602 does not need to incorporate the anchoring structure 606. In this case, the cable-like structure 804 goes through a handle-like feature 810 that can be utilized by the user to handle and place the component 800 on the user's ear.

An anchoring structure 812 is placed in the ear and the electrode 808 in proximity to nerve branches related to vagal nerve structures 204 is placed in the cymba. The use of an anchoring structure outside the ear canal instead of a part going into the ear canal for the placement serves three purposes, comfort, functionally (it does not block sound), and safety (minimal risk of having a loose part going into the ear canal). Aside from the handle 810 and anchoring structure 812, component 800 has two omega-like structures 814, 816 having a structural-loaded effect, a flat structure 802 connecting structural-loaded components 814 and 816 and a flat structure 818 attaching electrode 204 to component 800. Structural-loaded structure 814 helps in directing the rest of component 800 (i.e., 802, 816, 818, 204) medially (i.e., towards the user's head) while the structural-loaded structure 816 helps in directing electrode 808 cranially inside the cymba crevice (i.e., towards the upper portion of the cymba crevice).

In an exemplary embodiment, a concha apparatus can include a compression-loaded component 900 which facilitates the placement of a cymba electrode 908 on the user's ear. (See FIG. 9A-9B). Compression loading, such as spring loading has the added advantage that it is self-fitting allowing a secure and comfortable fit for different ear sizes. The presented shape (i.e., classic spring) is usually fabricated with metallic materials. Other suitable shapes may be fabricated to allow a compression-loaded action using metallic materials, non-metal materials, or a combination of both metal and non-metal materials. The materials may include shape-retaining or shape-memory materials. In this example, the cable-like structure 604 after encapsulation with, for example, silicone 904 is routed such that the PCB 602 does not need to incorporate the anchoring structure 606. In this case, the cable-like structure 904 goes through holder 910 which can be utilized by the user to handle and placed the component 900 on the user's ear. An anchoring structure 912 is placed in the ear and the electrode 908 in proximity to nerve branches related to vagal nerve structures is placed in the cymba. The use of an anchoring structure outside the ear canal instead of a part going into the ear canal for the placement serves three purposes, comfort, functionally (it does not block sound), and safety (minimal risk of having a loose part going into the ear canal). Aside from the handle 910 and anchoring structure 912, component 900 has two springs 914, 916, a flat structure 902 connecting the two springs 914 and 916 and a flat structure 918 attaching electrode 908 to component 900. Spring 914 helps in directing the rest of component 900 (i.e., 902, 916, 918, 204) medially (i.e., towards the user's head) while spring 916 helps in directing electrode 908 cranially inside the cymba crevice (i.e. towards the upper portion of the cymba crevice). In some embodiments, a single wire 920 is shaped such that components 910, 912, 914, 916, and 918 are formed (See FIG. 9C). In some embodiments, the wire is encapsulated into a comfortable-to-the-touch and flexible material (e.g., silicone). In some embodiments, holder 910 is longer, for example it could bridge over the entire anchoring structure 912 for a more functional and comfortable handling.

In some implementations, the pulse generator 210 includes a battery, circuitry configured to produce therapy stimulation in communication with the electrodes of the auricular component 201. In some embodiments, the pulse generator includes at least one antenna configured to receive programming instructions encoding stimulation parameters. In an aspect, the system is rechargeable to allow for long-term use.

In an exemplary embodiment, the auricular component 201 is connected to an electrical pulse generator 210 which produces the therapy stimulation going to the electrodes on the auricular component 201. In some implementations, the pulse generator 210 is co-located in close proximity with the auricle of the patient. For example, the pulse generator 210 may be designed into or releasably connected to a head apparatus similar an over the head or back of the head headphones band or earmuffs band. In another example, the pulse generator 210 may be releasably retained in a pocket of a cap or head wrap donned by a patient. In other embodiments, the pulse generator 210 is placed on the body of the user, for example on the pectoral region just below the clavicle. In another embodiment, the pulse generator 210 can be clipped to the user's clothing or carried in the user's trousers pocket or in a specially designed pouch. In further embodiments, the pulse generator is built into the auricular component 201.

In some embodiments, the pulse generator 210 includes an input/output (I/O) interface for user control of the therapy. The I/O interface, for example, may include a number of controls, such as buttons, dials, or a touch pad, for adjusting therapy. In some examples, the I/O interface may include one or more of a mode selection, a length of time selection, or a stimulation strength control. Separate controls, in a further example, may be provided for the adjustment of the electrodes of the concha apparatus and for the electrodes of the earpiece.

In some embodiments, the pulse generator 210 is remotely configurable via wireless communication. In some embodiments, the wireless remote device may periodically request therapy status and in some embodiments the status, including any changes, may be communicated to a 3rd party such as a healthcare provider who is monitoring the therapy being applied to the user. For example, therapy provided via the pulse generator 210 may be controlled or adjusted at least in part using a peripheral device such as a mobile device, a tablet, or a personal computer. For example, a mode and/or stimulation strength may be adjusted by a clinical user (e.g., doctor, nurse, occupational therapist, etc.), while the timing (e.g., powering on and off and/or length of time setting) of the stimulation may be user-controlled via the I/O interface of the pulse generator 210. In another example, a software update to the pulse generator 210 may be delivered via wireless communication. The wireless communication, in some examples, can include radio frequency (RF) communication (e.g., Bluetooth) or near-field communication (NFC). The wireless communication may be enabled via an application installed on the peripheral device.

In some embodiments, other components of the treatment device are configurable by or capable of communication with a peripheral device. For example, data collected by the treatment device may be transferred to the peripheral device and thereby exchanged via a computing cloud with third parties such as healthcare professionals and/or healthcare providers Turning to FIGS. 10A-10C, in some implementations, a treatment system can include a treatment device 1000 in communication with a network 1020 and/or one or more peripheral devices 1010. Certain peripheral devices 1010, further, may enable communication between the treatment device 1000 and one or more third parties. Examples of peripheral devices 1010 include a personal computer, a tablet, or phone. In some embodiments, the peripheral device(s) 1010 include a fitness-monitoring device, such as a Fitbit, Apple Watch, or Garmin Smartwatch. In some embodiments, the peripheral device(s) 1010 include a health-monitoring device, such as a glucose meter, a holter monitor, an electrocardiogram (EKG) monitor, or an electroencephalogram (EEG) monitor. Further, the peripheral devices 1010, in some embodiments, include a remote server, server farm, or cloud service accessible via the network 1020. Certain peripheral device(s) 1010 may communicate directly with the treatment device 1000 using short-range wireless communications, such as a radio frequency (RF) (e.g., Bluetooth, Wi-Fi, Zigbee, etc.) or near-field communication (NFC). Certain peripheral device(s) 1010 may communicate with the treatment device 1000 through another peripheral device 1010. For example, using Bluetooth communications, information from the treatment device 1000 may be forwarded to a cloud service via the network 1020 (e.g., using a Wi-Fi, Ethernet, or cellular connection). The network 1020, in some examples, can include a local area network (LAN), wide area network (WAN), metro area network (MAN) or the Internet. In some embodiments, the network is a clinical LAN used for communicating information in a medical environment, such as a hospital, in a secure (e.g., HIPAA-compliant) manner.

Figure 10A:
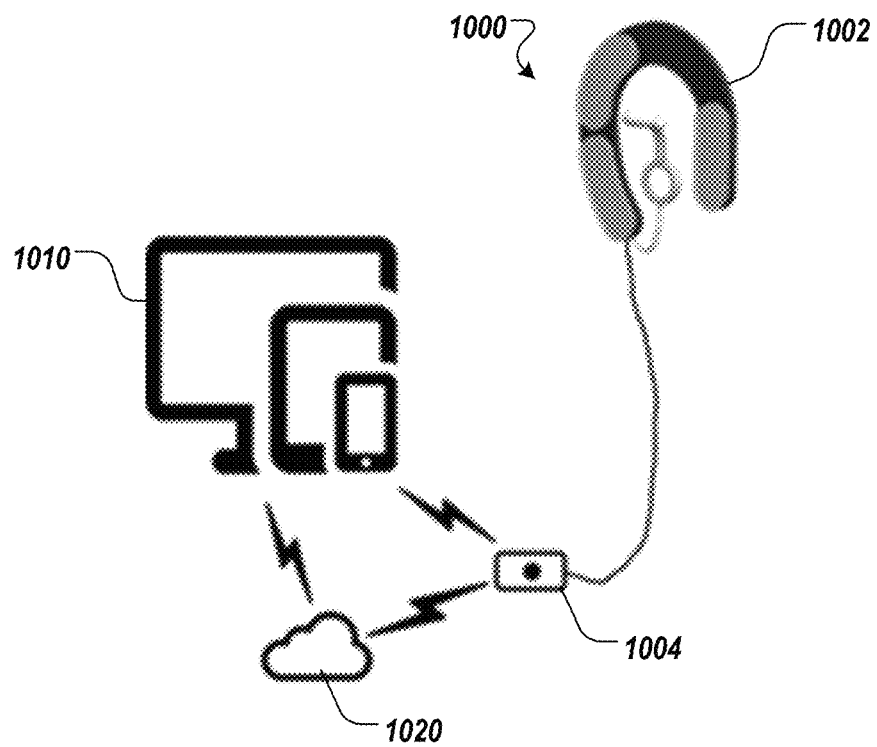
FIGS. 10A-10C are drawings of a system including the treatment device in communication with third parties through a computing cloud and/or a peripheral device according to an example.

In an example illustrated in FIG. 10A, the treatment device 1000 is shown including an auricular component 1002 connected via a connector to a pulse generator 1004, and the pulse generator 1004 is wirelessly connected to the peripheral device(s) 1010 and/or the network 1020. This configuration, for example, may enable a patient, caregiver, or clinical user to adjust settings and/or monitor treatment controlled by the pulse generator 1004. For example, an application running on a peripheral device 1010 may provide one or more adjustable controls to the user for adjusting the delivery of therapy by the pulse generator 1004 to the patient via the auricular component 1002. Further, feedback data gathered by the auricular component 1002 and/or the pulse generator 1004, such as sensor feedback, may be supplied by the pulse generator 1004 to one or more of the peripheral devices 1010. The feedback, for example, may include sensor signals related to symptoms of the patient being treated by the treatment device 1000. A clinical user monitoring sensor metrics related to these signals may manually adjust the delivery of therapy accordingly using the one or more adjustable controls provided by the application. Further, in some implementations, the feedback may be used by one of the peripheral devices 1010 to generate a notification for review by the patient, a caregiver, or a clinician. The notification, for example, may include a low power notification, a device removed notification, or a malfunction notification. In an illustrative example, the treatment device 1000 may monitor impedance measurements allowing closed-loop neurostimulation. The notifications regarding removal or malfunction, for example, may be issued upon determining that the impedance measurements are indicative of lack of a proper contact between one or more electrodes of the treatment device 1000 and tissue on or surrounding the patient's ear. The notifications, for example, may be delivered to the patient and/or one or more third parties via an application executing on one of the peripheral devices 1010. For example, the application may issue an audible alarm, present a visual notification, or generate a haptic output on the peripheral device 1010. Further, in some embodiments, the application may issue a notification via a communication means, such as sending an email, text message, or other electronic message to one or more authorized users, such as a patient, caregiver, and/or clinician.

Conversely, in some implementations, the configuration illustrated in FIG. 10A enables automatic adjustment of therapy delivery by reviewing feedback provided by the treatment device and/or one or more peripheral devices 1010 (e.g., fitness monitors and/or health monitors used by the patient). In one example, a cloud platform accessible via the network 1020 may receive the feedback, review present metrics, and relay instructions to the pulse generator 1004 (e.g., via a Wi-Fi network or indirectly via a local portable device belonging to the patient such as a smart phone app in communication with the treatment device 1000). The pulse generator, in a further example, may gather feedback from the one or more fitness monitor and/or health monitor devices 1010, analyze the feedback, and determine whether to adjust treatment accordingly.

Figure 10B:
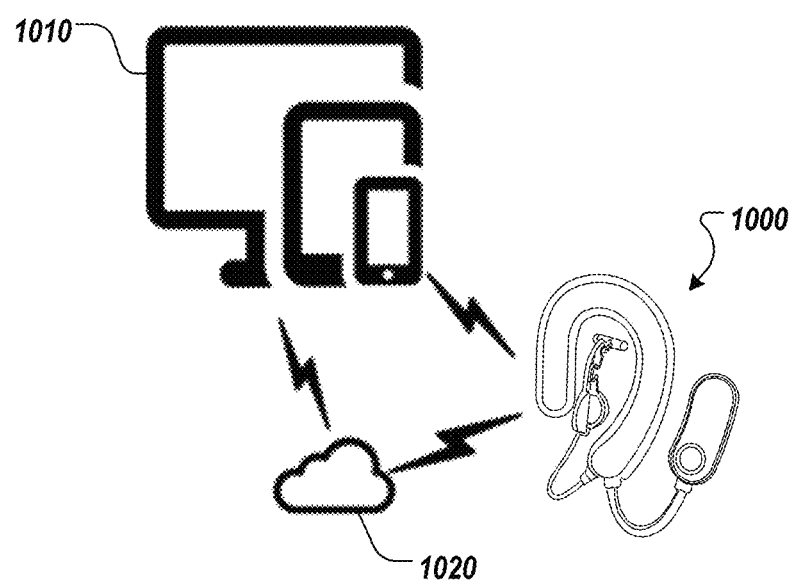

Turning to FIG. 10B, in some implementations, the auricular component 1002 of the treatment device 1000 may further be enabled for wireless transmission of information with one or more peripheral devices 1010. For example, the auricular component 1002 may include a short-range radio frequency transmitter for sharing sensor data, alerts, error conditions, or other information with one or more peripheral devices 1010. The data, for example, may be collected in a small non-transitory (e.g., non-volatile) memory region built into the auricular component 1002.

In other implementations, the pulse generator 210 is included in the auricular component 1002 that is, they are co-located thus the need for an extension cable to connect them is not necessary. The auricular component 1002 and pulse generator 210 may be wirelessly connected to an electronic device (for example a personal computer, a tablet or a phone) 1010 and/or to a remote server 1010 via the network 1020. In turn, in some embodiments, the electronic device 1010 is also wirelessly connected to a remote server via the network 1020.

Figure 10C:
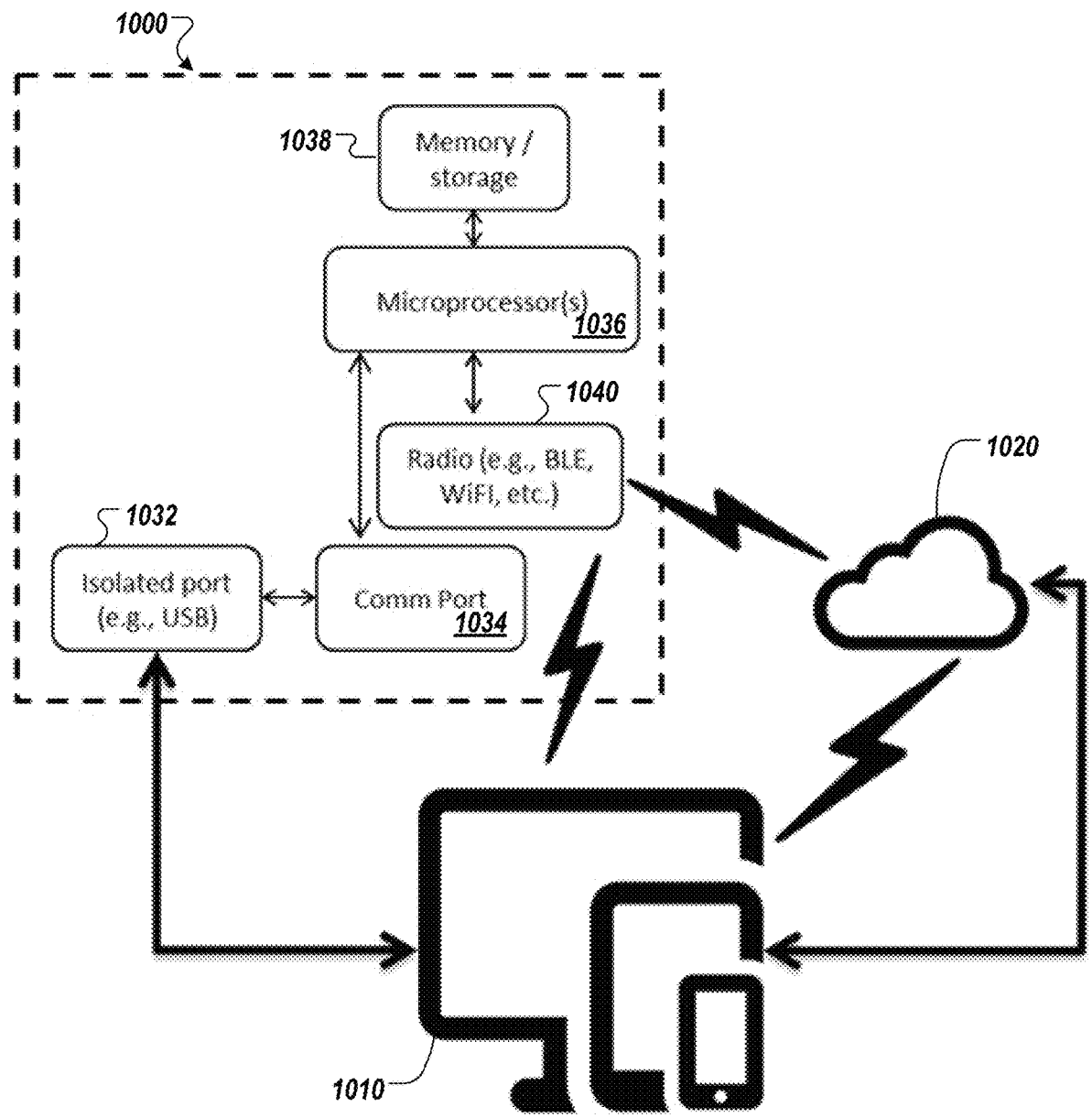

As shown in FIG. 10C, different communication components of the treatment device 1000 can be in communication with the peripheral device(s) 1010 or network 1020. In some implementations, the treatment device 1000 includes at least one isolated port 1032 for wired communication with the peripheral device 1010. The isolated port 1032, in some examples, may be a universal serial bus (USB) connection (e.g., a mini-USB connection, a micro-USB connection, a USB-C port, etc.), an Ethernet port, or a Serial ATA (SATA) connector. The isolated port 1032, for example, may be included in the pulse generator 1004 for updating a software version running on the pulse generator 1004 or for reprogramming treatment settings of the pulse generator 1004. The isolated port(s) 1032 may be connected to a communications port engine 1034 for enabling communications between a peripheral device 1010 and the treatment device 1000 via the isolated port 1032. The communications port engine 1034 may couple the isolated port 1032 to one or more microprocessors 1036. For example, the communications port engine 1034 may establish a direct (e.g., wired) communication link with one of the peripheral device(s) 1010 to transfer data from a memory 1038 to the peripheral device 1010.

Further, a wireless radio frequency (RF) antenna (e.g., transmitter or transmitter/receiver) 1040, in some implementations, is included in the treatment device 1000. The RF antenna 1040 can be in wireless communication with the peripheral device(s) 1010 directly or via the network 1020. The RF antenna 1040, in combination with processing circuitry for generating wireless communications (e.g., another communication port engine 1034 or a portion of the microprocessor(s) 1036) may function as a broadcast antenna, providing information to any RF receiver in a receiving region of the treatment device 1000. For example, the RF antenna 1040 may broadcast sensor data, sensor metrics, alerts, alarms, or other operating information for receipt by one or more peripheral devices 1010. In other implementations, the RF antenna 1040, in combination with additional processing circuitry, may establish a wireless communication link with a particular peripheral device 1010. The wireless communication link, in some embodiments, is a secure wireless communication link (e.g., HIPAA-compliant) for sharing patient data with the peripheral device(s) 1010. The wireless communication link may be used to receive control settings from a peripheral device 1010 for controlling the functionality of the pulse generator, for example.

Figure 11:
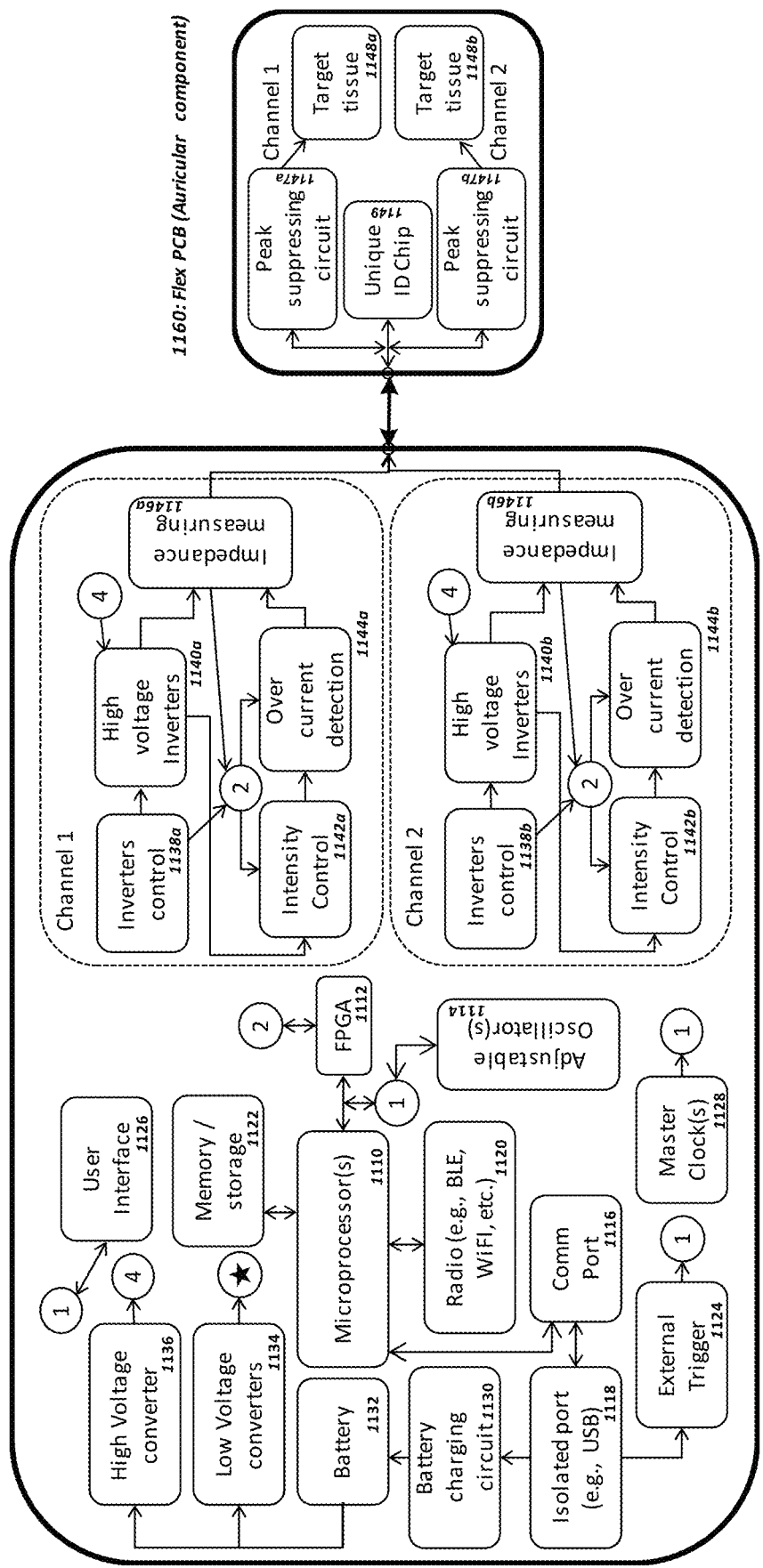
FIG. 11 is a drawing of a schematic of components of a pulse generator in communication with components of the flexible PCB of the auricular component according to an example.

Turning to FIG. 11, a schematic 1100 of components of a pulse generator 1150 in communication with components of the flexible PCB 1160 of the auricular component is shown according to an example. The multichannel pulse generator circuit 1150 has at least one microcontroller or a microprocessor 1110 with at least one core. When multiple microcontrollers or multiple cores are present, for example one controls the radio 1120 and other core(s) are dedicated to control the therapy. In one embodiment, a low power programmable logic circuitry (e.g., FPGA or PLD) 1112 is also available such that the microcontroller 1110 goes into a low power mode as much as possible while the programmable logic circuitry 1112 controls therapy delivery.

In some embodiments, an inverter circuit 1140 is used to generate biphasic/bipolar pulses. In some embodiments, one inverter circuit is used per channel, while in other embodiment, a single inverter is used for multiple channels. In one embodiment, each channel targets a different anatomical area 1148. A high voltage compliance (e.g., >50V, in other embodiments >70V, and yet in others >90V) may be used to ensure there is enough margin on the electrical potential to generate current demanded by the intensity control 1142. In order to enhance safety, in some embodiments an over current detection circuit 1144 is present. In one embodiment an impedance measuring circuit is present 1146, such that impedance can be tracked over time and to identify when the electrodes are not in contact or in good contact with the skin or if the cable is disconnected, or if the electrodes have deteriorated or are defective. Monitoring impedance over time provides the added advantage that the condition of the contact electrode can be followed; thus allowing the circuit to alert the user when the contact electrodes are close to their end of life or no longer viable.

In some embodiments, an isolated port 1118, such as a USB is used to charge the battery, and to communicate with the microcontroller(s) 1110. The communication can be both ways, such that instructions or entire new code can be uploaded to the microcontroller(s) 1110 and to download information stored in the memory 1122. In some embodiments, memory 1122 can be added to the circuit as an external CHIP, while in other embodiments, the memory 1122 can be internal to the microcontroller(s) 1110. In some embodiments, the FPGA 1112 may also have internal memory. In some embodiments, an external trigger circuit 1124 is included, such that the stimulation can be started and/or stopped via an external signal. In some embodiments, the external trigger signal can be passed through the isolated port 1118; in yet other embodiments a modify USB configuration (i.e., not using the standard USB pin configuration) can be used to pass the trigger signal. Using a modify USB configuration will force a custom USB cable to be used thus ensuring that an external trigger cannot be done by mistake using an off-the-shelf USB cable.

In some embodiments, a hardware user interface 1126 is used to interact with the circuit. In an example, the user interface 1126 can include buttons, LEDs, haptic (e.g., piezoelectric) devices such as buzzers, and/or a display, or a combination of any of them.

In some embodiments, an external master clock 1128 is used to drive the microcontroller(s) 1110 and/or the FPGA 1112, in other embodiments the clock(s) can be internal or integrated or co-packaged with the microcontroller(s) 1110 and/or the FPGA 1112. In some embodiments, one or more oscillators, including in some cases adjustable oscillators 1114 are used to set pulse parameters such as for example, frequency and/or pulse width.

In some embodiments, the auricular component 1160 is made from a thin flex PCB or printed electronics, such that it is light weight and can be easily bent to accommodate different anatomies. In some embodiments, the auricular circuit 1160 has more than one channel. In one embodiment, each channel includes a peak suppressing circuit 1147 and electrodes 1148 to contact the skin at the location of the target tissue. In some embodiments, the auricular circuit 1160 includes a unique chip identifier or unique ID chip 1149. The unique ID chip can be used to track usage as well as to prevent other no authorized circuits to be connected to the multichannel pulse generator 1150. At least one auricular circuit 1160 is connected to the multichannel pulse generator 1150.

Turning to FIGS. 14A-14C, a method 1400 is disclosed for providing therapy to a patient. The therapy, in some examples, may include the treatment of acute or chronic pain, inflammatory conditions, and/or cognitive difficulties. In a particular example, the therapy may include the treatment to abate withdrawal symptoms.

In some implementations, the method 1400 includes providing a first stimulation 1410 at a first tissue location configured to stimulate a first pathway 1420 for modulating a first release 1430 of at least one first endogenous peptide. The first endogenous peptide release, for example, may be an endorphin and/or enkephalins release Examples of target pathways and structures (1420) for stimulation of the first tissue location include those modulating activity at/on the auricular branch of the vagus nerve, the lesser occipital nerve, the great auricular nerve, and the arcuate nucleus, for example as shown in FIG. 14B. The first tissue location, for example, may be a tissue location contacted by one or more electrodes of the concha apparatus 204 of FIGS. 2A-2C.

In some implementations, the method 1400 includes providing a second stimulation 1440 at a second tissue location configured to stimulate a second pathway 1450 for modulating a second release 1460 of a second endogenous peptide. The second endogenous peptide release, for example, may be a dynorphin release. Examples of target pathways and structures (1450) for stimulation of the second tissue location include those modulating activity at/on the auriculotemporal nerve, the lesser occipital nerve, the great auricular nerve, and the parabrachial nucleus, for example as shown in FIG. 14C. In some examples, the first electrode 220 of FIG. 2B, an electrode in the second member 408 of FIG. 4A, the electrode 503c of FIG. 5B, an electrode disposed on the anchoring structure 606 of FIG. 6, or the electrode 1202 of FIG. 12 may be used to provide the first stimulation.

In some embodiments, providing the first stimulation (1410) and providing the second stimulation (1440) involves providing a series of simultaneous and/or synchronized stimulation pulses to both the first tissue location and the second tissue location. Each of the first stimulation (1410) and the second stimulation (1440) may be applied using the same or different parameters. The parameters, in some examples, may include pulse frequency (e.g., low, mid-range, or high) and/or pulse width. Further, the parameters may indicate electrode pairs for producing biphasic pulses. In a first illustrative example, the first stimulation may be applied using a low frequency, while the second stimulation is applied using a mid-range frequency. Conversely, in a second illustrative example, the first stimulation may be applied using a mid-range frequency, while the second stimulation is applied using a low frequency. Other combinations of low, mid-range, and high frequency stimulations are possible depending upon the patient and the disorder being treated.

In other embodiments, the method 1400 includes automatically adjusting delivery of the therapy (e.g., adjusting one or more parameters) based on feedback received from the pulse generator or another computing device in communication with the pulse generator. The feedback, in some examples, may include sensor feedback provided by the treatment device and/or one or more peripheral devices (e.g., fitness monitors and/or health monitors used by the patient, medical apparatus in a clinical environment, etc.).

Figure 14D:
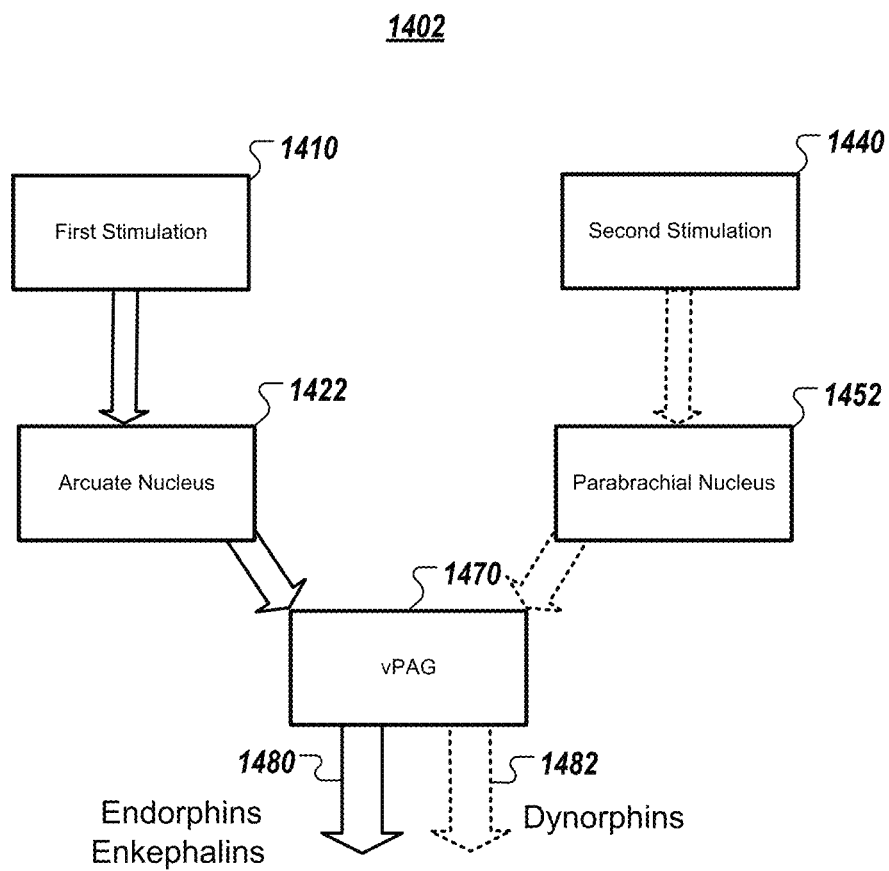
FIG. 14D is a flow chart of a method for providing therapy including providing a first stimulation at a first tissue location such that neural activity at the arcuate nucleus of the hypothalamus (ARC) is modulated such that it stimulates the Periaqueductal Gray Area (PAG) for modulating a first release of enkephalins and/or endorphins, and a second stimulation at a second tissue location such that neural activity at the Parabrachial Nucleus (PbN) is modulated such that it also stimulates the Periaqueductal Grey Area (PAG) for modulating a second release of a dynorphins, according to an example.

FIG. 14D shows a flow chart of an example method 1402 for providing a therapy as described in relation to FIG. 14A. In some implementations, the method 1402 includes providing the first stimulation 1410 such that neural activity at the arcuate nucleus of the hypothalamus (ARC) is modulated (1422) such that it stimulates the Periaqueductal Gray Area (PAG) (1470) for modulating a first release of enkephalins and/or endorphins (1480). In some implementations, the method 1402 includes providing the second stimulation 1440 such that neural activity at the Parabrachial Nucleus (PbN) (1452) is modulated such that it also stimulates the Periaqueductal Grey Area (PAG) (1470) for modulating a second release of a dynorphins (1482). Additionally, the second stimulation 1440 may contribute to releasing enkephalins and/or endorphins (1480).

Figures 14E, 14F:
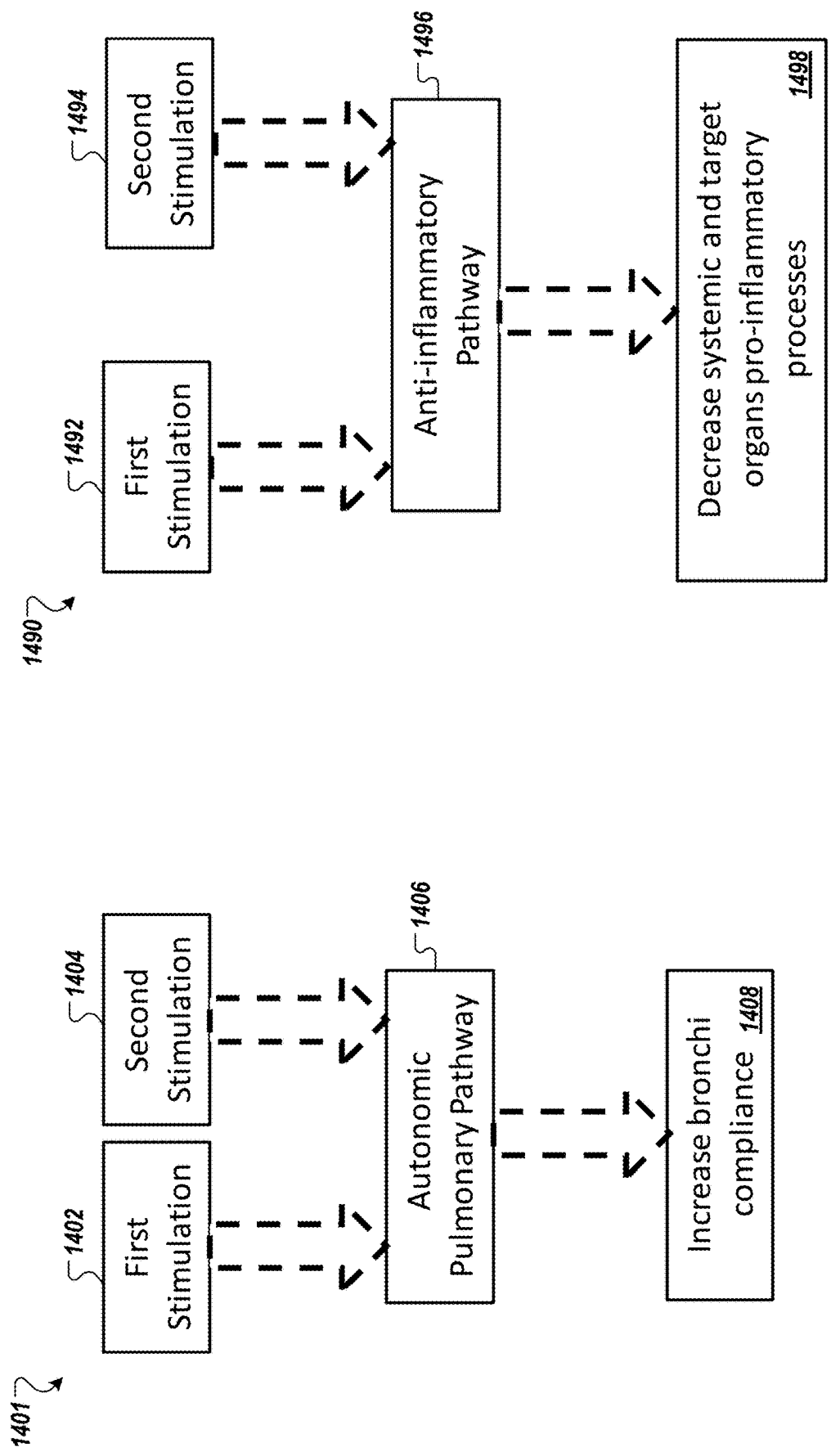
FIG. 14E is a flow chart of an example method for providing therapy for increasing bronchi compliance.
FIG. 14F is a flow chart of an example method for providing therapy for decreasing pro-inflammatory processes.

Turning to FIG. 14E, a flow chart of an example method 1401 is illustrated for providing therapy to increase bronchi compliance. The therapy of method 1401, for example, may encourage bronchodilation, thereby reducing airway resistance. Further, the therapy of method 1401 may increase the oxygen transport availability of the lungs, increasing the potential for more oxygen to be absorbed into the blood. The method 1401, in some examples, may be applied in combatting COPD symptoms and/or symptoms produced by a viral or bacterial infection. The viral infection, in some examples, can include SARS, MERS, or COVID-19. The method 1401, for example, may be performed at least in part by a pulse generator, such as the pulse generator 210 of FIGS. 2A and 2B, the pulse generator 1004 of FIG. 10A, or the pulse generator 1150 of FIG. 11.

In some implementations, the method 1401 begins with providing a first stimulation 1402 at a first tissue location configured to stimulate an autonomic pulmonary pathway 1406 for modulating bronchi compliance 1408. Examples of target pathways and structures for stimulation of the first tissue location include those modulating activity at/on the auricular branch of the vagus nerve, the lesser occipital nerve, the great auricular nerve, and/or the nucleus ambiguous. The pathways, for example, may include a portion of the pathways illustrated in FIG. 1F. The first tissue location, for example, may include a surface of an ear structure contacted by an in-ear component of an auricular stimulation device. In some examples, the first electrode 220 of FIG. 2B, an electrode in the second member 408 of FIG. 4A, the electrode 503c of FIG. 5B, an electrode disposed on the anchoring structure 606 of FIG. 6, or the electrode 1202 of FIG. 12 may be used to provide the first stimulation. The first tissue location, in another example, may be a tissue location contacted by the tragus appendix 282 of FIG. 2E. In some embodiments, the first stimulation 1402 is supplied to multiple tissue locations. For example, the first stimulation 1402 may be applied to a first tissue location including a surface of an ear structure contacted by an in-ear component of an auricular stimulation device as well as to a second tissue location on a tragus of the ear (e.g., contacted by the tragus appendix 282).

Modulating bronchi compliance 1408, in some implementations, includes modulating activity at the NTS, thereby affecting activity at the LC, PAG, and/or RN (e.g., NRM) which in turn modulates activity in the NA such that the smooth muscle tone in the airways is modified according to an example.

In some implementations, the method 1401 includes providing a second stimulation 1404 at a second tissue location configured to stimulate the autonomic pulmonary pathway 1406 for modulating bronchi compliance 1408. Examples of target pathways and structures for stimulation of the second tissue location include those modulating activity at and/or on the auriculotemporal nerve, the lesser occipital nerve, and/or the great auricular nerve. The pathways, for example, may include a portion of the pathways illustrated in FIG. 1F. The second tissue location, for example, may be a tissue location contacted by one or more of the electrodes 222, 224, and/or 226 of the earpiece 202 of FIGS. 2A-2C.

In some embodiments, providing the first stimulation (1402) and providing the second stimulation (1404) involves providing a series of simultaneous and/or synchronized stimulation pulses to both the first tissue location and the second tissue location. Each of the first stimulation (1402) and the second stimulation (1404) may be applied using the same or different parameters. The parameters, in some examples, may include pulse frequency (e.g., low, mid-range, or high) and/or pulse width. Further, the parameters may indicate electrode pairs for producing biphasic pulses. In a first illustrative example, the first stimulation may be applied using a low frequency, while the second stimulation is applied using a mid-range frequency. Conversely, in a second illustrative example, the first stimulation may be applied using a mid-range frequency, while the second stimulation is applied using a low frequency. Other combinations of low, mid-range, and high frequency stimulations are possible depending upon the patient and the disorder being treated.

In other embodiments, the method 1401 includes automatically adjusting delivery of the therapy (e.g., adjusting one or more parameters) based on feedback received from the pulse generator or another computing device in communication with the pulse generator. The feedback, in some examples, may include a blood oxygen concentration, a breathing rate, a breathing variation, and/or tidal volume.

Turning to FIG. 14F, a flow chart of an example method 1490 is illustrated for providing therapy to decrease systemic pro-inflammatory processes and/or pro-inflammatory processes in one or more target organs. The target organs, for example, may include the spleen, lungs, gut, and heart. The method 1490, in some examples, may be applied in combatting symptoms produced by COPD and/or produced by a viral or bacterial infection. The viral infection, in some examples, can include SARS, MERS, or COVID-19. The method 1490, for example, may be performed at least in part by a pulse generator, such as the pulse generator 210 of FIGS. 2A and 2B, the pulse generator 1004 of FIG. 10A, or the pulse generator 1150 of FIG. 11.

In some implementations, the method 1490 begins with providing a first stimulation 1492 at a first tissue location configured to stimulate an anti-inflammatory pathway 1496 for decreasing systemic pro-inflammatory processes and/or pro-inflammatory processes in one or more target organs 1498. The pathways, for example, may include a portion of the pathways illustrated in FIG. 1G. The first tissue location, for example, may include a surface of an ear structure contacted by an in-ear component of an auricular stimulation device. In some examples, the first electrode 220 of FIG. 2B, an electrode in the second member 408 of FIG. 4A, the electrode 503c of FIG. 5B, an electrode disposed on the anchoring structure 606 of FIG. 6, or the electrode 1202 of FIG. 12 may be used to provide the first stimulation. The first tissue location, in another example, may be a tissue location contacted by the tragus appendix 282 of FIG. 2E. In some embodiments, the first stimulation 1402 is supplied to multiple tissue locations. For example, the first stimulation 1402 may be applied to a first tissue location including a surface of an ear structure contacted by an in-ear component of an auricular stimulation device as well as to a second tissue location on a tragus of the ear (e.g., contacted by the tragus appendix 282).

Decreasing systemic pro-inflammatory processes and/or pro-inflammatory processes in one or more target organs 1498, in some implementations, involves modulating at least a portion of the anti-inflammatory pathway of FIG. 1G such that activity at the NTS is modulated affecting activity in efferent pathways through the celiac and parasympathetic ganglion, which in turn modulates activity in the spleen, lungs, gut, and/or heart such that an anti-inflammatory response is elicited.

In some implementations, the method 1490 includes providing a second stimulation 1494 at a second tissue location configured to stimulate the anti-inflammatory pathway 1496 for decreasing systemic pro-inflammatory processes and/or pro-inflammatory processes in one or more target organs 1498. Examples of target pathways and structures for stimulation of the second tissue location include those modulating activity at and/or on the auriculotemporal nerve, the lesser occipital nerve, and/or the great auricular nerve. The pathways, for example, may include a portion of the pathways illustrated in FIG. 1G. The second tissue location, for example, may be a tissue location contacted by one or more of the electrodes 222, 224, and/or 226 of the earpiece 202 of FIGS. 2A-2C.

In some embodiments, providing the first stimulation (1492) and providing the second stimulation (1494) involves providing a series of simultaneous and/or synchronized stimulation pulses to both the first tissue location and the second tissue location. Each of the first stimulation (1492) and the second stimulation (1494) may be applied using the same or different parameters. The parameters, in some examples, may include pulse frequency (e.g., low, mid-range, or high) or pulse width. Further, the parameters may indicate electrode pairs for producing biphasic pulses. In a first illustrative example, the first stimulation may be applied using a low frequency, while the second stimulation is applied using a mid-range frequency. Conversely, in a second illustrative example, the first stimulation may be applied using a mid-range frequency, while the second stimulation is applied using a low frequency. Other combinations of low, mid-range, and high frequency stimulations are possible depending upon the patient and the disorder being treated.

In other embodiments, the method 1490 includes automatically adjusting delivery of the therapy (e.g., adjusting one or more parameters) based on feedback received from the pulse generator or another computing device in communication with the pulse generator. The feedback, in some examples, may include a blood oxygen concentration, a breathing rate, a breathing variation and/or tidal volume.

In further embodiments, combinations of the methods 1401 and 1490 may be used to increase bronchi compliance 1408 while also decreasing systemic pro-inflammatory processes and/or pro-inflammatory processes in one or more target organs 1498. For example, the first stimulation 1402 of the method 1401 may be delivered synchronously or simultaneously with the second stimulation 1494 of the method 1490 or vice-versa. In another example, the therapy of the method 1401, including both the first stimulation 1402 and the second stimulation 1404 may be delivered for a first period of time, and the therapy of the method 1490 including both the first stimulation 1492 and the second stimulation 1494 may be delivered for a second period of time. The combined methods may be repeated for a number of cycles of the first period of time and the second period of time. Based on feedback, the length of one or both of the first period of time and the second period of time may be adjusted, to both increase bronchi compliance 1408 and decrease systemic pro-inflammatory processes and/or pro-inflammatory processes in one or more target organs 1498 in an efficient manner.

In an aspect, the stimulation targets specific neural targets in a local manner using bipolar stimulation. In an aspect, the system can be programmed for optimal therapy according to the needs of individual users including custom stimulation frequency, custom pulse width, custom stim intensity (amplitude), independently controlled stimulation channels. In some implementations, the treatment is configured to abate withdrawal symptoms including acute and/or chronic pain. In an aspect, pain control is due to modulation of endorphin, enkephalins, and/or dynorphins output in opioid related systems. In an example, the therapy can be provided during surgery, and/or post-surgery to reduce dependency of pain killer medications, including opioids, up to not needing medication at all.

In some implementations, devices and methods described herein promote reduction of opioid intake by incrementally reducing doses taken by a patient (e.g., provided by a medical professional or managed by the patient). Patients being prescribed long term opioid use for treatment of chronic pain eventually, at high doses, are susceptive to increased pain sensitivity/lack of efficacy, adverse events and/or symptoms, and/or a tendency toward harmful or hazardous (e.g., addictive) use of opioid medications. Chronic pain patients, such as cancer patients, may be provided a regimen of electrical stimulation for reducing dosage of the opioid drug over time. Further, since the reliance upon strong doses of opioid medication may be, in part, related to a cognitive disorder (e.g., phantom pains, etc.), systems and methods described herein that adjust functioning of the pre-frontal cortex, in particular, may adjust over-reliance on opioid medication by assisting the patient in improved recognition of, and decision-making related to, reliance on pharmaceutical support.

In one some embodiments, systems and methods described herein may be used to gradually reduce reliance upon opioid medications through periodic dose reduction (e.g., every day, every other day, etc.) of a morphine equivalent substance. The dosage may be provided as one of a number of morphine equivalent opioid substances such as, in some examples, Buprenorphine patch, Buprenorphine tab or film, Butorphanol, Codeine, Dihydrocodeine, Fentanyl buccal or SL tablets, or lozenge/troche, Fentanyl film or oral spray, Fentanyl nasal spray, Fentanyl patch, Hydrocodone, Hydromorphone, Levorphanol tartrate, Meperidine hydrochloride, Methadone, Morphine, Nalbuphine, Opium, Oxycodone, Oxymorphone, Pentazocine, Tapentadol, and/or Tramadol. The dose may be based on known morphine equivalent conversion factors. A physician, for example, may monitor and adjust stimulation therapy and patient pharmaceutical dosage of a morphine equivalent daily dose (MEDD) over a period of time, such as two to 5 days prior to surgery. For example, according to the veteran affairs opioid tapering protocol, a "fast taper" involves reducing dosage by 10% to 20% weekly, and a "rapid taper" involves reducing dosage immediately by 20 to 50%, followed by a 10 to 20% reduction each day for the following days.

In an illustrative example, stimulation therapy may be provided for at least one hour each session and at least two daily sessions for a minimum of two hours total stimulation time, coordinated with dosage reduction. The stimulation therapy may be repeated daily until the target dosage (or complete cessation of dosage) has been achieved. In some implementations, the stimulation therapy is continued after the target MEDD has been achieved, for example to assist the patient's brain to adjust to the lack of accustomed opioid level in the patient's system. Withdrawal symptoms may continue for seven to ten days after removal of the drug from the system, causing much pain and anxiety to the patient. By continuing stimulation for up to two weeks after the target MEDD has been achieved, incidents of withdrawal symptoms can be lessened or negated.

In example clinical results involving neonatal abstinence syndrome (NOWS), illustrated in Table 2, below, newborns were provided 30 minutes of Transcutaneous Auricular Neurostimulation (tAN™) prior to each scheduled MEDD administration. Jenkins, Dorothea D et al. "Transcutaneous Auricular Neurostimulation (tAN): A Novel Adjuvant Treatment in Neonatal Opioid Withdrawal Syndrome." Frontiers in human neuroscience vol. 15 648556. 8 Mar. 2021, doi: 10.3389/fnhum.2021.648556 The infants, categorized into tAN groupings, were exposed in utero to methadone, tobacco (tAN1); heroin, buprenorphine, cocaine, and tobacco (tAN2); buprenorphine (tAN3); opioids, methamphetamines, and benzodiazepines (tAN4); heroin, cocaine, and methadone (tAN5); heroin, methadone, tobacco, and THC (tAN6); hydromorphone (tAN7); and heroin, methamphetamines, methadone, and tobacco (tAN8). The mean (SD) control oral morphine dose was 0.076 (±0.041) mg/kg administered every 3 h. Id. at p. 5.

TABLE 2

| Outcome | Median (IQR) | Mean (SD) | Mean (SD) Excludes tAN6 (N = 7) | Range |
|---|---|---|---|---|
| Total oral morphine length of treatment (LOT) in days | 9.0 (6.5to12.8) | 13.3(12.8) | 9.0 (4.7) | (4-43) |
| Oral morphine length of treatment (LOT) after tAN initiation in days | 6.0 (4.8to 8) | 7.0(4.0) | 5.7 (1.9) | (3-16) |

Id. at p. 6.

As illustrated in Table 2, "the median LOT from the start of administering oral morphine (9 days) and the median LOT after tAN initiation (6.0 days) were both significantly lower than previously published data suggesting that the average NICU stay for infants undergoing pharmacotherapy for NOWS is 23 days." Id.

In some implementations, while engaged in a longer-term therapy, the patient may opt to switch from one ear to the other when replacing the earpiece for stimulation therapy. For example, a patient may apply a right earpiece on day 1, wear the earpiece overnight, conduct a morning therapy session, remove the earpiece before showering, and then apply a left earpiece for day 2. In other examples, patients may switch sides every other day, every few days, or remain with the earpiece on the same side, depending upon comfort. For example, a side sleeper who commonly sleeps on the left may opt to only apply an earpiece to the right side for comfort while sleeping.

In further embodiments, patients may obtain therapy with dual earpieces simultaneously applied. Therapy may be provided to both ears simultaneously, for example. In other embodiments, therapy may be alternated from the left to the right between therapy sessions.

Figure 12:
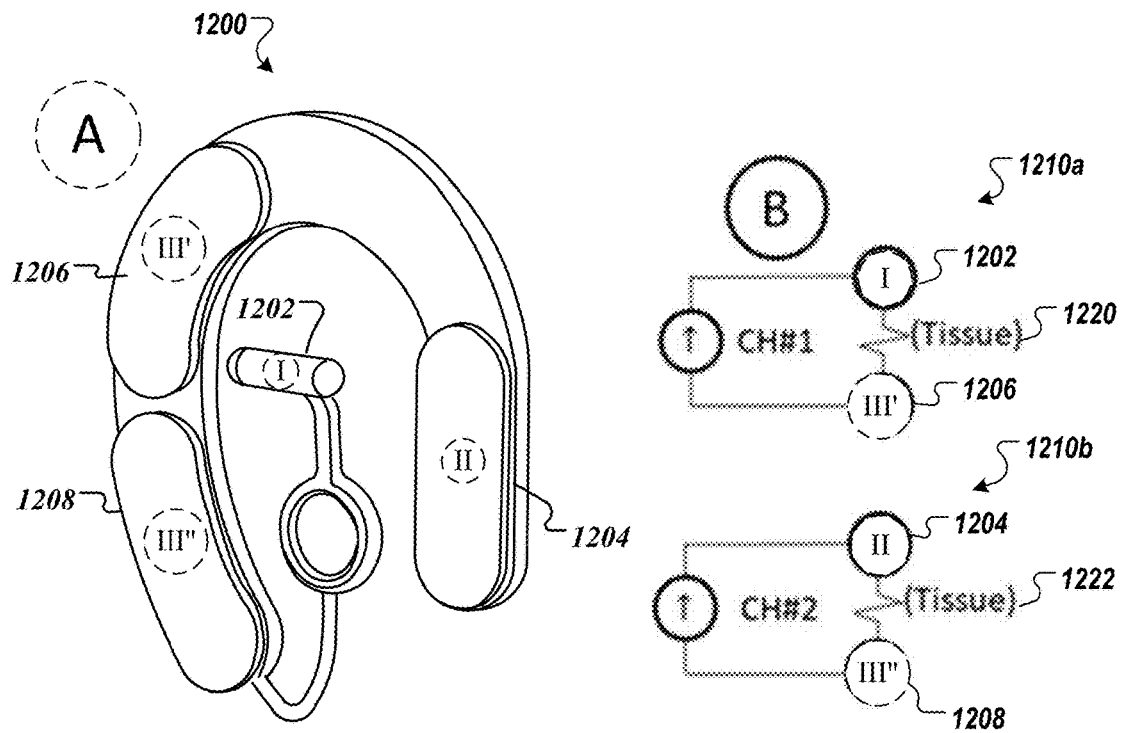
FIG. 12 is a drawing of an electrode configuration and equivalent circuit for providing therapy according to an example.

Turning to FIG. 12, an electrode configuration of an auricular component 1200 and equivalent circuits 1210a-b for providing therapy is shown according to an example. The auricular component 1200 is shown having electrodes 1202 (220), 1204 (222), 1206 (224), and 1208 (226) configured to form corresponding circuits 1210a-b according to an example. In an example, equivalent circuit 1210a is formed by electrode 1202 and electrode 1206 which are configured to stimulate tissue portion 1220. In this example, tissue portion 1220 is configured to target the cymba conchae region which is enervated by branches of the auricular branch of the vagus nerve and the region behind the ear which is enervated by branches of the great auricular nerve and branches of the lesser occipital nerve. In an example, equivalent circuit 1210b is formed by electrode 1204 and electrode 1208 which are configured to stimulate tissue portion 1222. In this example, tissue portion 1222 is configured to target the region rostral to the ear which is enervated by the Auriculotemporal nerve as well as the region behind the ear which is enervated by branches of the great auricular nerve and branches of the lesser occipital nerve.

In an example, the tissue portion 1220 can be the concha which is stimulated at approximately 5 Hz. In an example, the tissue portion 1220 can be the trigeminal nerve which is stimulated at approximately 100 Hz.

In an example, equivalent circuit 1210a is stimulated by a first channel and equivalent circuit 1210b is stimulated by a second channel.

Figure 13:
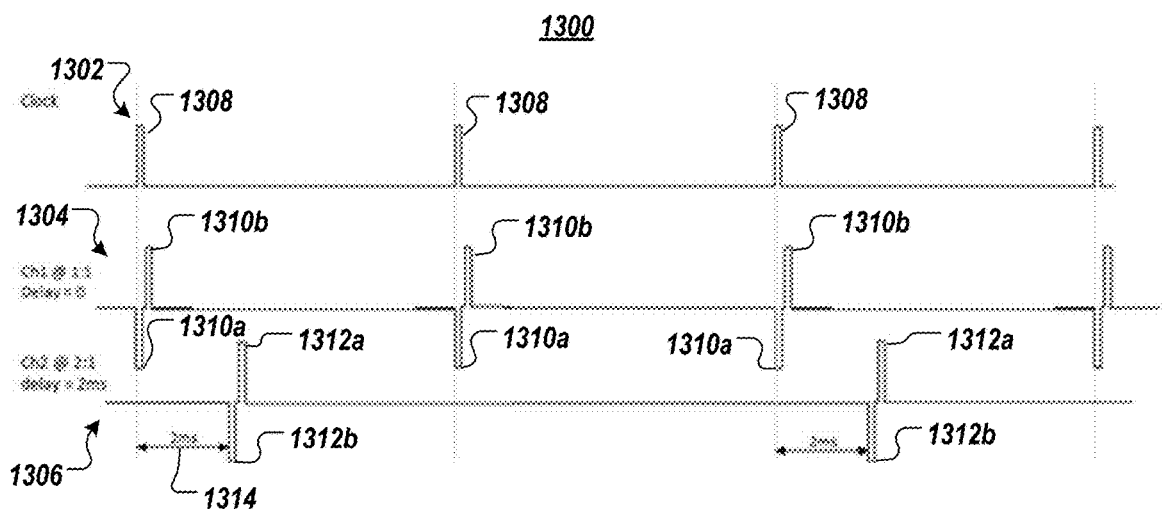
FIG. 13 is a drawing of a method for triggering multiple channels using a single clock according to an example.

FIG. 13 is a drawing of a timing diagram 1300 illustrating the triggering multiple channels 1304, 1306 using a master clock 1302 according to an example. In an exemplary embodiment, the clock 1302 triggers pulses 1308 at a predetermined clock frequency. In an example, a first channel 1304 can be configured to trigger stimulation 1310a-b of equivalent circuit 1210a and a second channel 1306 can be configured to trigger stimulation 1312a-b of equivalent circuit 1210b. In an example, the triggering can be reversed where equivalent circuit 1210b is triggered before equivalent circuit 1210a.

In an example, stimulation 1310a is configured to be triggered by every pulse of the master clock 1302; i.e., at a 1-to-1 ratio. In an example, stimulation 1310b is configured to be triggered following a specific time interval after the pulse in stimulation 1310a ends. In an example, stimulation 1312b is configured to be triggered every two pulses of the master clock 1302; i.e., at a 2-to-1 ratio with the master clock 1302. However, the triggering of stimulation 1312b occurs after a specific time delay after the master clock pulse 1314. In an example, stimulation 1312a is configured to be triggered following a specific time interval after the pulse in stimulation 1312b ends. In an example, stimulation 1310a is offset by stimulation 1312a by a synchronous delay 1314. In an example, the synchronous delay 1314 is preferably 2 ms and can be as little as zero (making both channels to trigger simultaneously depending on the master clock ratio for each channel) and as much as the master clock period less the combine duration of stimulation 1312b and 1312a plus the time interval between them. In some embodiments this delay can amount to 10 ms.

In some implementations, the equivalent circuits are synchronized using a master clock counter and a register per channel. By setting each register to a number of master clock pulses to trigger the respective channel, each channel is configured to be triggered when the channel register value equals the master clock pulses. Subsequently, the counter for each channel is reset after the channel is triggered. In an example, using a 6 bit counter and a 6 bit register, the trigger frequency can be as high as the master clock frequency (1:1) and as low as ¹⁄₆₄ of the clock frequency (64:1).

Stimulation delivery may vary based upon the therapy provided by the treatment device. Frequency and/or pulse width parameters, for example, may be adjusted for one or more if not all electrodes delivering stimulation. In some embodiments, frequency and/or pulse width parameters are adjusted during therapy, for example responsive to feedback received from monitoring the patient (e.g., using one or more sensors or other devices). The stimulation frequencies, in some examples, may include a first or low frequency within a range of about 1 to 30 Hz, a second or mid-range frequency within a range of about 30 to 70 Hz, and/or a third or high frequency within a range of about 70 to 150 Hz. Stimulation pulses, in some embodiments, are delivered in patterns. Individual pulses in the pattern may vary in frequency and/or pulse width. Patterns may be repeated in stimulation cycles.

In one embodiment, the stimulation patterns are such that stimulating frequencies are not the same in all electrodes. In one embodiment, a stimulation frequency is varied between 2 Hz and 100 Hz such that different endogenously produced opioid receptor agonist are released (e.g., Mu, Delta, Kappa, nociception opioid receptor agonist). In yet another embodiment, the pulse width can be adjusted from between 20 and 1000 microseconds to further allow therapy customization.

In some embodiments, different stimulation frequencies are used at the different electrodes. In illustration, different combinations of high, mid-range and low frequencies can be used at either a cymba electrode (e.g., 204), an auriculotemporal electrode (e.g., 222), and/or a great auricular nerve and lesser occipital nerve electrode (e.g., 224, 226). For example, a first or low frequency of between 1 to 30 Hz, or in particular one or more of 1 to 5 Hz, 5 to 10 Hz, 10 to 15 Hz, 15 to 20 Hz, 20 to 25 Hz, 25 to 30 Hz may be used at an in-ear electrode such as the cymba electrode 204, while a second of high frequency of between 70 and 150 Hz, or in particular one or more of 70 to 75 Hz, 75 to 80 Hz, 80 to 85 Hz, 85 to 90 Hz, 90 to 95 Hz, 95 to 100 Hz, 100 to 105 Hz, 105 to 110 Hz, 110 to 115 Hz, 115 to 120 Hz, 120 to 125 Hz, 125 to 130 Hz, 130 to 135 Hz, 135 to 140 Hz, 140 to 145 Hz, 145 to 150 Hz is used at tissue surrounding the ear, such as the auriculotemporal electrode 222. In another example, a third or mid-range frequency of between 30 to 70 Hz, or in particular one or more of 30 to 35 Hz, 35 to 40 Hz, 40 to 45 Hz, 45 to 50 Hz, 50 to 55 Hz, or 55 to 60 Hz or 60 to 65 Hz or 65 to 70 Hz can be used at one or more of the electrodes. In yet another example, one or more low or mid-range frequencies can be used at an in-ear electrode such as the cymba electrode 204, while one or more high frequencies is used at an electrode contacting tissue surrounding the ear, such as the auriculotemporal electrode 222. In other example, a high frequency can be used at an in-ear electrode such as the cymba electrode 204 while a low frequency can be used at an electrode contacting tissue surrounding the ear, such as the auriculotemporal electrode 222.

Different combination of pulse widths can be used at each electrode. Pulse widths, in some examples, may range from one or more of the following: first or short pulse widths within a range of about 10 to 50 microseconds, or more particularly between 10 to 20 microseconds, 20 to 30 microseconds, 30 to 40 microseconds, 40 to 50 microseconds; second or low mid-range pulse widths within a range of about 50 to 250 microseconds, or more particularly between 50 to 70 microseconds, 70 to 90 microseconds, 90 to 110 microseconds, 110 to 130 microseconds, 130 to 150 microseconds, 150 to 170 microseconds, 170 to 190 microseconds, 190 to 210 microseconds, 210 to 230 microseconds, or 230 to 250 microseconds; third or high mid-range pulse widths within a range of about 250 to 550 microseconds, or more particularly between 250 to 270 microseconds, 270 to 290 microseconds, 290 to 310 microseconds, 310 to 330 microseconds, 330 to 350 microseconds, 350 to 370 microseconds, 370 to 390 microseconds, 390 to 410 microseconds, 410 to 430 microseconds, 430 to 450 microseconds, 450 to 470 microseconds, 470 to 490 microseconds, 490 to 510 microseconds, 510 to 530 microseconds, or 530 to 550 microseconds; and/or fourth or long pulse widths within a range of about 550 to 1000 microseconds, or more particularly between 550 to 600 microseconds, 600 to 650 microseconds, 650 to 700 microseconds, 700 to 750 microseconds, 750 to 800 microseconds, 800 to 850 microseconds, 850 to 900 microseconds, 900 to 950 microseconds, or 950 to 1000 microseconds. Different embodiments can use different ranges of pulse widths at one or more of the electrodes (e.g., the electrodes 204, 222, 224, 226, 230, 282).

In yet another embodiment, a variable frequency (i.e., stimulating a non-constant frequency) can be used at one or more of the electrodes (e.g., 204, 222, 224, 226, 230, 282). The variable frequency can be a sweep, and/or a random/pseudo-random frequency variability around a central frequency (e.g., 5 Hz+/−1.5 Hz, or 100 Hz+/−10 Hz).

In one embodiment, the auricular component (e.g., 201, 600) is made with a single flexible board and/or printed electronics containing electronic components to uniquely identify it and, among other things, to counteract any inductance produced by the connecting cable. This flexible electronic circuit is over-molded onto a skin 502 allowing openings in it to allow direct contact with the back part of the skin-contacting electrodes 503. This auricular component 201, 600 is light-weight and extremely flexible allowing it to easily conform to different shapes presented by the anatomic variability of users. In one embodiment, the molded auricular component is not homogenic, changing the density and elasticity/flexibility at different places such that, for example, the part going around the ear is more flexible than the part going on the ear.

In other embodiment, the flexible electronic circuit 600 is covered with a flexible material such as a closed cell foam.

In one embodiment, the skin-contacting electrodes can be made for example of 3-layers, being the first layer a medical-grade double-sided conducting adhesive tape, the second layer a conductive flexible metallic and/or fabric mesh for mechanical robustness and homogenic electrical field distribution, and a third layer of self-adhesive hydrogel. A two-layer version is also possible in which both mechanical robustness and homogenic electrical field distribution is achieved by the first layer, rendering unnecessary the second layer described in the three-layer electrode.

In another embodiment, the PCB electrodes 503 are made such that they cover a similar surface area as the skin-contacting hydrogel electrodes; such that homogenic electrical field distribution is achieved at the hydrogels without the need of any additional conductive layer.

In an aspect, the system can record overall therapeutic delivery so the caregiver/clinician can measure compliance. In one embodiment, the management software notifies the wearer, caregiver, clinician if the device has stopped delivering therapy. In an example, the management software can be configured to report data related to use, events, logs, errors, and device health status. In an aspect, the system can provide usage reports. In an aspect, the system can have a uniquely identifiable auricular component 201 that can be used in identifying users and reported data. In an example, the device health status can report on the condition of the electrodes, the conductive hydrogel, and/or the analgesic.

In an exemplary embodiment, the system utilizes feedback to monitor and/or modify the therapy. The feedback may be obtained from one or more sensors capable of monitoring one or more symptoms being treated by the therapy. For example, upon reduction or removal of one or more symptoms, a therapeutic output may be similarly reduced or ceased. Conversely, upon increase or addition of one or more symptoms, the therapeutic output may be similarly activated or adjusted (increased, expanded upon, etc.). In some examples, the sensors may monitor one or more of electrodermal activity (e.g., sweating), movement activity (e.g., tremors, physiologic movement), glucose level, neurological activity (e.g., via EEG), and/or cardiopulmonary activity (e.g., EKG, heart rate, blood pressure (systolic, diastolic and mean)). Imaging techniques such as MRI and fMRI could be used to adjust the therapy in a clinical setting for a given user. In other embodiments, imaging of pupillary changes (e.g., pupillary dilation) using, for example a common cellular phone and/or smart-glass glasses could be used to provide feedback to make therapy adjustments. In some implementations, one or more sensors are integrated into the earpiece and/or concha apparatus. One or more sensors, in some implementations, are integrated into the pulse generator. For example periodic monitoring may be achieved through prompting the wearer to touch one or more electrodes on the system (e.g., electrodes built into a surface of the pulse generator) or otherwise interact with the pulse generator (e.g., hold the pulse generator extended away from the body to monitor tremors using a motion detector in the pulse generator). In further implementations, one or more sensor outputs may be obtained from external devices, such as a fitness computer, smart watch, or wearable health monitor.

The monitoring used may be based, in part, on a treatment setting. For example, EEG monitoring is easier in a hospital setting, while heart rate monitoring may be achieved by a sensor such as a pulsometer built into the earpiece or another sensor built into a low budget health monitoring device such as a fitness monitoring device or smart watch.

In an illustrative example, feedback related to electrodermal activity could be used to monitor and detect a speed or timing of a symptom and/or therapeutic outcome. In an example, the electrodermal activity could be sensed by electrodes on the auricular component 201. In another example, the electrodermal activity could be detected by electrodes on another portion of the body and communicated to the system.

In some implementations, the system can further include one or more motion detectors, such as accelerometers or gyroscopes, that can be used gather information to modulate the therapy. In an example, the one or more motion detectors are configured to detect a tremor and/or physiologic movement. In an aspect, the tremor and/or the physiologic movement can be indicative of at least one of the underlying condition and the treatment to the underlying condition. In an example, the tremor and/or physiologic movement can be indicative of symptoms associated with substance withdrawal. In an aspect, feedback from glucose monitoring can be used to modulate the therapy.

In yet other implementations, EKG can be used to assess heart rate and heart rate variability, to determine the activity of the autonomic nervous system in general and/or the relative activity of the sympathetic and parasympathetic branches of the autonomic nervous system, and to modulate the therapy. Autonomic nervous activity can be indicative of symptoms associated with substance withdrawal. In an aspect, the treatment device can be used to provide therapy for treating cardiac conditions such as atrial fibrillation and heart failure. In an example, therapy can be provided for modulation of the autonomic nervous system. In some implementations, the treatment device can be used to provide therapy to balance a ratio between any combinations of the autonomic nervous system, the parasympathetic nervous system, and the sympathetic nervous system.

In an aspect, the system can monitor impedance measurements allowing closed-loop neurostimulation. In an example, monitoring feedback can be used to alert patient/caregiver if therapy is not being adequately delivered and if the treatment device is removed.

Figure 15:
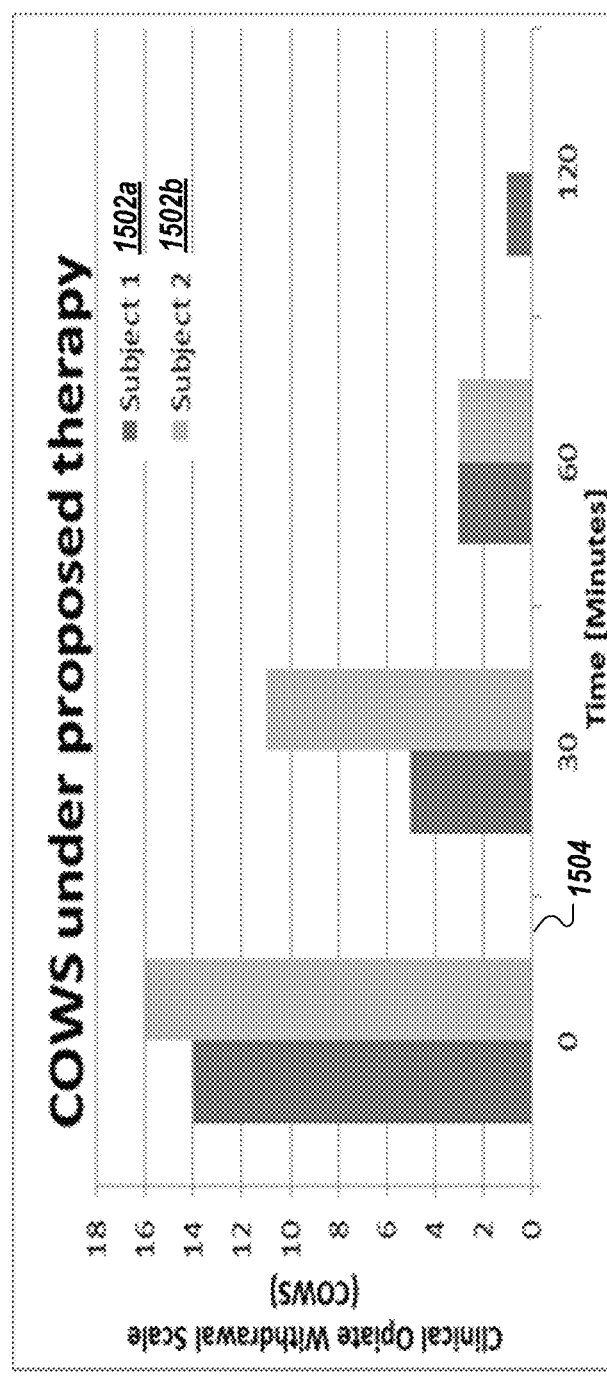
FIG. 15 is a bar graph showing data collected using the proposed system according to an example.

Turning to FIG. 15, a graph 1500 is shown of data collected using the proposed system according to an example. Clinical Opiate Withdrawal Score (COWS) over time was collected from two subjects 1502a. 1502b being treated with the proposed therapy. Therapy included using Low frequency (5 Hz) between the cymba electrode 204 and an electrode 224, and High frequency (100 Hz) between the auriculotemporal electrode 222 and electrode 226. As illustrated, the COWS score dramatically decreased over time 1504, in particular within the first 30-60 minutes.

Treatments that increase the availability of monoamine neurotransmitters such as Serotonin (5-HT) as well as Norepinephrine (NE) have shown to be effective in treating and controlling depression in a synergistic manner. For example, implanted vagal stimulation (VNS) and independent stimulation of the supraorbital nerve, which is part of the trigeminal system, have been used to treat depression-like symptoms. However, prescription medications, instead of increasing serotonin, rely on blocking the re-uptake of serotonin. NE and 5-HT are respectively produced in the Locus Coeruleus (LC) and in the Raphe Nucleus (RN), illustrated in the neural circuit of FIG. 1C. These two brain regions are integral parts of the Endogenous Opioid Circuits (EOC). Activity in both of these brain regions (or brain areas) can be modulated by activating afferent pathways to the EOC such as some trigeminal and vagal branches, for example using devices described herein. In this manner, a usable take-home solution involving increase of monoamine neurotransmitters, rather than the traditional pharmaceutical uptake blocking, may increase effectiveness of depression treatment in an outpatient environment.

Further demonstrating the previously mentioned link between the EOC, cognition, and depression, studies have shown that some antidepressants promote neurogenesis likely via the upregulation of Brain-Derived Neurotrophic-Factor (BDNF) in areas such as the hippocampus and the prefrontal cortex (PFC). BDNF plays a strong role in cognition, plasticity, neurogenesis, and neuronal survival. 5-HT has also been shown to have a role in such physiological activities. Furthermore, patients suffering from depression have been shown to have decreased plasma levels of BDNF, suggesting that depressive conditions would benefit from a therapy that could increase BDNF levels. Additionally, learning and memory as well as cortical plasticity is modulated by stimulation of vagal afferents through the synergetic action of ACh, 5-HT and BDNF. Further, acute vagal stimulation has been shown to increase NE and 5-HT release in the PFC and the amygdala as well as to enhance synaptic transmission in the hippocampus.

The cognitive improvement due to the increase in BDNF, which leads to a faster reorganization of neural circuits, can be leveraged not only to learn new things faster, but also to eliminate/extinguish undesirable and/or maladaptive behavior such as, in some examples, PTSD, phobias, and addictive behavior such as drug-seeking.

Also, it has been shown that vagal activation produces pairing-specific plasticity, thus stimulation of vagal afferents irrespective of what neuromodulator is produced can be used to eliminate and/or extinguish undesirable and/or maladaptive behavior such as those described above.

In another example, the cognitive enhancement provided by the systems and methods described herein can be used to overcome the cognitive problems that have been described to occur in people exposed to microgravity environments such as astronauts in the space station or on a long space travel such as visiting Mars.

Additionally, BDNF levels have been shown to have an inverse correlation with factors associated with cognitive decline and/or impediments, such as in Alzheimer's patients.

Turning to FIG. 16A through FIG. 16D, example processes are illustrated for providing direct or indirect modulation of neural pathways to treat disorders such as depression, PTSD, phobias, and/or addictive behaviors by increasing BDNF levels and monoamine neurotransmitter availability is illustrated. In particular, a process 1600 of FIG. 16A exploits a relationship between BDNF and 5-HT where BDNF promotes (1602) differentiation and survival of 5-HT neurons and, in turn, 5-HT availability upregulates BDNF (1604) gene expression. By applying the processes of FIG. 16A through FIG. 16D to electrical stimulation of a patient, the therapy may result in increasing the patient's control over the decision process by shifting the balance from impulsive decision to contemplative decision, allowing the patient to better weigh benefits with consequences of their actions. The therapy, in some examples, may include the treatment of depression, post-traumatic stress disorder (PTSD), and/or addiction. With the cognitive process bolstered by the increased BDNF levels and monoamine neurotransmitter availability as well as ACh, in some examples, the patient may be more likely to actively engage in counseling and/or be more receptive to therapy, experience an increased ability to apply coping mechanisms or behavior redirection techniques to counter the depression cycle, and/or demonstrate the ability to reduce intake of or be weaned from prescribed pharmaceutical therapies. Further, patients overcoming addictive disorders such as alcohol and/or tobacco addiction may experience reduced incidents of cravings and/or be better prepared to avoid succumbing to such cravings. Regarding tobacco addiction, as discussed above in relation to bronchial inflammation, the stimulation therapy represented in the examples provided by the processes of 16A through 16D, alone or in combination with stimulation therapies described above, may experience reduced inflammation and/or accelerated recovery from bronchial inflammation disorders caused by smoke inhalation such as COPD.

Figure 16A:
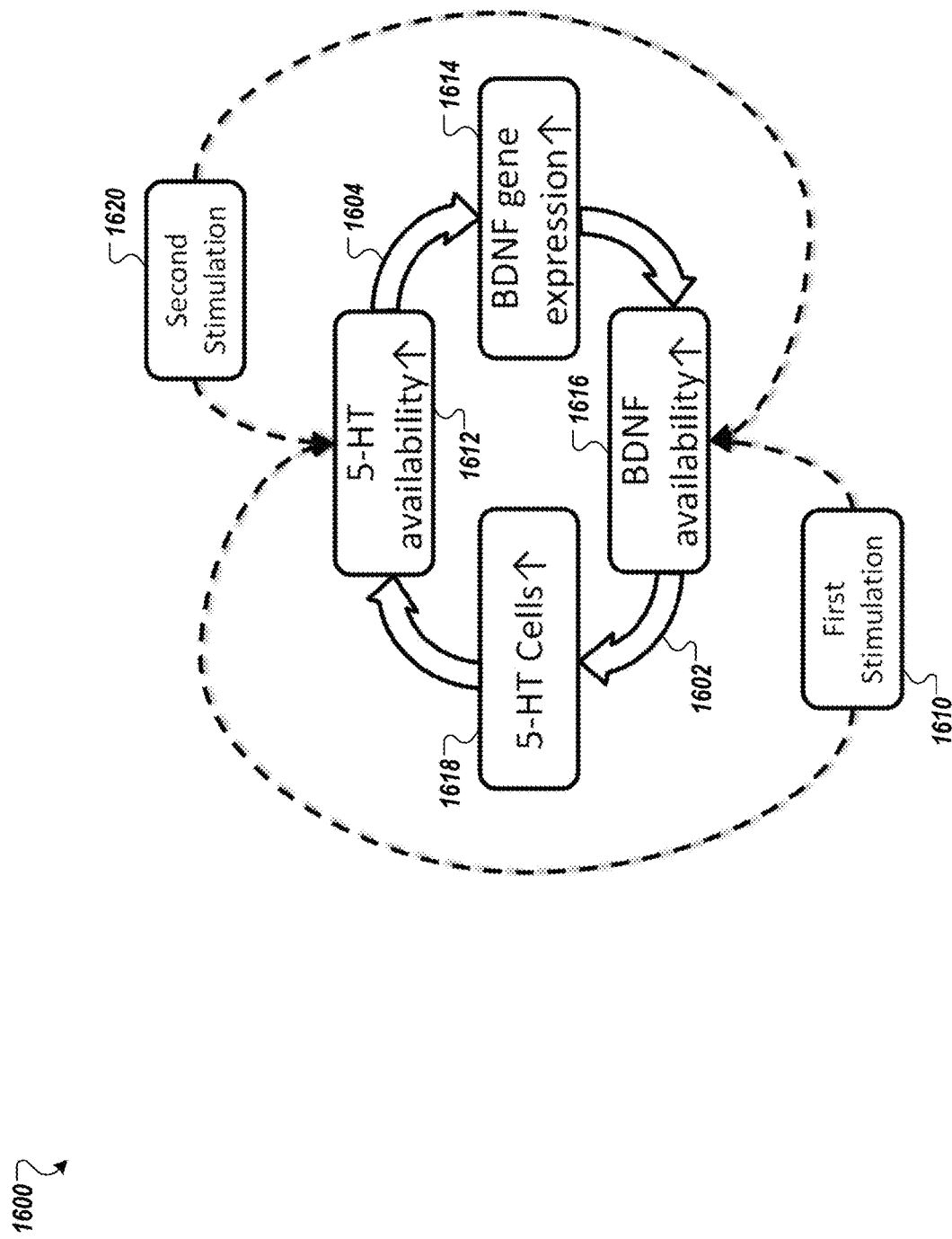
FIGS. 16A through 16D illustrate example processes for providing direct or indirect modulation of neural pathways to treat disorders such as depression, PTSD, phobias, and/or addictive behaviors by increasing BDNF levels and monoamine neurotransmitter availability.
Figure 16C:
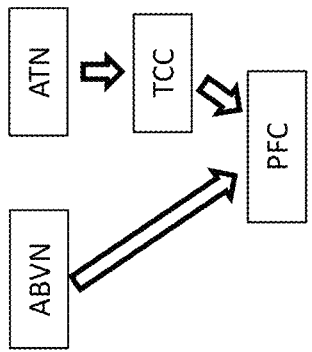
Figure 16B:
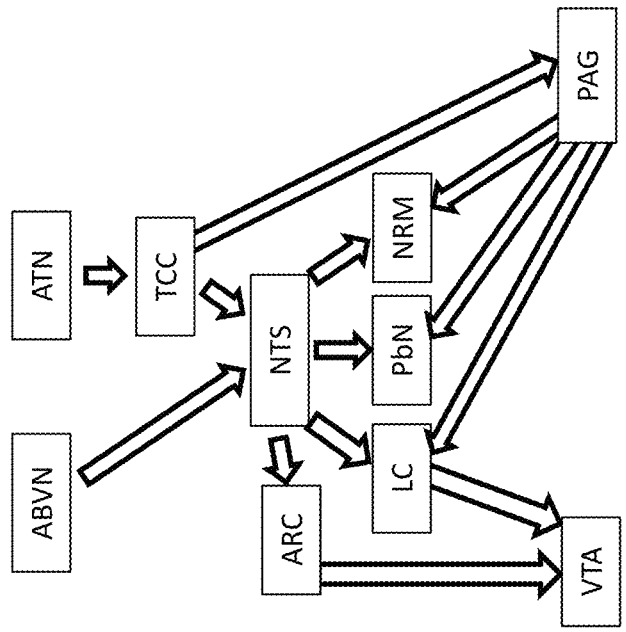
Figure 16D:
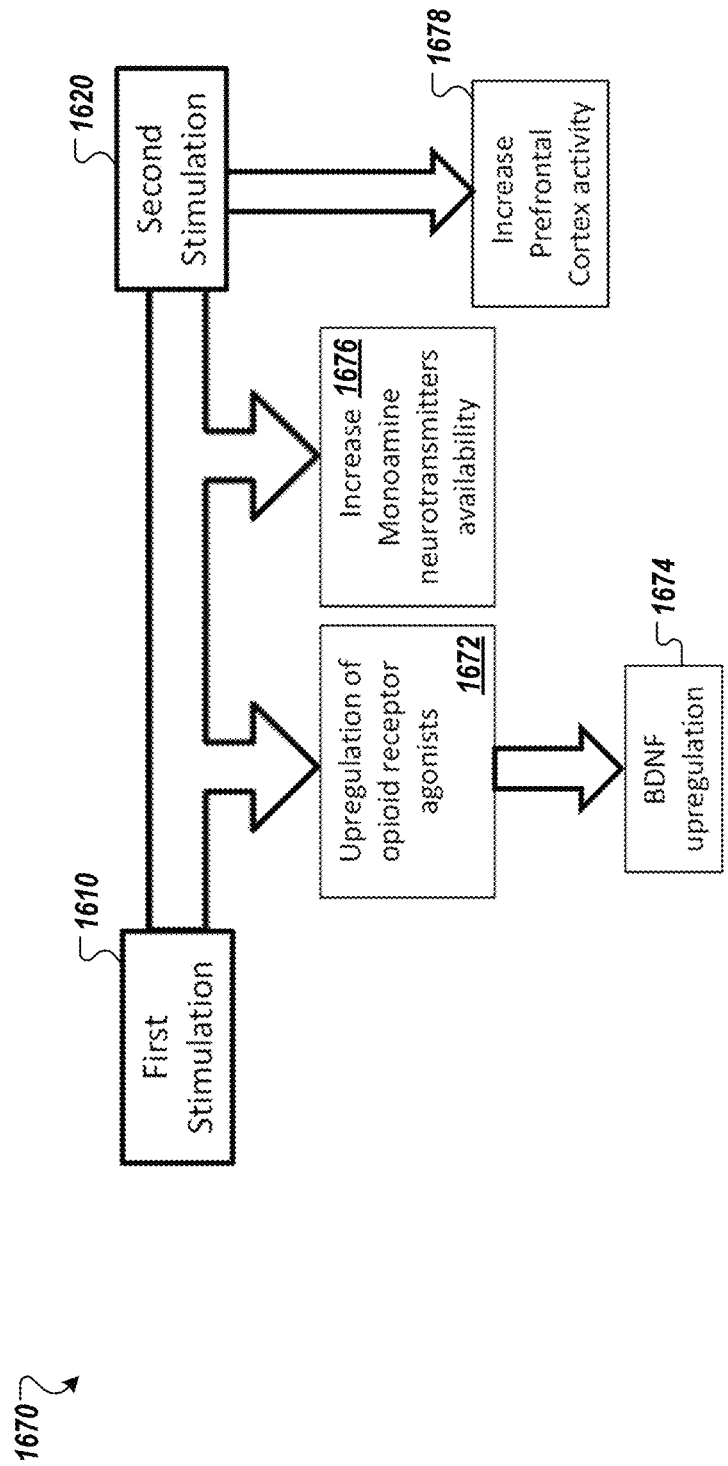

Turning to FIG. 16D, responsive to the first stimulation 1610, for example, BDNF levels may be upregulated by endogenous opioid agonists (EOA) (e.g., μ-opioid receptor agonists i.e., MOR agonists and/or δ-opioid receptor agonists i.e., DOR agonists) 1672. For example, Enkephalins may increase BDNF mRNA expression in the hippocampus mediated by DOR and MOR mechanisms and β-Endorphin, while endomorphin-1 and endomorphin-2 upregulate BDNF mRNA in the prefrontal cortex, hippocampus and amygdala 1674. Production of DA in the Ventral Tegmental Area (VTA) can be augmented by an increase in MOR agonist (e.g., endorphins and enkephalins); in particular by inhibiting GABAergic interneurons which in turn inhibit dopaminergic neurons in the VTA. Amongst other, these DAergic VTA neurons project to Nucleus Accumbens (NAc), the Prefrontal Cortex (PFC), the Hippocampus (Hipp), and the Amygdala (Amyg). These brain regions also share projections/connections amongst themselves making an important neuronal circuit known as the Reward Circuit or Reward Neural Circuit. Alterations leading to dysregulation, maladaptive regulation, or dysfunctional interactions in this neural circuit are seen in people with behaviors such as addiction, PTSD and depression. Furthermore, a dysregulation in this circuit has also been observed in people showing behaviors associated with lower attention levels, for example in attention deficit disorder (ADD) and attention deficit hyper-activity deficit disorder (ADHD).

Poor vagal tone and dysregulation in the activity between the PFC and the amygdala has been shown to be associated with anxiety disorders, including PTSD. Interestingly, activation of the PFC during vagal stimulation is correlated with positive patient outcomes.

Further, in some implementations, the first stimulation 1610 increases BDNF availability 1616, leading to promoting (1602) differentiation and survival of 5-HT neurons and 5-HT cells 1618. Turning to FIG. 16D, in the first stimulation 1610 may increase availability of monoamine neurotransmitters 1676, such as 5-HT and DA, leading to an increase in BDNF expression. The BDNF, in turn, may function to protect monoamine neurotransmitter neurons and assist the monoamine neurotransmitter neurons to differentiate.

Returning to FIG. 16A, in some implementations, the second stimulation 1620 increases BDNF availability. Turning to FIG. 16C, for example, BDNF may be upregulated through stimulation along example pathways 1650. According to the pathways 1650, the first stimulation 1610 may be configured to stimulate the ABVN which projects to the prefrontal cortex and/or the ATN which has a pathway to the prefrontal cortex via the TCC. The pathways 1650 result in modulating the "go/no-go center" of the brain which, when impaired, contributes to depression, cravings, and impulsiveness.

Turning to FIG. 16D, the second stimulation 1620, in some embodiments, increases prefrontal cortex activity 1678. The Prefrontal Cortex (PFC) is part of the Reward Circuit. The PFC plays an important role in the go/no-go decision-making process. That is, the reward or lack thereof is contrasted with the perceived risk of an action or a thought. The PFC is heavily involved in the process of deciding to act (go) or not act (no-go). As such, it is also involved in motivation, as the reward/risk balance is assessed against the person's goals and desires. Activity in the PFC has been shown to be lower than normal in individuals suffering from or experiencing depression. Study results comparing the anti-depressive properties of invasive electrostimulation suggest that targeting the PFC produces the most robust anti-depressant effects. For example, deep brain stimulation (DBS) in the PFC improves mood in people suffering from depression; additionally, non-invasive neuromodulation using Transcranial Magnetic Stimulation (TMS) targets the PFC to alleviate depression-like symptoms. Long-term stimulation of the trigeminal nerve has been shown to increase PFC activity.

In addiction, the dysregulation in the PFC Reward Circuit results in bias towards a more immediate reward; manifested in a more impulsive decision instead of a more controlled decision. The more impulsive behavior involves the DA network and tends to favor pleasure-seeking behavior. One manifestation of such behavior in addiction is reflected by a heightened attention to drug cues and cravings. This heightened attention to drug cues and cravings constitutes a heightened preoccupation/anticipation. The more controlled decision involves parts of the Reward Circuit like the PFC which provides control over goal-oriented tasks and self-regulation vs. impulsive behavior. The cravings experienced by individuals suffering from addiction reflect this bias towards more impulsiveness and less self-regulated behavior. Interestingly, studies of people suffering from addiction have shown a decrease in PFC activity. Transcranial direct current stimulation (tDCS) over portions of the PFC, for example, have shown an improvement of self-regulated vs. impulsive decision making and a reduction in cravings. Since the second stimulation 1620 can be used to interact with the Reward Circuit by interacting with the DA network and can be used to increase PFC activity 1678, the processes illustrated in FIGS. 16A-16D can be used to achieve a reduction in cravings and impulsive decision-making behavior.

Returning to FIG. 16A, as illustrated, applying the first stimulation 1610 and the second stimulation 1620 generates a virtuous-circle in which activation of the EOC increases 5-HT and EOA, 5-HT stimulates BDNF gene expression while EOA increases BDNF release, and in turn BDNF increase promotes survival and differentiation of 5-HT neurons which increases the availability of 5 HT neurons, thereby allowing a higher level of 5-HT to be produced and thus increasing BDNF gene availability which under the presence of EOA leads to higher BDNF levels. Increases in BDNF leads to cognitive enhancement/improvement, for example in learning and memory acquisition. Increases in BDNF have also shown to have neuroprotective effects.

In some embodiments, providing the first stimulation (1610) and providing the second stimulation (1620) involves providing a series of simultaneous and/or synchronized stimulation pulses. Each of the first stimulation (1610) and the second stimulation (1620) may be applied using the same or different parameters. The parameters, in some examples, may include pulse frequency (e.g., low, mid-range, or high) and/or pulse width. Further, the parameters may indicate electrode pairs for producing biphasic pulses. In a first illustrative example, the first stimulation may be applied using a low frequency, while the second stimulation is applied using a mid-range frequency. Conversely, in a second illustrative example, the first stimulation may be applied using a mid-range frequency, while the second stimulation is applied using a low frequency. Other combinations of low, mid-range, and high frequency stimulations are possible depending upon the patient and the disorder being treated. Therapy may be optimized according to the needs of individual patients including custom stimulation frequency, custom pulse width, custom stimulation intensity (amplitude), and/or independently controlled stimulation channels.

Figures 17A, 17B:
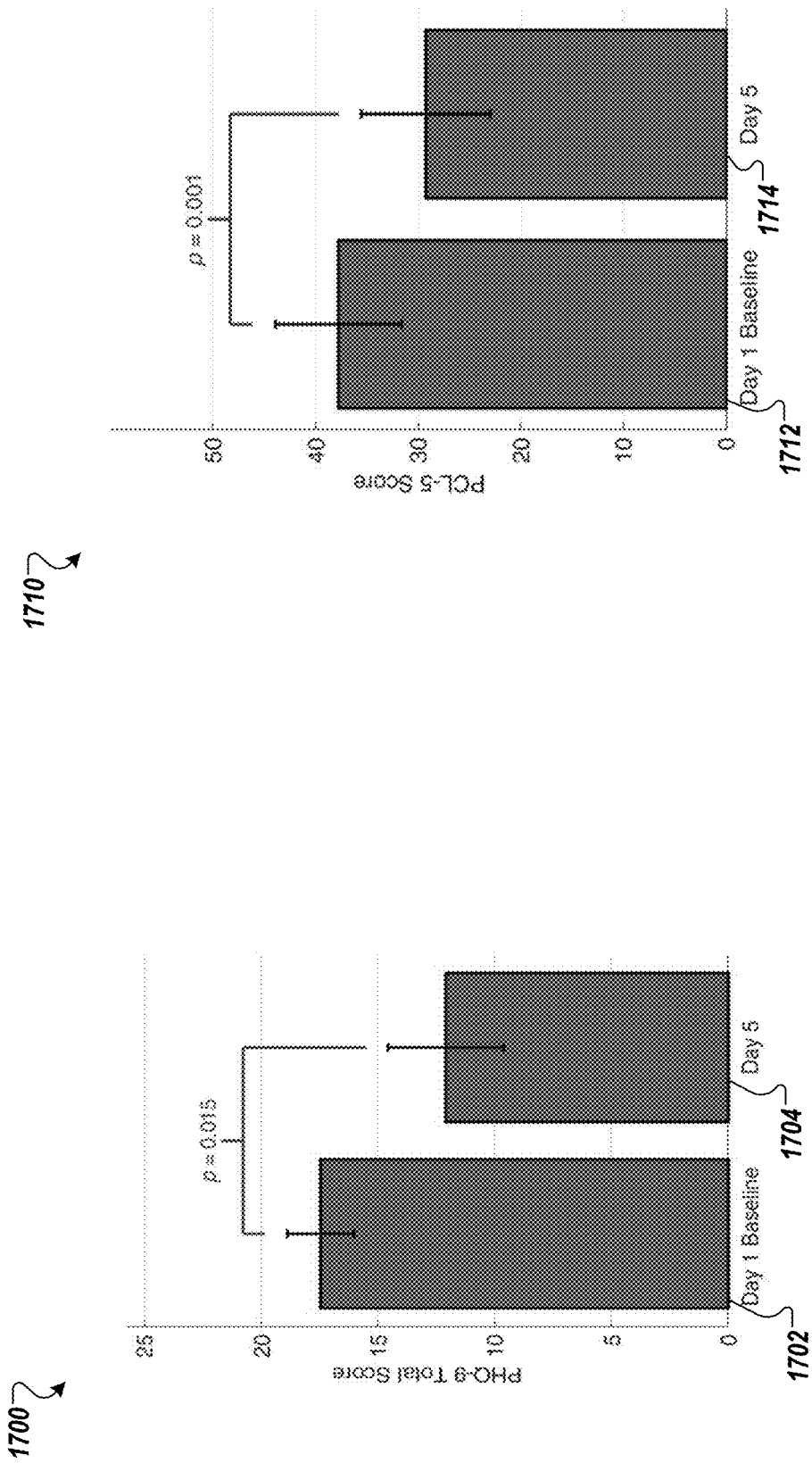
FIG. 17A and FIG. 17B are bar graphs showing data collected when applying stimulation to treat depression and PTSD according to an example.

FIG. 17A and FIG. 17B illustrate results of a clinical trial involving patients with depression and/or PTSD who were provided therapeutic stimulation over the course of five days. As illustrated in FIG. 17A, a graph 1700 demonstrates a reduction of depression-related symptoms between a first day baseline 1702 and a fifth day level 1704. Turning to FIG. 17B, a graph 1710 demonstrates a reduction in PTSD-related symptoms between a first day baseline 1712 and a fifth day level 1714. Table 3, below, provides metrics related to the results of the study.

TABLE 3

| Questionnaire | Mean(SD) Reduction in Score from Baseline to Day 5 (N = 13) | Percent Change in Score from Baseline to Day 5 (N = 13) | P value | Percentage of Participants with Clinically Meaningful Reduction |
|---|---|---|---|---|
| PHQ-9 (Depression) | 5.4(6.1) | 31.4 (35.7)% | 0.015 | 6/13 (46.2%) |
| PCL-5 (PTSD) | 10.2(9.1) | 31.4 (33.4)% | 0.001 | 5/13 (38.5%) |

Reference has been made to illustrations representing methods and systems according to implementations of this disclosure. Aspects thereof may be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/operations specified in the illustrations.

One or more processors can be utilized to implement various functions and/or algorithms described herein. Additionally, any functions and/or algorithms described herein can be performed upon one or more virtual processors, for example on one or more physical computing systems such as a computer farm or a cloud drive.

Aspects of the present disclosure may be implemented by hardware logic (where hardware logic naturally also includes any necessary signal wiring, memory elements and such), with such hardware logic able to operate without active software involvement beyond initial system configuration and any subsequent system reconfigurations. The hardware logic may be synthesized on a reprogrammable computing chip such as a field programmable gate array (FPGA), programmable logic device (PLD), or other reconfigurable logic device. In addition, the hardware logic may be hard coded onto a custom microchip, such as an application-specific integrated circuit (ASIC). In other embodiments, software, stored as instructions to a non-transitory computer-readable medium such as a memory device, on-chip integrated memory unit, or other non-transitory computer-readable storage, may be used to perform at least portions of the herein described functionality.

Various aspects of the embodiments disclosed herein are performed on one or more computing devices, such as a laptop computer, tablet computer, mobile phone or other handheld computing device, or one or more servers. Such computing devices include processing circuitry embodied in one or more processors or logic chips, such as a central processing unit (CPU), graphics processing unit (GPU), field programmable gate array (FPGA), application-specific integrated circuit (ASIC), or programmable logic device (PLD). Further, the processing circuitry may be implemented as multiple processors cooperatively working in concert (e.g., in parallel) to perform the instructions of the inventive processes described above The process data and instructions used to perform various methods and algorithms derived herein may be stored in non-transitory (i.e., non-volatile) computer-readable medium or memory. The claimed advancements are not limited by the form of the computer-readable media on which the instructions of the inventive processes are stored. For example, the instructions may be stored on CDs, DVDs, in FLASH memory, RAM, ROM, PROM, EPROM, EEPROM, hard disk or any other information processing device with which the computing device communicates, such as a server or computer. The processing circuitry and stored instructions may enable the pulse generator 210 of FIGS. 2A-2C, the pulse generator 1004 of FIGS. 10A-10C, or the pulse generator 1150 of FIG. 11 to perform various methods and algorithms described above. Further, the processing circuitry and stored instructions may enable the peripheral device(s) 1010 of FIGS. 10A-10C to perform various methods and algorithms described above.

These computer program instructions can direct a computing device or other programmable data processing apparatus to function in a particular manner, such that the instructions stored in the computer-readable medium produce an article of manufacture including instruction means which implement the function/operation specified in the illustrated process flows.

Embodiments of the present description rely on network communications. As can be appreciated, the network can be a public network, such as the Internet, or a private network such as a local area network (LAN) or wide area network (WAN) network, or any combination thereof and can also include PSTN or ISDN sub-networks. The network can also be wired, such as an Ethernet network, and/or can be wireless such as a cellular network including EDGE, 3G, 4G, and 5G wireless cellular systems. The wireless network can also include Wi-Fi, Bluetooth, Zigbee, or another wireless form of communication. The network, for example, may be the network 1020 as described in relation to FIGS. 10A-10C.

The computing device, such as the peripheral device(s) 1010 of FIG. 10A-10C, in some embodiments, further includes a display controller for interfacing with a display, such as a built-in display or LCD monitor. A general purpose I/O interface of the computing device may interface with a keyboard, a hand-manipulated movement tracked I/O device (e.g., mouse, virtual reality glove, trackball, joystick, etc.), and/or touch screen panel or touch pad on or separate from the display.

A sound controller, in some embodiments, is also provided in the computing device, such as the peripheral device(s) 1010 of FIG. 10A-10C, to interface with speakers/microphone thereby providing audio input and output.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry or based on the requirements of the intended back-up load to be powered.

Certain functions and features described herein may also be executed by various distributed components of a system. For example, one or more processors may execute these system functions, where the processors are distributed across multiple components communicating in a network such as the network 1020 of FIGS. 10A-10C. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process.

Although provided for context, in other implementations, methods and logic flows described herein may be performed on modules or hardware not identical to those described. Accordingly, other implementations are within the scope that may be claimed.

In some implementations, a cloud computing environment, such as Google Cloud Platform™, may be used perform at least portions of methods or algorithms detailed above. The processes associated with the methods described herein can be executed on a computation processor of a data center. The data center, for example, can also include an application processor that can be used as the interface with the systems described herein to receive data and output corresponding information. The cloud computing environment may also include one or more databases or other data storage, such as cloud storage and a query database. In some implementations, the cloud storage database, such as the Google Cloud Storage, may store processed and unprocessed data supplied by systems described herein.

The systems described herein may communicate with the cloud computing environment through a secure gateway. In some implementations, the secure gateway includes a database querying interface, such as the Google BigQuery platform.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A method for treating cognitive dysfunction and/or depression using transcutaneous auricular neurostimulation therapy, the method comprising:
   providing a wearable neurostimulation device, the wearable neurostimulation device comprising
      a first portion configured for positioning along a portion of skin behind a back of the ear of the patient, wherein the first portion is configured to extend over the ear, the first portion comprising
         at least one first electrode configured to electrically stimulate at least one branch of the auriculotemporal nerve via non-piercing contact with tissue in front of the ear and surrounding the ear, and
         an electrical connector, and
      a second portion in electrical communication with the first portion, the second portion being configured to engage a concha and/or tragus region of the ear of the patient, the second portion comprising at least one second electrode configured to electrically stimulate at least one auricular branch of the vagus nerve via non-piercing contact with tissue of the concha or tragus of the ear;
   positioning the wearable neurostimulation device about an ear of a patient such that
      i) the first portion is disposed against the back of the ear and over the ear with the at least one first electrode in non-piercing contact with the tissue in front of the ear and surrounding the ear, and
      ii) the second portion is engaging the concha region and/or the tragus region of the ear of the patient with the at least one second electrode in non-piercing contact with the tissue of the concha or tragus of the ear;

connecting the wearable neurostimulation device, via the electrical connector of the first portion of the wearable neurostimulation device, to a pulse generator comprising circuitry configured to provide stimulation pulses; and delivering, via the wearable neurostimulation device, the transcutaneous auricular neurostimulation therapy comprising the stimulation pulses, wherein delivering comprises delivering a first series of the stimulation pulses to the at least one first electrode, the first series of the stimulation pulses being configured to increase monoamine neurotransmitter availability, and delivering a second series of the stimulation pulses to the at least one second electrode, the second series of the stimulation pulses being configured to upregulate opioid receptor agonists.

2. The method of claim 1, further comprising repeating the transcutaneous auricular neurostimulation therapy at least once daily over one or more days.

3. The method of claim 2, wherein:

at least a portion of the wearable neurostimulation device is disposable; and repeating the transcutaneous auricular neurostimulation therapy comprises, prior to delivering the transcutaneous auricular neurostimulation therapy on at least a portion of the repeated deliveries, replacing the portion of the wearable neurostimulation device with a new wearable neurostimulation device portion or new wearable neurostimulation device.

4. The method of claim 2, wherein:

the wearable neurostimulation device is designed to be worn on one of a right ear or a left ear; and repeating the transcutaneous auricular neurostimulation therapy comprises, prior to delivering on at least a portion of the repeated deliveries, replacing the wearable neurostimulation device with another wearable neurostimulation device designed to be worn on an opposite of the right ear or the left ear.

5. The method of claim 2, further comprising providing, to the patient each day for at least a first day of the one or more days, a tapering medication.

6. The method of claim 5, wherein providing the tapering medication comprising reducing a dosage of the tapering medication over a time period until a target dosage is reached.

7. The method of claim 6, wherein the target dosage is no tapering medication.

8. The method of claim 1, wherein the patient is an infant, the method further comprising:

monitoring, by a health care provider, exhibition of any of a set of symptoms in the patient; and after identifying, by the health care provider, one or more symptoms of the set of symptoms, manually adjusting at least one parameter of the transcutaneous auricular neurostimulation therapy.

9. The method of claim 1, wherein positioning comprises adhesively applying the first portion of the wearable neurostimulation device around the back of the ear.

10. The method of claim 1, wherein positioning comprises frictionally retaining the second portion of the wearable neurostimulation device in the concha region of the ear.

11. The method of claim 1, wherein the transcutaneous auricular neurostimulation therapy is configured to treat at least one of depression, PTSD, addictive behavior, or phobia.

12. The method of claim 11, wherein the transcutaneous auricular neurostimulation therapy is configured to treat the addictive behavior, wherein the addictive behavior comprises at least one of smoking, substance use disorder, opioid use disorder, or alcohol use disorder.

13. The method of claim 11, wherein treating the addictive behavior comprises preventing relapse and/or reducing cravings.

14. The method of claim 1, wherein the first series of the stimulation pulses and/or the second series of the stimulation pulses is further configured to increase prefrontal cortex activity.

15. A method for treating cognitive dysfunction and/or depression using transcutaneous auricular neurostimulation therapy, the method comprising:

providing a wearable neurostimulation device about an ear of a patient, the wearable neurostimulation device comprising a first portion configured for positioning along a portion of skin behind a back of the ear of the patient, wherein the first portion is configured to extend over the ear, the first portion comprising at least one first electrode configured to electrically stimulate at least one branch of the auriculotemporal nerve via non-dermal-penetrating contact with tissue in front of the ear and surrounding the ear, and an electrical connector, and a second portion in electrical communication with the first portion, the second portion being configured to engage a concha region and/or tragus of the ear of the patient, the second portion comprising at least one second electrode configured to electrically stimulate at least one auricular branch of the vagus nerve via non-dermal-penetrating contact with tissue of the concha or tragus of the ear;

positioning the wearable stimulation device about the ear of the patient such that i) the first portion is disposed against the back of the ear and extends over the ear, with the at least one first electrode in non-dermal-penetrating contact with the tissue in front of the ear and surrounding the ear, and ii) the second portion is engaging the concha region and/or the tragus region of the ear of the patient with the at least one second electrode in non-dermal-penetrating contact with the tissue of the concha or tragus of the ear;

connecting the wearable neurostimulation device, via the electrical connector of the first portion of the wearable neurostimulation device, to a pulse generator comprising circuitry configured to provide stimulation pulses;

delivering, via the wearable neurostimulation device, the transcutaneous auricular neurostimulation therapy for a period of time, wherein delivering comprises delivering a first series of the stimulation pulses to the at least one first electrode, and delivering a second series of the stimulation pulses to the at least one second electrode, wherein the first series of the stimulation pulses is delivered in coordination with and/or simultaneous to the second series of the stimulation pulses, and wherein the transcutaneous auricular neurostimulation therapy is configured to upregulate opioid receptor agonists and increase availability of monoamine neurotransmitters.

16. The method of claim 15, wherein delivering the transcutaneous auricular neurostimulation therapy comprises repeatedly delivering the transcutaneous auricular neurostimulation therapy at least daily for two or more days.

17. The method of claim 16, further comprising retaining the wearable neurostimulation device in position for 12 to 48 hours.

18. The method of claim 15, further comprising:
positioning a second wearable neurostimulation device about the other ear of the patient; and
connecting the second wearable neurostimulation device, via a connector of a first portion of the second wearable neurostimulation device, to a second pulse generator comprising circuitry configured to provide a second transcutaneous auricular neurostimulation therapy.

19. The method of claim 18, wherein the second pulse generator and the pulse generator are configured as a single pulse generating device.

20. The method of claim 18, further comprising delivering, via the second wearable neurostimulation device, the second transcutaneous auricular neurostimulation therapy, wherein the second transcutaneous auricular neurostimulation therapy is different than the transcutaneous auricular neurostimulation therapy.

21. The method of claim 15, wherein the transcutaneous auricular neurostimulation therapy is configured to upregulate Brain-Derived Neurotrophic-Factor (BDNF) levels.

22. The method of claim 15, wherein the transcutaneous auricular neurostimulation therapy is configured to upregulate Acetylcholine (ACh) levels.

* * * * *